US006391901B1

(12) United States Patent
Chirgadze et al.

(10) Patent No.: US 6,391,901 B1
(45) Date of Patent: May 21, 2002

(54) THROMBIN INHIBITORS

(75) Inventors: Nickolay Y Chirgadze, Carmel; Michael L Denney, Franklin; Matthew J Fisher, Mooresville, all of IN (US); Robert J Foglesong, Durham, NC (US); Richard W Harper, Indianapolis, IN (US); Mary G Johnson, Durham, NC (US); Ho-Shen Lin, Indianapolis, IN (US); Michael P Lynch, Raleigh, NC (US); Jefferson R McCowan, Indianapolis, IN (US); Shawn C Miller, Noblesville, IN (US); Alan D Palkowitz, Carmel, IN (US); Michael E Richett, Indianapolis, IN (US); Daniel J Sall, Greenwood, IN (US); Gerald F Smith; Kumiko Takeuchi, both of Indianapolis, IN (US); Minsheng Zhang, Warren, NJ (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/423,148

(22) PCT Filed: Apr. 30, 1998

(86) PCT No.: PCT/US98/08717

§ 371 Date: Jan. 21, 2000

§ 102(e) Date: Jan. 21, 2000

(87) PCT Pub. No.: WO98/48804

PCT Pub. Date: Nov. 5, 1998

Related U.S. Application Data

(60) Provisional application No. 60/045,188, filed on Apr. 30, 1997.

(51) Int. Cl.$^7$ ............... A61K 31/4025; A61K 31/4178; A61K 31/422; A61K 31/381; C07D 333/52; C07D 409/12; C07D 409/14; C07D 413/14

(52) U.S. Cl. ............. 514/376; 514/324; 514/337; 514/233.5; 514/369; 514/365; 514/372; 514/374; 514/378; 514/380; 514/397; 514/406; 514/422; 514/443; 544/141; 544/145; 546/202; 546/276.4; 548/181; 548/214; 548/248; 548/232; 548/305.1; 548/364.4; 549/32

(58) Field of Search ............... 549/32; 548/525, 548/518, 232, 305.1, 214, 364.4, 181, 248; 544/141, 145; 546/202, 276.4; 514/324, 337, 233.5, 369, 365, 372, 374, 376, 378, 380, 397, 406, 422, 443

(56) References Cited

U.S. PATENT DOCUMENTS 3,274,213 A 9/1966 Lednicer ............. 260/326.5
3,293,263 A 12/1966 Lednicer ............. 260/326.5
4,001,426 A 1/1977 Brenner et al. .......... 424/285
4,007,204 A 2/1977 Descamps et al. ....... 260/330.5
4,133,814 A 1/1979 Jones et al. ............. 260/326.55
4,418,068 A 11/1983 Jones et al. ............. 424/267
5,371,091 A 12/1994 Misra et al. ............. 514/314
5,441,965 A 8/1995 Sall et al. ............... 514/324
5,472,962 A 12/1995 Koizumi et al. ......... 514/233.5
5,510,357 A 4/1996 Palkowitz ............... 514/324
5,518,735 A 5/1996 Sturzebecher et al. .... 424/449
5,523,309 A 6/1996 Bryant et al. ............ 514/320
5,532,254 A 7/1996 Bowling ................. 514/320
5,567,828 A 10/1996 Dodge et al. ............ 549/51
5,576,343 A 11/1996 Nagahara et al. ........ 514/422
6,025,382 A 2/2000 Bastian et al. ........... 514/422

FOREIGN PATENT DOCUMENTS

| EP | 0 617030 | 9/1994 | |
| EP | 738725 | * 10/1996 | ......... C07D/409/12 |
| WO | WO 95/10513 | 4/1995 | |
| WO | WO 95/17095 | 6/1995 | |
| WO | WO 95/17382 | 6/1995 | |
| WO | WO 96/11677 | 4/1996 | |
| WO | WO 97/25033 | 7/1997 | |

OTHER PUBLICATIONS

Grese et al., Med. Chem., Jan. 17, 1997, 40(2), 146–167.*
Martin et al., Bioorg. Med. Chem. Lett., Apr. 8, 1997, vol. 7, No. 7, pp. 887–892.*
Sall, et al., "Dibasic benzo[b]thiophene derivatives as a novel class of active site–directed thrombin inhibitors. 1. Determination of the serine protease selectivity, structure–activity relationships, and binding orientation, " *J. Med. Chem.*, vol. 40, No. 22, Oct. 24, 1997.
Bastian, et al., "Preparation of [(pyrrolidinoalkoxy)phenyl]–benzothiophenes and analogs as thrombin inhibitors," *Chemical Abstracts*, vol. 127, No. 13 (1997), 176339x.
Jones, C., et al., *J. Med. Chem.*, 22 (8), 962–966 (1979).
Jones, C., et al., *J. Med. Chem.*, 27 (8), 1057–1066 (1984).
Delgado and Remens, *Textbook of Organic Medicinal and Pharmaceutical Chemistry*, 9$^{th}$ Edition, 30–31 (1991).
Green and Wuts, *Protective Groups in Organic Syntnesis*, 2$^{nd}$ Edition, 77–79 (1991).
Robert M. Scarborough, "Chapter 8. Anticoagulant Strategies Targeting Thrombin and Factor Xa," *Annual Reports in Medicinal Chemistry*, (1995) 30, pp. 71–80.

* cited by examiner

Primary Examiner—Laura L. Stockton
(74) Attorney, Agent, or Firm—Thomas E. Jackson; Arvie J. Anderson

(57) ABSTRACT

This application relates to novel compounds of formula I (and their pharmaceutically acceptable salts), as defined herein, processes and intermediates for their preparation, pharmaceutical formulations comprising the novel compounds of formula I, and the use of defined compounds of formula I as thrombin inhibitors.

47 Claims, No Drawings

THROMBIN INHIBITORS

This application is a 371 of PCT/US 98/08717 filed Apr. 30, 1998 which claims the benefit of U.S. Provisional Application No. 60/045,188, filed Apr. 30, 1997.

This invention relates to thrombin inhibitors which are useful anticoagulants in mammals. In particular it relates to heterocyclic derivatives having high anticoagulant activity, and antithrombotic activity. Thus, this invention relates to new inhibitors of thrombin, pharmaceutical compositions containing the compounds as active ingredients, and the use of the compounds as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic agents are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation.

Anticoagulation currently is achieved by the administration of heparins and coumarins. Parenteral pharmacological control of coagulation-and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin. See, for example Robert M. Scarborough, *Annual Reports in Medicinal Chemistry*, (1995), 30, 71–80.

Although the heparins and coumarins are effective anticoagulants, no commercial drug has yet emerged from the small synthetic molecules; and despite the continuing promise for this class of compounds, there still exists a need for anticoagulants which act selectively on thrombin, and which, independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent thrombin inhibitors that may have high bioavailability following oral administration.

According to the invention there is provided a method of inhibiting thrombin comprising using an effective amount of a thrombin inhibiting compound of formula I (or a pharmaceutically acceptable salt thereof)

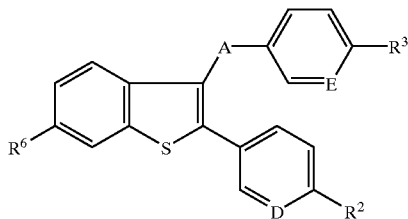

wherein
A is carbonyl or methylene;
D is CH, $CR^d$ or N in which $R^d$ is methyl or methoxy;
E is CH, $CR^e$ or N in which $R^e$ is methyl, methoxy or halo;
$R^2$ is $-NR^a-CO-(CH_2)_m-R^b$ or $-O-CH_2-R^b$ in which m is 0 or 1, $R^a$ is hydrogen or methyl, and Rb is a ring of formula XII or formula XIII

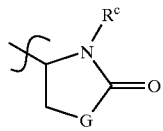

XII

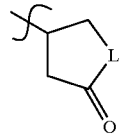

XIII in which G is O, S, NH, $CH_2$ or $CH_2-CH_2$ and $R^c$ is hydrogen or methyl, and L is $NR^f$ or $CH_2$ and $R^f$ is hydrogen or methyl; or $R^2$ is $-NHCOR^g$ in which $R^g$ is a five-membered heteroaromatic ring having 2 heteroatoms selected from O, S and N and in which the carbonyl group is bonded to a ring carbon situated between a ring heteroatom and another ring carbon; or $R^g$ is 1,1-dioxo-isothiazolidin-3-yl; or $R^g$ is $-COR^u$ in which $R^u$ is methoxy, amino or phenyl; or $R^2$ is $-(CH_2)_n-R^h$, $-O-(CH_2)_n-R^h$ or $-NH-(CH_2)_n-R^h$ in which n is 0, 1 or 2 and $R^h$ is cyclopentyl, cyano, or $-CONR^iR^j$ in which $R^i$ and $R^j$ are independently hydrogen or methyl or the group $NR^iR^j$ is pyrrolidino, piperidino, or morpholino; or $R^2$ is $-X^2-(CH_2)_p-R^k$, or $-O-CH_2-CH(CH_3)-R^k$ in which $X^2$ is a direct bond, methylene or O and p is 1, 2 or 3, provided that when p is 1, then $X^2$ is a direct bond, and $R^k$ is 2-oxopyrrolidin-1-yl or $NHCOR^m$ in which $R^m$ is (1–3C)alkyl, phenyl or pyridyl; or $R^2$ is $-NH-CO-NR^iR^j$ in which $R^i$ and $R^j$ are independently hydrogen or methyl or the group $NR^iR^j$ is pyrrolidino, piperidino, or morpholino; or $R^2$ is $-O-CO-NR^pR^q$ in which $R^p$ and $R^q$ are independently hydrogen, methyl or ethyl or the group $NR^pR^q$ is pyrrolidino, piperidino, or morpholino; or $R^2$ is $-NH-SO_2-R^r$ in which $R^r$ is (1–3C)alkyl or phenyl; or $R^2$ is 2-oxo-oxazolidin-5-yl or 1-hydroxy-2-(methylsulfonylamino)ethyl; and R³ is —X³—(CH₂)ₛ—NRˢRᵗ in which X³ is a direct bond, methylene or O; s is 1 or 2; provided that when s is 1, then X³ is a direct bond; and Rˢ and Rᵗ are independently hydrogen or (1–3C)alkyl or the group NRˢRᵗ is pyrrolidino, piperidino, or morpholino; and R⁶ is hydrogen, hydroxy or methoxy; or A, E, R³ and R⁶ are defined as above; R² is hydrogen; and D is C—NH—CO—NRⁱRʲ or C—NH—CO—CORᵘ in which Rⁱ, Rʲ and Rᵘ are defined as above.

A particular thrombin inhibiting compound of formula I (or a pharmaceutically acceptable salt thereof) is one wherein A is carbonyl or methylene;

D is CH, CRᵈ or N in which Rᵈ is methyl or methoxy;

E is CH, CRᵉ or N in which Rᵉ is methyl, methoxy or halo;

R² is —NRᵃ—CO—(CH₂)ₘ—Rᵇ or —O—CH₂—Rᵇ in which m is 0 or 1, Rᵃ is hydrogen or methyl, and Rb is a ring of formula XII or formula XIII

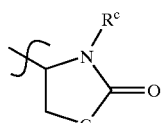

XII

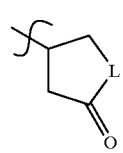

XIII in which G is O, S, NH or CH₂ and Rᶜ is hydrogen or methyl, and L is NRᶠ or CH₂ and Rᶠ is hydrogen or methyl; or R² is —NHCORᵍ in which Rᵍ is a five-membered heteroaromatic ring having 2 heteroatoms selected from O, S and N and in which the carbonyl group is bonded to a ring carbon situated between a ring heteroatom and another ring carbon; or R² is —(CH₂)ₙ—Rʰ, —O—(CH₂)ₙ—Rʰ or —NH—(CH₂)ₙ—Rʰ in which n is 0, 1 or 2 and Rʰ is cyclopentyl, cyano, or —CONRⁱRʲ in which Rⁱ and Rʲ are independently hydrogen or methyl or the group NRⁱRʲ is pyrrolidino, piperidino, or morpholino; or R² is —X²—(CH₂)ₚ—Rᵏ, or —O—CH₂—CH(CH₃)—Rᵏ in which X² is a direct bond, methylene or O and p is 1, 2 or 3, provided that when p is 1, then X² is a direct bond, and Rᵏ is 2-oxopyrrolidin-1-yl or NHCORᵐ in which Rᵐ is (1–3C)alkyl, phenyl or pyridyl; or R² is —NH—CO—NRⁱRʲ in which Rⁱ and Rʲ are independently hydrogen or methyl or the group NRⁱRʲ is pyrrolidino, piperidino, or morpholino; or R² is —O—CO—NRᵖRᵍ in which Rᵖ and Rᵍ are independently hydrogen, methyl or ethyl or the group NRᵖRᵍ is pyrrolidino, piperidino, or morpholino; or R² is —NH—SO₂—Rʳ in which Rʳ is (1–3C)alkyl or phenyl;

R³ is —X³—(CH₂)S—NRˢRᵗ in which X³ is a direct bond, methylene or O; s is 1 or 2; provided that when s is 1, then X³ is a direct bond; and Rˢ and Rᵗ are independently hydrogen or (1–3C)alkyl or the group NRˢRᵗ is pyrrolidino, piperidino, or morpholino; and R⁶ is hydrogen, hydroxy or methoxy.

A particular value for D is CH.

A particular value for E is CH or CRᵉ in which Rᵉ is methyl or methoxy.

One particular value for R² is —NRᵃ—CO—(CH₂)ₘ—Rᵇ in which m is 0, Rᵃ is hydrogen, and Rb is a ring of formula XII in which G is CH₂ and Rᶜ is methyl.

Another particular value for R² is —O—CH₂—Rᵇ in which Rᵇ is a ring of formula XII in which G is O, NH or CH₂ and Rᶜ is hydrogen.

A further particular value for R² is —O—(CH₂)ₙ—Rʰ in which n is 1 and Rʰ is —CONRⁱRʲ in which Rⁱ and Rʲ are independently hydrogen or methyl.

A particular value for R³ is pyrrolidinomethyl, morpholinomethyl or 2-pyrrolidinoethoxy.

A particular value for R⁶ is hydroxy.

A particular value for A is methylene.

A preferred method of the invention includes one wherein said compound of formula I is one of those described herein at Examples 2, 8, 9, 12 and 29, as well as Example 63.

The present invention also provides a method of inhibiting coagulation in a mammal comprising administering to a mammal in need of treatment, a coagulation inhibiting dose of a thrombin inhibiting compound of formula I having any of the above definitions.

The present invention further provides a method of inhibiting thrombin comprising administering to a mammal in need of treatment, a thrombin inhibiting dose of a thrombin inhibiting compound of formula I having any of the above definitions.

Further, the present invention provides a method of treating a thromboembolic disorder comprising administering to a mammal in need of treatment, an effective dose of a thrombin inhibiting compound of formula I having any of the above definitions.

In addition, there is provided the use of a thrombin inhibiting compound of formula I having any of the above definitions for the manufacture of a medicament for treatment of a thromboembolic disorders.

As a further aspect of the invention, there is provided a prodrug (or a pharmaceutically acceptable salt thereof) of any of the above described thrombin inhibiting compounds of formula I which will form a prodrug. (It will be recognized that a thrombin inhibiting compound of formula I also may serve as a prodrug for a different thrombin inhibiting compound of formula I).

As an additional feature of the invention there is provided a pharmaceutical formulation comprising in association with a pharmaceutically acceptable carrier, diluent or excipient, a prodrug of a thrombin inhibiting compound of formula I (or of a pharmaceutically acceptable salt thereof) as provided in any of the above descriptions.

In EP 617030 or in WO 95/17095 there may be disclosed a urethane corresponding to a compound of the formula I wherein A is carbonyl; D is CH; E is CH; R² is —O—CO—NRᵖRᵍ in which one of Rᵖ and Rᵍ is hydrogen, and the other of Rᵖ and Rᵍ is methyl or ethyl; R³ is —O—(CH₂)₂—NRˢRᵗ in which Rˢ and Rᵗ are independently (1–3C)alkyl or the group NRˢRᵗ is pyrrolidino, piperidino, or morpholino; and R⁶ is hydroxy or methoxy.

In WO 95/10513 there may be disclosed a sulfonamide corresponding to a compound of the formula wherein A is carbonyl; D is CH, CRᵈ or N in which Rᵈ is methyl or methoxy; E is CH, CRᵉ or N in which Rᵉ is methyl, methoxy or halo; R² is —NH—SO₂—Rʳ in which Rʳ is (1–3C)alkyl or phenyl; R³ is —X³—(CH₂)ₛ—NRˢRᵗ in which X³ is a direct bond, methylene or O; s is 1 or 2; provided that when s is 1, then X³ is a direct bond; and Rˢ and Rᵗ are independently hydrogen or (1–3C)alkyl or the group $NR^sR^t$ is pyrrolidino, piperidino, or morpholino; and $R^6$ is hydrogen, hydroxy or methoxy.

Otherwise, the thrombin inhibiting compounds of formula I are believed to be novel and, thus, to constitute an additional aspect of the invention. Thus, according to the invention there is provided a novel compound of formula I (or a pharmaceutically acceptable salt thereof) according to any of the above definitions of a compound of formula I, provided that the compound is not one which is not novel as defined in the disclosures noted above.

A pharmaceutically acceptable salt of an antithrombotic compound of the instant invention includes one which is an acid-addition salt made with an acid which provides a pharmaceutically acceptable anion. Thus, an acid addition salt of a novel compound of formula I as provided above made with an acid which affords a pharmaceutically acceptable anion provides a particular aspect of the invention. Examples of such acids are provided hereinbelow.

As an additional aspect of the invention there is provided a pharmaceutical formulation comprising in association with a pharmaceutically acceptable carrier, diluent or excipient, a novel compound of formula I (or a pharmaceutically acceptable salt thereof) as provided in any of the above descriptions.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

It will be appreciated that certain compounds of formula I (or salts or prodrugs, etc.) may exist in, and be isolated in, isomeric forms, including cis- or trans-isomers, as well as optically active, racemic, or diastereomeric forms. It is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against thrombin, it being well known in the art how to prepare or isolate particular forms and how to determine inhibitory properties against thrombin by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

Particular values are listed below for radicals, substituents, and ranges, for illustration only, and they do not exclude other defined values or other values within defined ranges for the radicals and substituents.

A particular value for a (1–3C)alkyl group is methyl, ethyl, propyl or isopropyl.

A compound of formula I may be made by processes which include processes known in the chemical art for the production of known compounds of formula I or of structurally analogous compounds or by a novel process described herein. A process for a novel compound of formula I (or a pharmaceutically acceptable salt thereof), novel processes for a compound of formula I and novel intermediates for the manufacture of a compound of formula I as defined above provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

In general, a compound of formula I may be prepared according to one of the routes outlined in Scheme I, and described in the examples, in which each of $Q^2$, $Q^3$ and $Q^6$, resectively, represents a value defined for the groups $R^2$, $R^3$ and $R^6$, a protected version of such a group, or moiety which can be further elaborated into such a group. Final conversion of a group $Q^2$, $Q^3$ or $Q^6$ into $R^2$, $R^3$ or $R^6$ is carried out at a convenient point, consistent with the chemistry employed. It will be recognized that a number of other routes may be used, particularly those involving condensation of an organometallic species to form a compound of formula C or G in Scheme I.

Scheme I

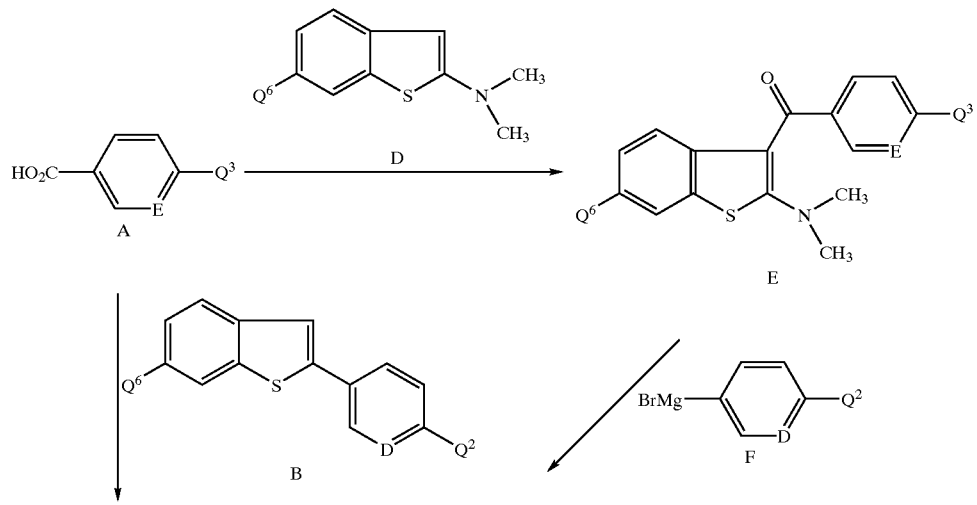

-continued

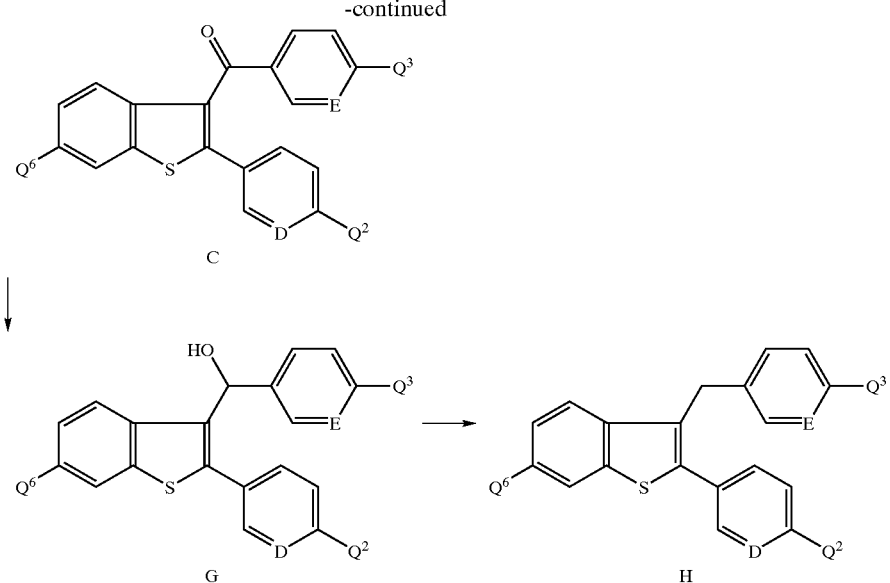

Thus, there is provided a process for preparing a novel compound of formula I (or a pharmaceutically acceptable salt thereof) as provided in any of the above descriptions which is selected from any of those described in the examples, including, (a) for a compound of formula I in which A is methylene, reductive removal of the hydroxy group of a corresponding alcohol of formula II (for example as described in Example 29); and

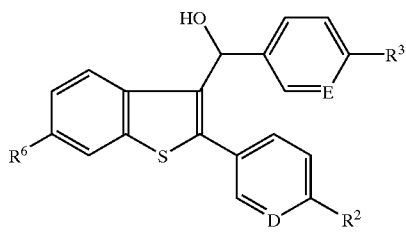

II (b) for a compound of formula I in which $R^2$ is —O—$CH_2$—$R^b$ or —O—$(CH_2)_n$—$R^h$, alkylating the hydroxy group of a corresponding phenol of formula III;

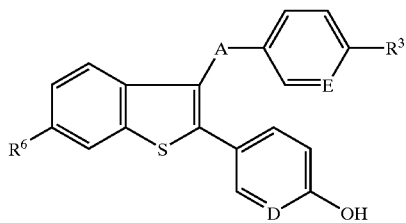

III with a group of formula X—$CH_2$—$R^b$ or X—$(CH_2)_n$—$R^h$, respectively, or a protected derivative thereof, wherein X is a conventional leaving group (for example, as described in Example 2);

whereafter, for any of the above procedures, when a functional group is protected using a protecting group, removing the protecting group;

whereafter, for any of the above procedures, when a pharmaceutically acceptable salt of a compound of formula I is required, it may be obtained by reacting the basic form of such a compound of formula I with an acid affording a physiologically acceptable counterion or by any other conventional procedure.

As used herein, a leaving group is a moiety which is displaced in a nucleophilic substitution reaction, for example a halo group (such as chloro, bromo or iodo), a sulfonate ester group (such as methylsulfonyloxy, p-toluylsulfonyloxy or trifluoromethylsulfonyloxy), or the reactive species derived from treating an alcohol with triphenylphospine, diethyl azodicarboxylate and triethyl amine (in a Mitsunobu reaction).

Novel intermediate or starting material compounds, such as an alcohol of formula II provide a further aspect of the invention. As noted above, an alcohol of formula II may be obtained by reduction of the carbonyl of a corresponding compound of formula I or by condensation of an organometallic species with the requisite aldehyde.

As mentioned above, a compound corresponding to a compound of formula I but in which a functional group is protected may serve as an intermediate for a compound of formula I. Accordingly, such protected intermediates for a novel compound of formula I provide further aspects of the invention. Thus, as one particular aspect of the invention, there is provided a compound corresponding to a novel compound of formula I as defined above in which $R^6$ which is hydroxy, but in which the corresponding substituent is —$OR^p$ in place of hydroxy, wherein $R^p$ is a phenol protecting group other than methyl. Phenol protecting groups are well known in the art, for example. as described in T. W. Greene and P. G. M. Wuts, "Protecting Groups in Organic Synthesis" (1991). Particular values of $R^p$ include, for example, benzyl and allyl. Further, $R^p$ may denote a functionalized resin, for example as disclosed in H. V. Meyers, et al., *Molecular Diversity*, (1995), 1, 13–20.

As mentioned above, the invention includes pharmaceutically acceptable salts of the thrombin inhibiting compounds defined by the above formula I. A particular compound of this invention possesses one or more sufficiently basic functional groups to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

If not commercially available, the necessary starting materials for the preparation of a compound of formula I may be prepared by procedures which are selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

Selective methods of protection and deprotection are well known in the art for preparation of compounds such as those corresponding to a compound of formula I but in which $R^6$ is —$OR^p$ discussed above. Selective methods for cleavage of methyl ethers, as described in the examples, are discussed in Jones, et al., *J. Med. Chem.*, (1984), 27, 1057–1066. For example, the diether 3-(4-methoxybenzoyl)-2-(4-methoxyphenyl)benzo[b]thiophene may be treated with boron tribromide in dichloromethane at −10° C. (1 hour) to afford the monoether 2-(4-hydroxyphenyl)-3-(4-methoxybenzoyl)benzo[b]thiophene, whereas treatment with sodium thioethoxide affords the isomeric monoether 3-(4-hydroxybenzoyl)-2-(4-methoxyphenyl)benzo[b]thiophene. Treatment with boron tribromide under less mild conditions (0° C., 6 hours) or with aluminum chloride and ethanethiol cleaves both ethers.

Generally, the compounds of the invention are isolated best in the form of acid addition salts. Salts of the compounds of formula I formed with acids such as those mentioned above are useful as pharmaceutically acceptable salts for administration of the antithrombotic agents and for preparation of formulations of these agents. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds of the invention are believed to selectively inhibit thrombin over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting thrombin in mammals comprising administering to a mammal in need of treatment an effective (thrombin inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in mammals comprising administering to a mammal in need of treatment an effective (coagulation inhibiting) dose of a compound of formula I.

The thrombin inhibition, coagulation inhibition and thromboembolic disorder treatment contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally, parenterally e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides pharmaceutical formulations for use in the above described therapeutic method. Pharmaceutical formulations of the invention comprise an effective thrombin inhibiting amount of a compound of formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Another embodiment of the present invention is a pharmaceutical formulation comprising an effective amount of a novel compound of formula I or a pharmaceutically acceptable salt or solvate thereof in association with a pharmaceutically acceptable carrier, diluent or excipient therefor.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to Formula I or a pharmaceutically acceptable salt or solvate thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 mL |
| Benzoic acid solution | 0.10 mL |
| Flavor | q.v. |
| Color | q.v. |
| purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:

| Active ingredient | 100 mg |
| --- | --- |
| Isotonic saline | 1,000 mL |

The solution of the above ingredients generally is administered intravenously to a subject at a rate of 1 mL per minute.

The ability of the compounds of the present invention to be an effective and orally active thrombin inhibitor are evaluated in one or more of the following assays.

The compounds provided by the invention (formula I) selectively inhibit the action of thrombin in mammals. The inhibition of thrombin is demonstrated by in vitro inhibition of the amidase activity of thrombin as measured in an assay in which thrombin hydrolyzes the chromogenic substrate, N-benzoyl-L-phenylalanyl-L-valyl-L-arginyl-p-nitroanilide, N-benzoyl-L-Phe-L-Val-L-Arg-p-nitroanilide.

The assay is carried out by mixing 50 $\mu$L buffer (0.03M Tris, 0.15M NaCl, pH 7.4) with 25 $\mu$L of human thrombin solution (purified human thrombin, Enzyme Research Laboratories, South Bend, Ind., at 8 NIH units/mL) and 25 $\mu$L of test compound in a solvent (50% aqueous methanol (v:v)). Then 150 $\mu$L of an aqueous solution of the chromogenic substate (at 0.25 mg/mL) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

$$Kass = \frac{[Thrombin-I]}{[(Thrombin)\times(I)]}$$

Kass is calculated for a range of concentrations of test compounds and the mean value reported in units of liter per mole. In general, a thrombin inhibiting compound of formula I of the instant invention exhibits a Kass of $0.05 \times 10^6$ L/mole or much greater.

By substantially following the procedures described above for human thrombin, and using other human blood coagulation system serine proteases and using fibrinolytic system serine proteases, with the appropriate chromogenic substrates, identified below, the selectivity of the compounds of the present invention with respect to the coagulation factor serine proteases and to the fibronolytic serine proteases are evaluated as well as their substantial lack of interference with human plasma clot fibrinolysis.

Human factors X, Xa, IXa, XIa, and XIIa are purchased from Enzyme Research Laboratories, South Bend, Ind.; human urokinase from Leo Pharmaceuticals, Denmark; and recombinant activated Protein C (aPC) is prepared at Eli Lilly and Co. substantially according to U.S. Pat. No. 4,981,952. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from Kabi Vitrum, Stockholm, Sweden, or from Midwest Biotech, Fishers, Ind. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, using known methods of peptide coupling from commercially available reactants, or purchased from Midwest Biotech, Fishers, Ind.

Human plasmin is purchased from Boehringer Mannheim, Indianapolis, Ind.; nt-PA is purchased as single chain activity reference from American Diagnostica, Greenwich, Conn.; modified-t-PA6 (mt-PA6) is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Thrombin inhibitors preferably should spare fibrinolysis induced by urokinase, tissue plasminogen activator (t-PA) and steptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agents. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *Biochem. J.*, 185, 1–11 (1980); and Smith, et al., *Biochemistry*, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 $\mu$L thrombin (73 NIH unit/mL) to 100 $\mu$L human plasma which contains 0.0229 $\mu$Ci 125-iodine labeled fibrinogen. Clot lysis is studied by overlaying the clots with 50 $\mu$L of urokinase or streptokinase (50, 100, or 1000 unit/mL) and incubating for 20 hours at room temperature. After incubation the tubes are centrifuged in a Beckman Microfuge. 25 $\mu$L of supernate is added into 1.0 mL volume of 0.03 M tris/0.15 M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 $\mu$g/mL concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoaaulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982). In this model preferred compounds of the instant invention reduce the net clot weight to approximately 25–30% of control, or even lower, at an i.v. dose of 33.176 $\mu$mol/kg/h.

$FeCl_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 $\mu$L is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, *Thromb. Res.*, 60:269, 1990).

Spontaneous Thrombolysis Model

In vitro data suggests that thrombin inhibitors inhibit thrombin and, at higher concentrations, may inhibit other serine proteases, such as plasmin and tissue plasminogen activator. To assess if the compounds inhibit fibrinolysis in vivo, the rate of spontaneous thrombolysis is determined by implanting a labeled whole blood clot into the pulmonary circulation. Rat blood (1 mL) is mixed rapidly with bovine thrombin (4 IU, Parke Davis) and $^{125}$I human Fibrogen (5 $\mu$Ci, ICN), immediately drawn into silastic tubing and incubated at 37° C. for 1 hour. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected cpm} - \text{lung cpm})}{\text{injected cpm}} \times 100$$

The fibrinolytic dissolution of the implanted clot occurs time-dependently (see J. P. Clozel, *Cardiovas. Pharmacol.*, 12:520, 1988).

Coagulation Parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and $CaCl_2$ (0.1 mL, 0.025 M) is added to start coagulation. Assays are done in duplicate and averaged.

Index of Bioavailability

For a measure of bioactivity, plasma thrombin time (TT) serves as a substitute for the assay of parent compound on the assumption that observed increments in TT resulted from thrombin inhibition by parent only. The time course of the effect of the thrombin inhibitor upon TT is determined after i.v bolus administration to anesthetized rats and after oral treatment of fasted conscious rats. Due to limitations of blood volume and the number of points required to determine the time course from time of treatment to the time when the response returns to pretreatment values, two populations of rats are used. Each sample population represents alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{\text{AUC po}}{\text{AUC iv}} \times \frac{\text{Dose iv}}{\text{Dose po}} \times 100$$

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombolysis model. Bolus injection volume is 1 mL/kg for i.v., and 5 mL/kg for p.o., and infusion volume is 3 mL/hr.

Statistics

Results are expressed as means +/−SEM. One-way analysis of variance is used to detect statistically significant differences and then Dunnett's test is applied to determine which means are different. Significance level for rejection of the null hypothesis of equal means is $P<0.05$.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity; and lighted from 0600–1800 hours.

Pharmacokinetic Model

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Butler Farms, Clyde, N.Y., Michigan, U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-$\mu$A direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for at least 30 minutes.

Hematoloo and Template Bleeding Time Determinations

Whole blood cell counts, hemoglobin, and hematocrit values are determined on a 40-$\mu$L sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment. All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean ±SEM. All studies are conducted in accordance with the guiding principles of the American Physiological Society. Further details regarding the procedures are described in Jackson, et al., *J. Cardiovasc. Pharmacol.*, (1993), 21, 587–599.

The following Examples are provided to further describe the invention and are not to be construed as limitations thereof.

The abbreviations, symbols and terms used in the examples have the following meanings.

Ac=acetyl
AIBN=azobisisobutyronitrile
Anal.=elemental analysis
Bn or Bzl=benzyl
Bu=butyl
n-BuLi=butyllithium
calcd=calculated
Cbz=benzyloxycarbonyl
DCC=dicyclohexylcarbodiimide
DIBAL-H=diisobutyl aluminum hydride
DMF=dimethylformamide DMSO=dimethylsulfoxide
Et=ethyl
EtOAc=ethyl acetate
Et₃N=triethylamine
Et₂O=diethyl ether
EtOH=ethanol
EtSH=ethanethiol
FAB=Fast Atom Bombardment (Mass Spectrascopy)
FDMS=field desorption mass spectrum
Hex=hexanes
HOAt=1-hydroxy-7-azabenzotriazole
HPLC=High Performance Liquid Chromatography
HRMS=high resolution mass spectrum
i-PrOH=isopropanol
IR=Infrared Spectrum
LAH=lithium aluminum hydride
Me=methyl
MeI=methyl iodide
MeOH=methanol
MPLC=Medium Pressure Liquid Chromatography
NBS=N-bromosuccinimide
NMR=Nuclear Magnetic Resonance
Ph=phenyl
PPA=polyphosphoric acid
i-Pr=isopropyl
Rochelle's Salt=potassium sodium tartrate
RPHPLC=Reversed Phase High Performance Liquid Chromatography
SCX resin=Strong Cation exchange resin
$SiO_2$=silica gel
SM=starting material
TBS=tert-butyldimethylsilyl
TEA=triethylamine
Temp.=temperature
TFA=trifluoroacetic acid
THF=tetrahydrofuran
TIPS=triisopropylsilyl
TLC=thin layer chromatography
triflic acid=trifluoromethanesulfonic acid Unless otherwise stated, pH adjustments and work up are with aqueous acid or base solutions. PrepLC indicates preparative liquid chromatography using "Prep Pak (TM)" silica cartridges; radial chromatography indicates preparative chromatography using a "Chromatotron (TM)" instrument.

EXAMPLE 1

Preparation of (R)-6-Hydroxy-3-[3-methyl-4-(1-pyrrolidinylmethyl)benzyl]-2-[4-(5-oxopyrrolidin-2-ylcarbonylamino)phenyl]benzo[b]thiophene Oxalate

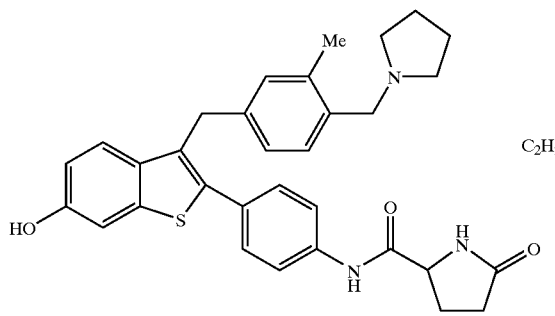

Part A. 6-Methoxy-2-(4-nitrophenyl)benzo[b]thiophene.

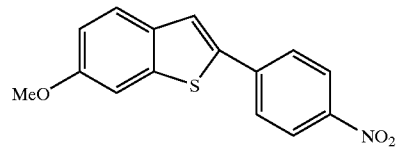

A solution of 15.0 g (71.8 mmol) of 6-methoxybenzo[b]thiophene-2-boronic acid (Part H, below), 15.0 g (74.3 mmol) of 1-bromo-4-nitrobenzene, and 1.50 mg (1.30 mmol) of tetrakis(triphenylphosphine)palladium(0) in 250 mL of THF was treated with 75 mL of 2 M aq $Na_2CO_3$. The mixture was protected from light and was heated to reflux for 16 h. The reaction was cooled to room temperature and was diluted with 200 mL of THF to effect solution. The two layers were separated and the organic layer was washed sequentially with 1 N aq NaOH (200 mL), $H_2O$ (200 mL), and brine (200 mL). The organic phase was dried ($Na_2SO_4$), filtered and concentrated in vacuo to give 24.6 g of a yellow solid. Recrystallization from EtOAc afforded 18.6 g (65.1 mmol; 91%) of the title compound as yellow crystals.

FDMS 285 (M+); Anal. calcd for $C_{15}H_{11}NO_3S$: C, 63.15; H, 3.89; N, 4.91. Found: C, 63.38; H, 4.01; N, 4.81.

Part B. 6-Methoxy-2-(4-aminophenyl)benzo[b]thiophene.

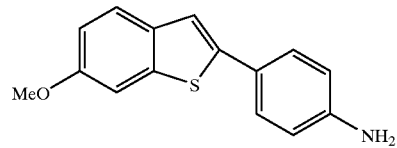

A solution of 9.00 g (31.5 mmol) of 6-methoxy-2-(4-nitrophenyl)benzo[b]thiophene (Part A) in 250 mL of EtOAc was treated with 1.0 g of 10% Pd—C which had been prewetted with the same solvent. The mixture was hydrogenated at 4.1 bar until hydrogen consumption had ceased. The reaction was filtered, concentrated in vacuo, and the resulting solid recrystallized from EtOAc to give 7.90 g (30.9 mmol; 98%) of the title compound as a solid.

FDMS 255 (M+).

Part C. 6-Methoxy-2-(4-acetamidophenyl)benzo[b]thiophene.

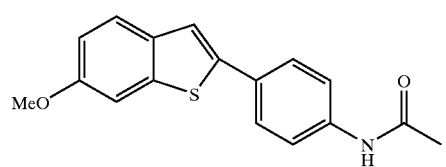

A solution of 15.0 g (58.7 mmol) of 6-methoxy-2-(4-aminophenyl)benzo[b]thiophene (Part B) in 350 mL of pyridine was treated with 17.0 mL (180 mmol) of acetic anhydride in a dropwise manner. After stirring for 2 h, the reaction was concentrated in vacuo to give 15.1 g (50.7 mmol; 87%) of the title compound as a yellow solid.

FDMS 297 (M+); Anal. calcd for $C_{17}H_{15}NO_2S$: C, 68.66; H, 5.08; N, 4.71. Found: C, 68.44; H, 5.05; N, 4.64.

Part D. 3-Methyl-4-[(1-pyrrolidinyl)methyl]phenyl 6-Methoxy-2-(4-acetamidophenyl)benzo[b]thiophen-3-yl Ketone.

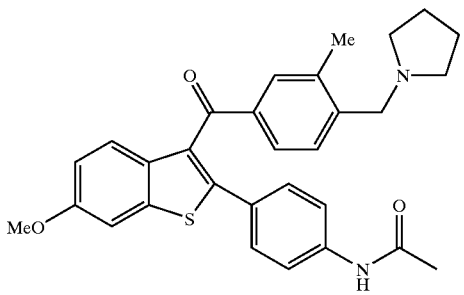

A slurry of 1.25 g (4.89 mmol) of 3-methyl-4-[(1-pyrrolidinyl)methyl]benzoic acid hydrochloride (Part I, below) in 50 mL of dichloroethane was treated with 2 drops of DMF followed by 1.30 mL (14.9 mmol) of oxalyl chloride. The reaction was stirred at ambient temperature until gas evolution ceased and was concentrated in vacuo. The solid was reconstituted in 50 mL dichloroethane. The mixture was cooled to 0° C., was treated with 1.30 g (4.37 mmol) of 6-methoxy-2-(4-acetamidophenyl)benzo[b]thiophene (Part C) and 2.60 g (19.5 mmol) of AlCl$_3$, and was stirred at ambient temperature for 5 h. The reaction was quenched by the addition of 100 mL of sat'd aq NaHCO$_3$. The two layers were separated and the aqueous layer was extracted with EtOAc (4×50 mL). The combined organic layers were washed with H$_2$O (100 mL), dried (K$_2$CO$_3$), filtered, and concentrated in vacuo to give 1.30 g of a yellow foam. Flash chromatography (SiO$_2$; 5% MeOH in CHCl$_3$ sat'd with NH$_4$OH) afforded 730 mg (1.46 mmol; 30%) of the title compound as a foam.

FDMS 498 (M+); Anal. calcd for C$_{30}$H$_{30}$N$_2$O$_3$S: C, 72.26; H, 6.06; N, 5.62. Found: C, 72.20; H, 6.31; N, 5.79.

Part E. 3-Methyl-4-[(1-pyrrolidinyl)methyl]phenyl 6-Methoxy-2-(4-aminophenyl)benzo[b]thiophen-3-yl Ketone.

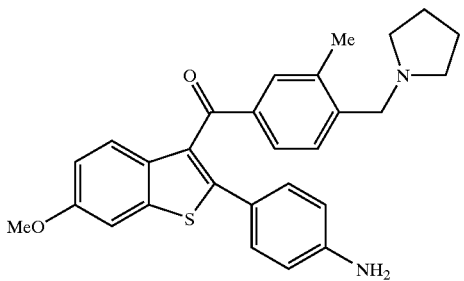

A solution of 200 mg (0.40 mmol) of 3-methyl-4-[(1-pyrrolidinyl)methyl]phenyl 6-methoxy-2-(4-acetamidophenyl)benzo[b]thiophen-3-yl ketone (Part D) in 5 mL of MeOH was treated with 5 mL of conc. aq HCl. The reaction was heated to mild reflux for 1 hr and was concentrated in vacuo. The residue was taken up in 25 mL of H$_2$O, the solution basified to pH 12 with 5 N aq NaOH, and the mixture was extracted with EtOAc (2×25 mL). The combined organic extracts were dried (K$_2$CO$_3$), filtered, and concentrated in vacuo to give 175 mg (0.38 mmol; 96%) of the title compound as a foam.

FDMS 456 (M+); Anal. calcd for C$_{28}$H$_{28}$N$_2$O$_2$S: C, 73.65; H, 6.18; N, 6.14. Found: C, 73.52; H, 6.17; N, 6.03.

Part F. 3-Methyl-4-[(1-pyrrolidinyl)methyl]phenyl (R)-6-Methoxy-2-[4-(5-oxopyrrolidin-2-ylcarbonylamino)phenyl]benzo[b]thiophen-3-yl Ketone.

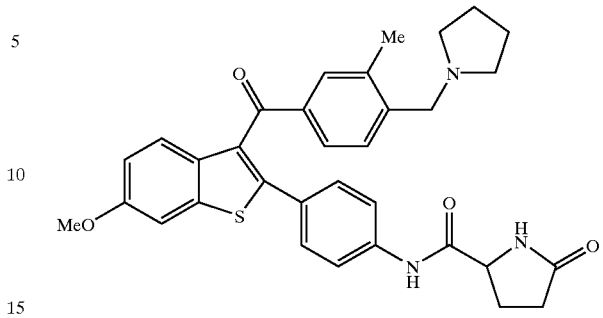

A solution of 1.20 g (2.63 mmol) of 3-methyl-4-[(1-pyrrolidinyl)methyl]phenyl 6-methoxy-2-(4-aminophenyl)benzo[b]thiophen-3-yl ketone (Part E), 0.35 g (2.70 mmol) of D-pyroglutamic acid, and 0.37 g (2.73 mmol) of 1-hydroxy-7-azabenzotriazole in 100 mL of THF was treated with 0.55 g (2.67 mmol) of dicyclohexyl carbodiimide. The reaction was stirred at room temperature for 18 hrs and was diluted with 100 mL each of brine and EtOAc. The two layers were separated and the aqueous layer was extracted with a 1:1 mixture of THF:hexanes (3×100 mL). The combined organic layers were dried (K$_2$CO$_3$), filtered, and concentrated in vacuo to give 2.10 g of a foam. Radial chromatography (SiO$_2$; 2.5% then 5.0% then 7.5% MeOH in CHCl$_3$ sat'd with NH$_4$OH) afforded 1.16 g (2.04 mmol; 78%) of the title compound as a foam.

FDMS 567 (M+); Anal. calcd for C$_{33}$H$_{33}$N$_3$O$_4$S: C, 69.82; H, 5.86; N, 7.40. Found: C, 70.08; H, 5.86; N, 7.59.

Part G. (R)-6-Hydroxy-3-[3-methyl-4-(1-pyrrolidinylmethyl)benzyl]-2-[4-(5-oxopyrrolidin-2-ylcarbonylamino)phenyl]benzo[b]thiophene Oxalate.

A 0° C. solution of 0.50 g (0.88 mmol) of the above ketone in 40 mL of dichloroethane was treated with 0.94 g (7.0 mmol) of AlCl$_3$ followed by 0.55 g (8.8 mmol) of EtSH. The cold bath was removed and the reaction stirred at ambient temperature for 1 hour. Saturated aqueous NaHCO$_3$ (2 mL) was added and the mixture concentrated in vacuo. The residue was reconstituted in 50 mL of n-butanol and reconcentrated to dryness. The resulting solid was rinsed with 50% MeOH in CHCl$_3$. The filtrate was concentrated in vacuo and the residue taken up in 20 mL of DMF. Triethylamine (178 mg 1.76 mmol) was added, the mixture was cooled to 0° C., and the mixture treated with 0.54 g (1.8 mmol) of triisopropylsilyl trifluoromethane sulfonate. The cold bath was removed and the reaction was stirred overnight. The mixturewas quenched with 50 mL of sat'd aq NaHCO$_3$ and extrated with EtOAc (3×50 mL). The combined organic extracts were washed with brine (3×100 mL), dried (MgSO$_4$) and concentrated in vacuo to give 1.1 g of an oil. The residue was purified by radial chromatography (SiO$_2$; 10% MeOH in CHCl$_3$ sat'd with NH$_4$OH) to afford 0.50 g of a foam.

The above material was dissolved in 25 mL of THF, cooled to −35° C. and treated with 1.2 mL of a 1 M solution of LAH in THF (1.2 mmol). The reaction was stirred at −35° C. for 2 h then quenched with satd aq NaHCO$_3$ (30 mL). Ethyl acetate (30 mL) was added, the layers were separated, and the aqueous layer extracted with EtOAc (2×30 mL). The combined organic layers were dried over MgSO$_4$, filtered, and concentrated in vacuo to give 383 mg of a foam. The material was taken up in dichloroethane (40 mL), cooled to 0° C. and treated sequentially with Et$_3$SiH (0.40 g, 3.45 mmol) and TFA (0.79 g, 6.9 mmol). The reaction was stirred at 0° C. for 1 h, poured into satd aq NaHCO$_3$ (20 mL) and extracted with CH$_2$Cl$_2$ (50 mL). The combined organic layers were dried over MgSO$_4$ and concentrated in vacuo to afford 0.60 g of an oil which was purified by radial chromatography (SiO$_2$, 5% then 10% MeOH in CHCl$_3$ satd with NH$_4$OH) to recover 250 mg of an oil.

The oil was dissolved in THF (25 mL) and treated overnight with a solution of KF (0.50 g) in H$_2$O (10 mL). Ethyl acetate (10 mL) was added and the layers were separated. The aqueous layer was extracted with EtOAc (10 mL). The combined organic layers were dried over MgSO$_4$, filtered, and concentrated in vacuo to give 140 mg of a foam (0.26 mmol, 30% overall). The foam was taken up in a minimal amount of MeOH and was treated with a solution of 1 eq of oxalic acid in MeOH. The resulting solution was concentrated in vacuo to give the title compound.

FDMS 539 (M+).

The boronic acid for Part A, above, may be obtained as follows.

Part H. 6-Methoxybenzo[b]thiophene-2-boronic Acid.

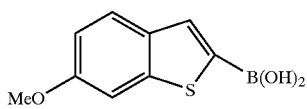

To a solution of 6-methoxybenzo[b]thiophene (Graham, S. L., et al. *J. Med. Chem.* 1989, 32, 2548–2554)(18.13 g, 0.111 mol) in 150 mL of anhydrous THF at −60° C. was added n-BuLi (76.2 mL, 0.122 mol, 1.6 M solution in hexanes), dropwise via syringe. After stirring for 30 min, triisopropyl borate (28.2 mL, 0.122 mol) was introduced via syringe. The resulting mixture was allowed to gradually warm to 0° C. and then partitioned between 1.0 N HCl and EtOAc (300 mL each). The layers were separated, and the organic phase was dried over Na$_2$SO$_4$. Concentration in vacuo produced a white solid that was triturated from Et$_2$O/hexanes. Filtration provided 16.4 g (71%) of 6-methoxybenzo[b]thiophene-2-boronic acid as a white solid.

mp 200° C. (dec); FDMS 208 (M$^+$; 100); $^1$H NMR (DMSO-d$_6$) δ 8.36 (br s), 7.86–7.75 (m, 2H), 7.53 (dd, J 8.1 and 2.0 Hz, 1H), 6.98 (m, 1H), 3.82 (s, 3H).

The benzoic acid for Part D, above may be obtained as follows.

Part I. Methyl 3-Bromo-4-[(1-pyrrolidinyl)methyl]benzoate.

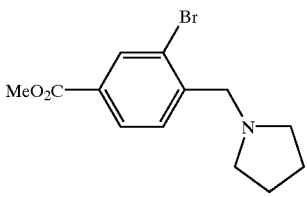

AIBN (79 mg, 48.0 mmol) was added to a stirred suspension of methyl 3-bromo-4-methylbenzoate (11.0 g, 48.0 mmol) and NBS (10.3 g, 57.6 mmol) in CCl$_4$ (400 mL), and the resultant mixture was heated to reflux for 2 h. After cooling to room temperature, the mixture was diluted with hexanes (200 mL) before it was filtered and concentrated to give 14.7 g (crude yield 100%) of methyl 3-bromo-4-(bromomethyl)benzoate.

Part of the crude dibromide (14.7 g) was dissolved in anhydrous CH$_2$Cl$_2$ (60 mL). The solution was cooled to 0° C. and treated with pyrrolidine (9.96 mL, 119 mmol), then it was allowed to stir at room temperature for 2 h. The reaction mixture was diluted with EtOAc (500 mL), washed with half-saturated aqueous NaHCO$_3$ (100 mL), dried over MgSO$_4$, filtered, and concentrated to give an oily residue. The crude product was chromatographed on silica [gradient 0–10% EtOH/Et$_3$N (2/1) in THF/hexanes (1/1)] to provide 6.45 g of the pyrrolidinyl ester (45%) as an oil.

IR (neat) 2953, 1728, 1602 cm$^{-1}$; $^1$H NMR (CDCl$_3$) δ 1.82 (br s, 4H), 2.61 (br s, 4H), 3.77 (s, 2H), 3.92 (s, 3H), 7.59 (d, J=8.0 Hz, 1H), 7.95 (dd, J=8.0 and 1.4 Hz, 1H), 8.20 (d, J=1.4 Hz, 1H); FDMS m/e 297 (M$^+$, $^{79}$Br) and 299 (M$^+$, $^{81}$Br).

Part J. Methyl 3-Methyl-4-[(1-pyrrolidinyl)methyl]benzoate.

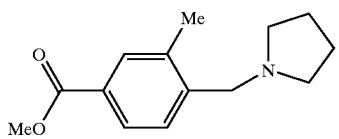

A solution of methyl 3-bromo-4-[(1-pyrrolidinyl)methyl]benzoate (Part I, 16 g, 53.7 mmol) in 110 mL of toluene was treated with Pd(PPh$_3$)$_4$ (3.1 g, 2.68 mmol) and tetramethyltin (22.3 mL, 161.1 mmol). The resulting mixture was heated at 135–140° C. for 36 hr in a sealed tube. After cooling to ambient temperature, the reaction mixture was filtered through diatomaceous earth and concentrated in vacuo. The crude brown residue was purified by PrepLC (SiO$_2$; 97:2:1 hexanes-THF-TEA) to afford 11.4 g (48.9 mmol; 91%) of the title compound as a slightly yellow oil.

FDMS 233 (M$^+$); Anal. calcd for C$_{14}$H$_{19}$NO$_2$: C, 72.08; H, 8.21; N, 6.00. Found: C, 72.29; H, 8.17; N, 5.91.

Part K. 3-Methyl-4-[(1-pyrrolidinyl)methyl]benzoic Acid Hydrochloride.

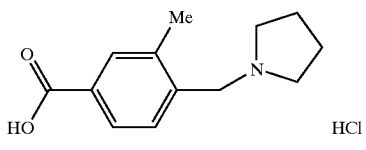

A solution of methyl 3-methyl-4-[(1-pyrrolidinyl)-methyl]benzoate (16 g, 68.6 mmol) in 250 mL of 1 N HCl was heated at reflux overnight (13 hr). After cooling to ambient temperature, the aqueous solution was extracted with EtOAc (150 mL). The aqueous layer was concentrated to give 16.8 g (65.7 mmol; 96%) of the title acid as a white solid.

FDMS 219 (M$^+$); Anal. calcd for C$_{13}$H$_{17}$NO$_2$.HCl: C, 61.06; H, 6.70; N, 5.48. Found: C, 61.22; H, 6.93; N, 5.37.

EXAMPLE 2

Preparation of (S)-6-Hydroxy-3-[3-methyl-4-(1-pyrrolidinyl-methyl)benzyl]-2-[4-(5-oxopyrrolidin-2-ylmethoxy)phenyl]-benzo[b]thiophene Oxalate

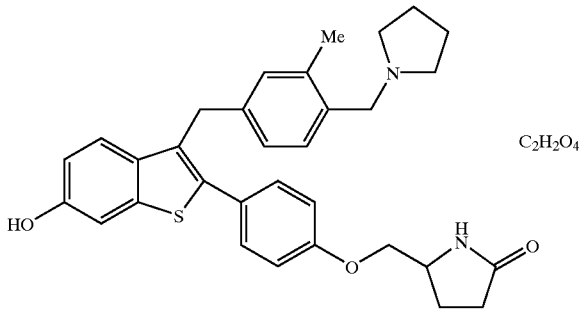

Part A. (S)-6-Methoxy-3-[3-methyl-4-(1-pyrrolidinylmethyl)-benzyl]-2-[4-(5-oxopyrrolidin-2-ylmethoxy)phenyl]-benzo[b]thiophene.

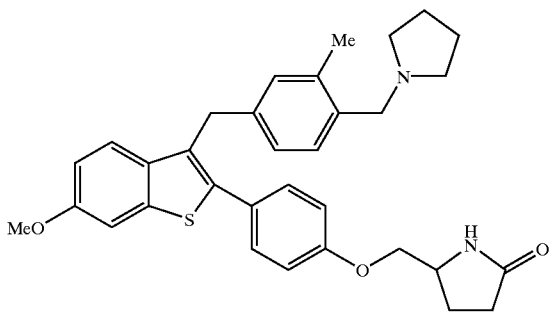

A mixture of 0.33 g (0.75 mmol) of 2-(4-hydroxyphenyl)-6-methoxy-3-[3-methyl-4-(1-pyrrolidinylmethyl)benzyl]-benzo[b]thiophene (Part E, below), 0.79 g (3.0 mmol) of triphenylphosphine, 0.35 g (3.0 mmol) of (S)-(+)-5-(hydroxy-methyl)-2-pyrrolidinone in 10 mL of THF (10 mL) was cooled to 0° C. and was treated with 0.52 g (3.0 mmol) of diethyl azodicarboxylate. The cooling bath was removed and the reaction stirred at ambient temperature for 16 h. The mixture was concentrated in vacuo to approximately 5 mL and purified by flash chromatography ($SiO_2$; 30% THF in hexanes containing 5% TEA). A second chromatography ($SiO_2$; 5% then 10% MeOH in $CHCl_3$ sat'd with $NH_4OH$) afforded 0.20 g (0.37 mmol, 49%) of the title compound as an oil.

FDMS 540 (M+).

Part B. (S)-6-Hydroxy-3-[3-methyl-4-(1-pyrrolidinylmethyl)-benzyl]-2-[4-(5-oxopyrrolidin-2-ylmethoxy)phenyl]-benzo[b]thiophene oxalate.

A 0° C. solution of 0.20 g (0.37 mmol) of (S)-(+)-6-methoxy-3-[3-methyl-4-(1-pyrrolidinylmethyl)benzyl]-2-[4-(5-oxopyrrolidin-2-ylmethoxy)phenyl]benzo[b]thiophene (Part A) in 15 mL of dichloroethane was treated with 0.39 g (2.9 mmol) of $AlCl_3$ followed by 0.21 g (3.3 mmol) of EtSH. The cold bath was removed and the reaction was stirred at ambient temperature for 1 hour. Saturated aq $NaHCO_3$ (25 mL) was added followed by 5% MeOH in EtOAc (50 mL). The two layers were separated and the organic layer dried over $MgSO_4$ and concentrated in vacuo. Purification by radial chromatography ($SiO_2$; 10% then 15% MeOH in $CHCl_3$ sat'd with $NH_4OH$) afforded 0.14 g of the free base of the title compound as a foam. The product was converted to the oxalate salt following the conditions detailed in Example 1, Part G.

$^1$H NMR ($CDCl_3$) d 7.4 (d, 2H), 7.3–7.2 (m, 3H), 6.7 (m, 1H), 6.2 (s, 1H), 4.15 (s, 2H), 4.1–3.9 (m, 4H), 3.8–3.9 (m, 2H), 3.7 (s, 2H), 2.8–2.6 (m, 4H), 2.5–2.35 (m, 2H), 2.3 (s, 3H), 1.9–1.8 (m, 4H); FDMS 526 M(+); Anal. calcd for $C_{32}H_{34}NO_3S.C_2H_2O_4.1.5H_2O$: C, 63.44; H, 6.11; N, 4.35. Found: C, 63.50; H, 5.99; N, 4.30.

The phenolic starting material for Part A, above, may be obtained as follows.

Part C. 4-(6-Methoxybenzo[b]thiophen-2-yl)phenyl Triisopropylsilyl Ether.

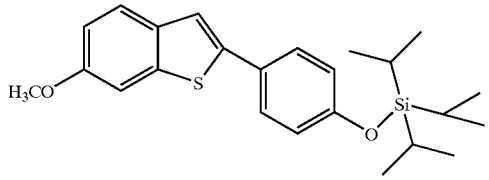

A solution of 6-methoxy-2-(4-hydroxyphenyl)benzo[b]thiophene (16 g, 62.4 mmol) in 160 mL of dry DMF was treated with $Et_3N$ (12.6 g, 124.8 mmol) at 0° C. To this was added in a dropwise manner 28.7 g (93.6 mmol) of triisopropyl trifluoromethanesulfonate. The cooling bath was removed and the reaction mixture was stirred at ambient temperature for 2 h before being poured into 200 mL of saturated aqueous $NaHCO_3$ and 300 mL of brine. This was extracted with 10% EtOAc in hexanes (3×200 mL). The combined extracts were washed with brine (2×300 mL), dried over $MgSO_4$ and concentrated under reduced pressure to give 32 g of an oil which was purified by chromatrography ($SiO_2$; 5% EtOAc in hexanes) to yield 12.3 g. (29.8 mmol, 48%) of the silyl ether as a white solid.

FDMS 412 (M+); Anal. Calcd for $C_{24}H_{32}O_2SSi.0.65EtOAc$: C, 68.50; H, 8.18. Found: C, 68.55; H, 8.16.

Part D. 6-Methoxy-2-[4-[(triisopropylsilyl)oxy]phenyl]-benzo[b]thiophen-3-yl 3-Methyl-4-[(1-pyrrolidinyl)methyl]-phenyl Ketone.

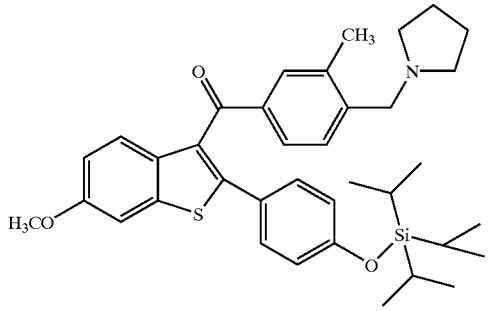

The ketone was prepared in 83% yield from the above benzothiophene, $TiCl_4$, and 3-methyl-4-[(1-pyrrolidinyl)-methyl]benzoic acid hydrochloride by essentially following the procedure detailed for the preparation of Example 1, Part D.

FDMS 613 (M+); Anal. Calcd for $C_{37}H_{47}NO_3SSi.0.23CHCl_3$: C, 69.5; H, 7.40; N, 2.18. Found: C, 69.43; H, 7.48; N, 2.34.

Part E. 2-(4-Hydroxyphenyl)-6-methoxybenzo[b]thiophen-3-yl 3-Methyl-4-[(1-pyrrolidinyl)methyl]phenyl Ketone.

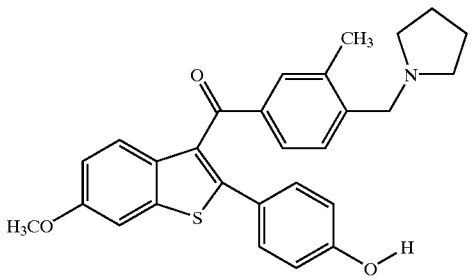

A solution of the above silyl ether (5.23 g, 8.5 mmol) in THF (50 mL) was treated with a 1 M THF solution of tetrabutylammonium fluoride (8.5 mL) at ambient temperature. The reaction was stirred for 16 h, concentrated in vacuo, mixed with $CHCl_3$ and purified by chromatography ($SiO_2$; 2.5% MeOH in $CHCl_3$) to afford 3.8 g (8.3 mmol, 98%) of the phenoxy product as an oil.

$^1$H NMR (Free base-$CDCl_3$) δ 7.65 (d, 1H), 7.53 (s, 1H), 7.48 (d, 1H), 7.32 (d, 1H), 7.21–7.16 (m, 3H), 6.99–6.97 (m, 1H), 6.57 (d, 2H), 5.75 (bs, 1H), 3.89 (s, 3H), 3.59 (s, 2H), 2.6–2.5 (m, 4H), 2.25 (s, 3H), 1.85–1.78 (m, 4H).

EXAMPLE 3

Preparation of (S)-3-[4-[2-(1-Pyrrolidinyl)ethoxy]benzyl]-2-[4-(5-oxopyrrolidin-2-ylmethoxy)phenyl]benzo[b]thiophene Oxalate

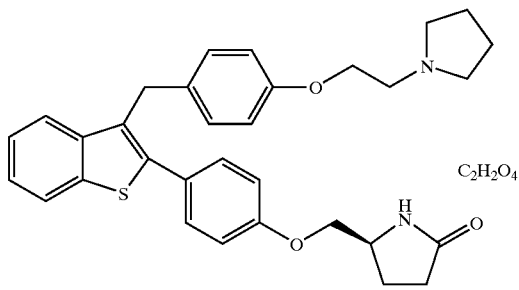

Part A. 2-(4-Hydroxyphenyl)-3-[4-[2-(1-pyrrolidinyl)ethoxy]benzyl]benzo[b]thiophene.

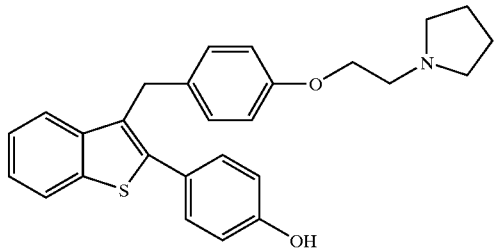

A 0° C. solution of 7.40 g (16.7 mmol) of 2-(4-hydroxyphenyl)benzo[b]thiophen-3-yl 4-[2-( 1-pyrrolidinyl)ethoxy]-phenyl ketone (Part D, below) in 500 mL of THF was treated with 67.0 mL of a solution of DIBAL-H (1 N in toluene; 67 mmol). The reaction was stirred at 0° C. for 1 h and was quenched by the careful addition of 50 mL of MeOH. Saturated aq. sodium/potassium tartrate (200 mL) and EtOAc (200 mL) were added and the reaction stirred vigourously for 1 h. The two layers were separated and the aqueous layer was extracted with EtOAc (3×200 mL). The combined organic layers were dried ($K_2CO_3$), filtered and concentrated in vacuo. The residue was taken up in dichloroethane (300 mL). The solution was cooled to 0° C. and was treated with 20.0 mL (125 mmol) of triethylsilane followed by 13.0 mL (168 mmol) of trifluoroacetic acid. The reaction was stirred at 0° C. for 1 h and was poured into 250 mL of sat'd aq. $NaHCO_3$. The two layers were separated and the organic layer was dried ($K_2CO_3$), filtered, and concentrated in vacuo to give 6.53 g of a foam. Flash chromatography ($SiO_2$; 25% THF: 5% TEA: 70% hexanes) afforded 5.45 g (12.7 mmol; 76%) of the title compound as a foam.

$^1$H NMR (DMSO-$d_6$) d 9.77 (s, 1H), 7.90 (d, J=8.8 Hz, 1H), 7.93–7.87 (m, 1H), 7.32–7.24 (m, 4H), 6.97 (d, J=8.7 Hz, 2H), 6.86–6.75 (m, 4H), 4.13 (s, 2H), 3.97 (t, J=5.8 Hz, 2H), 2.87–2.78 (m, 2H), 2.61–2.52 (m, 4H), 1.69–1.61 (m, 4H).

Part B. (S)-3-[4-[2-(1-Pyrrolidinyl)ethoxy]benzyl]-2-[4-(5-oxopyrrolidin-2-ylmethoxy)phenyl]benzo[b]thiophene Oxalate By essentially following the conditions describe in Example 2, Part A the free base of the title compound was prepared as an oil from 2-(4-hydroxyphenyl)-3-[4-[2-(1-pyrrolidinyl)ethoxy]benzyl]benzo[b]thiophene (Part A) and (S)-(+)-5-(hydroxymethyl)-2-pyrrolidinone in 60% yield following radial chromatography ($SiO_2$; 50% then 70% THF with 5% TEA in hexanes). The oil was converted to the oxalate salt according to the conditions described in Example 1; Part G to afford the title compound.

FDMS 527 (M+1); Anal. calcd for $C_{34}H_{36}N_2O_3S \cdot C_2H_2O_4$: C, 66.22; H, 5.88; N, 4.54. Found: C, 66.04; H, 5.78; N, 4.39.

The phenolic starting material for Part A, above, may be obtained as follows or as described in Example 34.

Part C. 2-(4-Methoxyphenyl)benzo[b]thiophene.

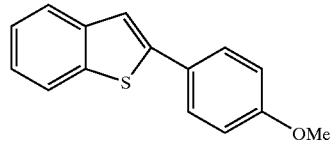

The title compound was prepared in 91% yield from benzo[b]thiophene-2-boronic acid and 4-bromoanisole by essentially following the procedure detailed Example 1, Part A.

mp 188–191° C; $^1$H NMR (DMSO-$d_6$) δ 7.94 (d, J=8.0 Hz, 1H), 7.81 (d, J=7.0 Hz, 1H), 7.73 (m, 2H). 7.71 (s, 1H), 7.35 (m, 2H), 7.05 (d, J=8.0 Hz, 2H), 3.82 (s, 3H); FDMS 240 (M+; 100); Anal. Calcd for $C_{21}H_{23}NO_2S$: C, 71.36; H, 6.56; N, 3.86. Found: C, 71.46; H, 6.60; N, 3.86.

Part D. 2-(4-Methoxyphenyl)benzo[b] thiophen-3-yl 4-[2-(1-Pyrrolidinyl)ethoxy]phenyl Ketone.

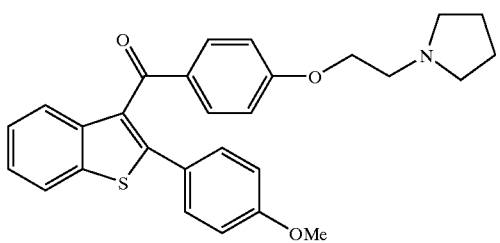

By essentially following the procedure detailed in Example 1, Part D, but using thionyl chloride in refluxing dichloromethane to form the benzoyl choride, the title compound was prepared from 2-(4-methoxyphenyl)-benzo[b]thiophene and 4-[2-(1-pyrrolidinyl)ethoxy]benzoic acid hydrochloride in 59% yield as an oil following radial chromatography (SiO$_2$; gradient of 2–5% MeOH in CH$_2$Cl$_2$).

Part E. 2-(4-Hydroxyphenyl)benzo[b]thiophen-3-yl 4-[2-(1-Pyrrolidinyl)ethoxy]phenyl Ketone.

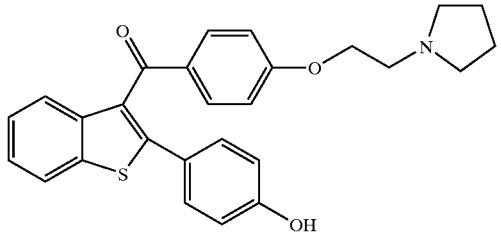

By essentially following the procedure detailed in Example 1, Part G, for the methyl ether cleavage, the title compound was prepared from 2-(4-methoxyphenyl)-benzo[b]thiophen-3-yl 4-[2-(1-pyrrolidinyl)ethoxy]phenyl ketone in 33% yield as an oil following radial chromatography (SiO$_2$; gradient of 2–10% MeOH in CH$_2$Cl$_2$).

FDMS 443 (M$^+$; 100); Anal. Calcd For C$_{27}$H$_{25}$NO$_3$S: C, 73.11; H, 5.68; N, 3.16. Found: C, 73.11; H, 5.89; N, 3.20.

EXAMPLE 4

Preparation of (R)-3-[4-[2-(1-Pyrrolidinyl)ethoxy] benzyl]-2-[4-(S-oxopyrrolidin-2-ylmethoxy)phenyl] benzo[b]thiophene Oxalate

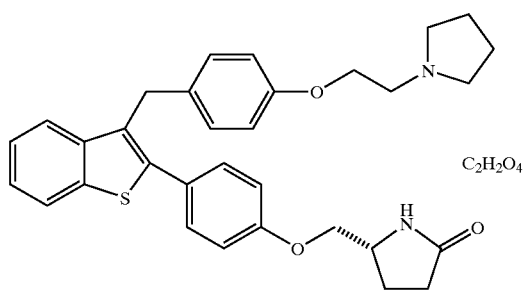

By essentially following the conditions described in Example 2, Part A, the free base of the title compound was prepared as an oil from 2-(4-hydroxyphenyl)-3-[4-[2-(1-pyrrolidinyl)ethoxy]benzyl]benzo[b]thiophene (Example 3; Part A) and (R)-(−)-5-(hydroxymethyl)-2-pyrrolidinone in 51% yield following radial chromatography (SiO$_2$; 50% then 70% THF with 5% TEA in hexanes). The oil was converted to the oxalate salt according to the conditions described in Example 1; Part G, to afford the title compound.

FDMS 527 (M+1).

EXAMPLE 5

Preparation of 3-[4-[2-(1-Pyrrolidinyl)ethoxy] benzyl]-2-[4-[2-(2-oxopyrrolidin-1-yl)ethoxy] phenyl]benzo[b]thiophene Oxalate

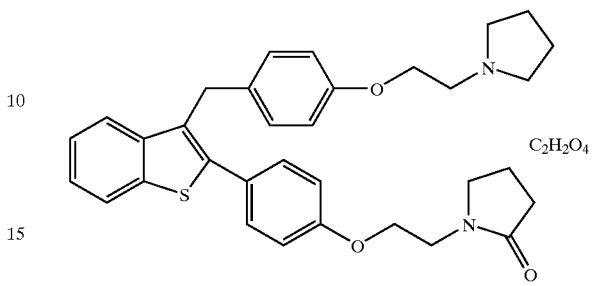

By essentially following the conditions described in Example 2, Part A, the free base of title compound was prepared from 2-(4-hydroxyphenyl)-3-[4-[2-(1-pyrrolidinyl)-ethoxy]benzyl]benzo[b]thiophene (Example 3; Part A) and 1-(2-hydroxyethyl)-2-pyrrolidinone in 36% yield following radial chromatography (SiO$_2$; 30% THF with 5% TEA in hexanes). The oil was converted to the oxalate salt according to the conditions described in Example 1; Part G to afford the title compound.

FDMS 541 (M+1); Anal. calcd for C$_{33}$H$_{36}$N$_2$O$_3$S.0.8C$_2$H$_2$O$_4$: C, 67.82; H, 6.18; N, 4.57. Found: C, 67.94; H, 6.46; N, 4.48.

EXAMPLE 6

Preparation of (R)-2-[4-[2-(Acetylamino)propoxy] phenyl]-3-[4-[2-(1-pyrrolidinyl)ethoxy]benzyl]benzo [b]thiophene Oxalate

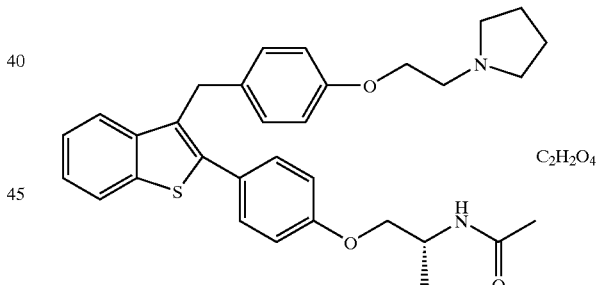

Part A. (R)-(−)-N-t-Boc-2-amino-1-propanol.

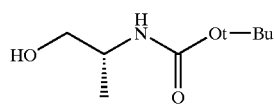

A solution of 2.00 g (26.6 mmol) of (R)-(−)-2-amino-1-propanol in 27 mL of dioxane and 27 mL of 1.0 N aq NaOH was treated with a solution of 5.81 g (26.6 mmol) of di-t-butyl dicarbonate in 5 mL of THF. The reaction was stirred overnight and was concentrated in vacuo. The residue was purified by flash chromatography (SiO$_2$; 40% EtOAc in hexanes) to afford 4.38 g (25.0 mmol; 94%) of the title compound as a paste.

FDMS 176 (M+1); Anal. calcd for C$_8$H$_{17}$NO$_3$: C, 54.84; H, 9.78; N, 7.99. Found: C, 54.88; H, 9.61; N, 8.05.

Part B. (R)-2-[4-[2-(t-Butyloxycarbonylamino)propoxy]-phenyl]-3-[4-[2-(1-pyrrolidinyl)ethoxy]benzyl]-benzo[b]thiophene Oxalate.

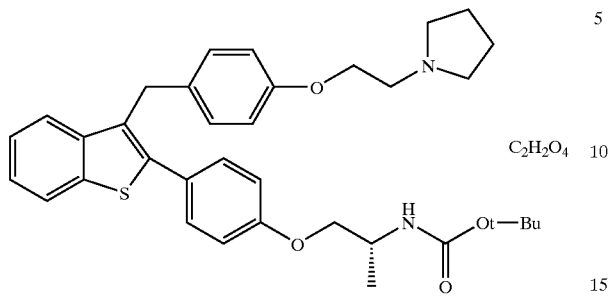

By essentially following the conditions described in Example 2, Part A, the free base of the title compound was prepared as an foam from 2-(4-hydroxyphenyl)-3-[4-[2-(1-pyrrolidinyl)ethoxy]benzyl]benzo[b]thiophene (Example 3; Part A) and (R)-(−)-N-t-Boc-2-amino-1-propanol (Part A) in 65% yield following flash chromatography (SiO$_2$; 1% then 3% then 5% MeOH in CHCl$_3$ sat'd with NH4OH). The product was converted to the oxalate salt according to the method described in Example 1, Part G.

FDMS 587 (M+1); Anal. calcd for C$_{35}$H$_{42}$N$_2$O$_4$S.1.3C$_2$H$_2$O$_4$: C, 64.16; H, 6.39; N, 3.98. Found: C, 64.08; H, 6.59; N, 3.82.

Part C. (R)-2-[4-(2-Aminopropoxy)phenyl]-3-[4-[2-(1-pyrrolidinyl)ethoxy]benzyl]benzo[b]thiophene Dioxalate.

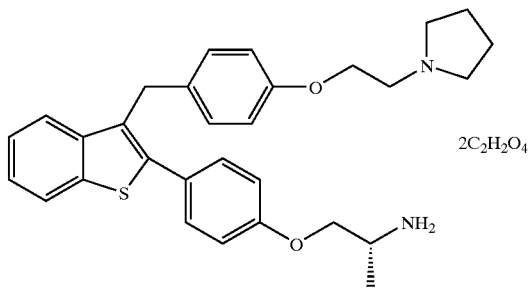

A solution of 0.46 g (0.78 mmol) of the above urethane (Part B) in 10 mL of CH$_2$Cl$_2$ was treated with 0.42 mL (3.86 mmol) of anisole followed by 0.60 mL (7.79 mmol) of TFA. The reaction was stirred for 3 h and was concentrated in vacuo. The residue was subjected to radial chromatography (SiO$_2$; 10% MeOH in CHCl$_3$ sat'd with NH$_4$OH) to afford 216 mg of the free base of the title compound as an oil. The product was converted into the dioxalate salt according to the conditions described in Example 1, Part G.

FDMS 487 (M+1); Anal. calcd for C$_{34}$H$_{38}$N$_2$O$_{10}$S: C, 61.25; H, 5.75; N, 4.20. Found: C, 60.98; H, 5.66; N, 4.00.

Part D. (R)-2-[4-[2-(Acetylamino)propoxy]phenyl]-3-[4-[2-(1-pyrrolidinyl)ethoxy]benzyl]benzo[b]thiophene Oxalate.

A 0° C. solution of 100 mg (0.156 mmol) of the free base of the above amine (Part C) and 0.10 mL (0.72 mmol) TEA in 10 mL of CH$_2$Cl$_2$ was treated with 0.012 mL (0.17 mmol) of acetyl chloride. The reaction was stirred at 0° C. for 4 h and was quenched by the addition of 10 mL of H$_2$O. The two layers were separated. The organic layer was dried over K$_2$CO$_3$, filtered and concentrated in vacuo. The residue was subjected to radial chromatography (SiO$_2$; 35% THF: 5% TEA: 60% hexanes) to afford 41 mg of the free base of the title compound as an oil. The product was converted to the oxalate salt by following the conditions of Example 1; Part G.

EXAMPLE 7

Preparation of 2-[4-[2-(Acetylamino)ethoxy]phenyl]-3-[4-[2-(1-pyrrolidinyl)ethoxy]benzyl]benzo[b]thiophene Oxalate

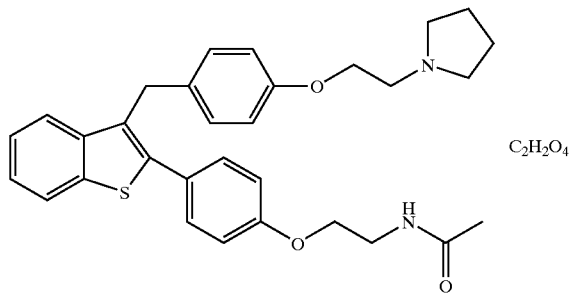

Part A. 2-[4-[2-(t-Butyloxycarbonylamino)ethoxy]phenyl]-3-[4-[2-(1-pyrrolidinyl)ethoxy]benzyl]benzo[b]thiophene Oxalate.

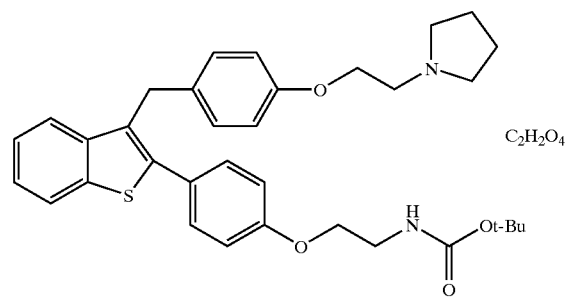

By essentially following the conditions described in Example 2, Part A, the free base of the title compound was prepared as a foam from 2-(4-hydroxyphenyl)-3-[4-[2-(1-pyrrolidinyl)ethoxy]benzyl]benzo[b]thiophene (Example 3; Part A) and N-t-Boc-aminoethanol in 54% yield following flash chromatography (SiO$_2$; 2% then 5% MeOH in CHCl$_3$ sat'd with NH$_4$OH). The product was converted to the oxalate salt according to the method described in Example 1, Part G.

FDMS 487 (M+1); Anal. Calcd for C$_{34}$H$_{38}$N$_2$O$_{10}$S: C, 61.25; H, 5.75; N, 4.20. Found: C, 60.98; H, 5.66; N, 4.00.

Part B. 2-[4-(2-Aminoethoxy)phenyl]-3-[4-[2-(1-pyrrolidinyl)ethoxy]benzyl]benzo[b]thiophene Dihydrochloride.

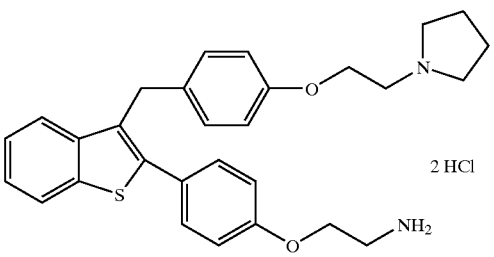

A solution of 1.20 g (2.10 mmol) of the above urethane (Part B) in 5.0 mL of anisole was treated with 10.0 mL of TFA. The reaction was stirred overnight and was concentrated in vacuo. The residue was partitioned between 50 mL of 1 N aq HCl and 50 mL of hexanes. The aqueous layer was separated, washed with hexanes (2×50 mL) and EtOAc (2×50 mL), and lyopholized to afford 964 mg (1.77 mmol; 84%) of the title compound.

FDMS 487 (M+1); Anal. Calcd for C$_{29}$H$_{32}$N$_2$O$_2$S.C$_2$HCl: C, 63.84; H, 6.28; N, 5.13. Found: C, 64.14; H, 6.33; N, 5.11.

Part C. 2-[4-[2-(Acetylamino)ethoxy]phenyl]-3-[4-[2-(1-pyrrolidinyl)ethoxy]benzyl]benzo[b]thiophene Oxalate.

By essentially following the procedure detailed in Example 6, Part D, the free base of the title compound was prepared as an oil in 60% yield from the above amine (Part B) following radial chromatography (SiO$_2$; 30% THF and 5% TEA in hexanes). The product was converted to the oxalate salt according to the method described in Example 1, Part G.

FDMS 487 (M+1); Anal. Calcd for C$_{31}$H$_{34}$N$_2$O$_3$S.C$_2$H$_2$O$_4$: C, 65.55; H, 6.00 N, 4.63 Found: C, 65.40; H, 6.26; N, 4.83.

EXAMPLE 8

Preparation of 6-Hydroxy-3-[3-methyl-4-[(1-pyrrolidinyl)-methyl]benzyl]-2-[4-(2-oxooxazolidin-4-ylmethoxy)phenyl]-benzo[b]thiophene Oxalate

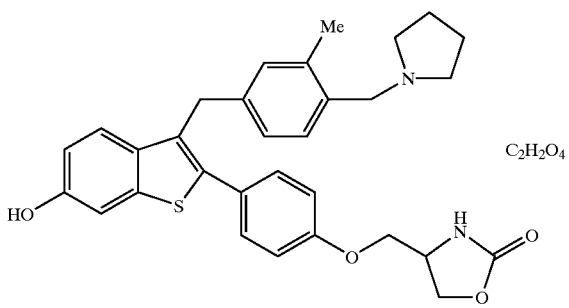

Part A. 6-Benzyloxy-2-[(4-triisopropylsilyloxy)phenyl]-benzo[b]thiophen-3-yl 3-Methyl-4-(1-pyrrolidinylmethyl)-phenyl Ketone.

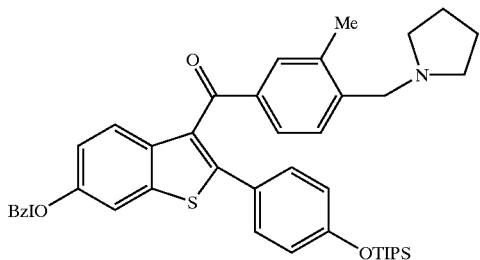

A flamed-dried flask containing 71.0 mg (2.92 mmol) of Mg ribbon was treated with a solution of 1.00 g (3.04 mmol) of 1-bromo-4-(triisopropylsilyloxy)benzene in 6 mL of THF. The mixture was treated with a small crystal of iodine and was heated to mild reflux until all the Mg had been consumed (about 2–3 h). The warm mixture was added via cannula to a 0° C. solution of 982 mg (2.03 mmol) of 6-benzyloxy-2-(dimethylmino)benzo[b]thiophen-3-yl 3-methyl-4-(1-pyrrolidinylmethyl)phenyl ketone (Part G, below) in 20 mL of THF and the solution stirred for 2 h. The cold reaction was quenched by the addition of 50 mL of sat'd aq NH$_4$Cl. The two layers were separated and the aqueous layer was extracted with EtOAc (3×100 mL). The combined organic layers were dried over K$_2$CO$_3$, filitered and concentrated in vacuo to give an oil. Purification by flash chromatography (SiO$_2$; 2% THF and 5% TEA in hexanes) afforded 1.17 g (1.77 mmol; 87%) of the title compound as a bright yellow oil.

FDMS 690 (M+); Anal. calcd for C$_{43}$H$_{51}$NO3SSi: C, 74.85; H, 7.45; N, 2.03. Found: C, 75.07; H, 7.43; N, 1.97.

Part B. 6-Benzyloxy-2-(4-hydroxyphenyl)benzo[b]thiophen-3-yl 3-Methyl-4-(1-pyrrolidinylmethyl)phenyl Ketone.

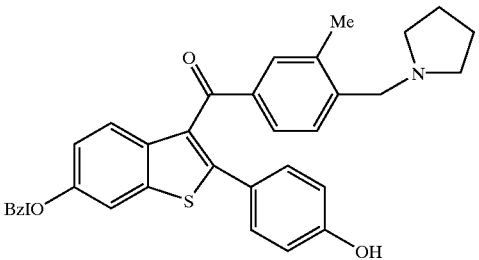

A solution of 8.74 g (13.2 mmol) of 6-benzyloxy-2-[(4-triisopropylsilyloxy)phenyl]benzo[b]thiophen-3-yl 3-methyl-4-(1-pyrrolidinylmethyl)phenyl ketone (Part A) in 200 mL of THF was treated with 14.5 mL of a 1M solution of tetrabutyl-ammonium fluoride in THF (14.5 mmol). The burgundy colored reaction was stirred for 15 min and was poured into 250 mL of sat'd aq NaHCO$_3$. The two layers were separated and the aqueous layer was extracted with EtOAc (4×100 mL). The combined organic layers were dried over K$_2$CO$_3$, filtered and concentrated in vacuo to give 8.74 g of a yellow oil. A 200 mg sample was purified by radial chromatography (SiO$_2$; 1% MeOH in CHCl$_3$ sat'd with NH$_4$OH) to afford 157 mg (95% based on 8.74 g of crude material) of the title compound as a yellow solid.

FDMS 533 (M+); Anal. Calcd for C$_{34}$H$_{31}$NO$_3$S.0.5 MeOH: C, 75.38; H, 6.05; N, 2.55. Found: C, 75.25; H, 6.15; N, 2.82.

Part C. 6-Benzyloxy-3-[3-methyl-4-[(1-pyrrolidinyl)methyl]-benzyl]-2-(4-hydroxyphenyl)benzo[b]thiophene.

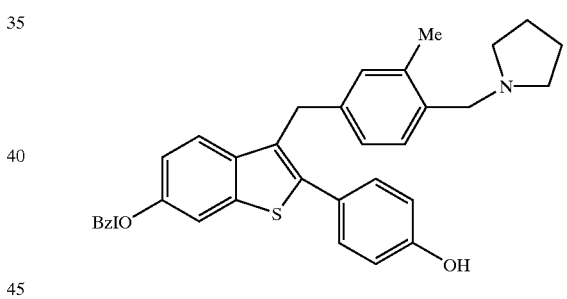

By essentially following the conditions described in Example 3, Part A, the title compound was prepared as a foam in 74% yield from 6-benzyloxy-2-(4-hydroxyphenyl)-benzo[b]thiophen-3-yl 3-methyl-4-(1-pyrrolidinylmethyl)-phenyl ketone (Part B).

FDMS 520 (M+1); Anal. Calcd for C$_{34}$H$_{33}$NO$_2$S:

Part D. 4-Hydroxymethyloxazolidin-2-one.

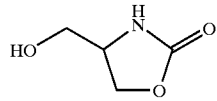

The title compound was prepared by following the conditions of Hchipper et al. (JOC, 1961, 26, 4145). A mixture of 1.0 g (11.0 mmol) of 2-amino-1,2-dihydroxy-propane, 7.0 mL of diethyl carbonate (57.8 mmol) and 70 mg (1.3 mmol) of NaOMe were heated to 120° C. for 0.5 h. The reaction was concentrated in vacuo to give 1.87 g of an oil which was purified by flash chromatography (SiO$_2$; 1% then 2% then 3% MeOH in EtOAc) to afford 874 mg (7.63 mmol; 69%) of the title compound as an oil which solidified on standing.

¹H NMR (DMSO-d₆) d 7.56 (br s, NH), 4.92 (t, J=5.2 Hz, OH), 4.31–4.24 (m, 1H), 4.05–3.96 (m, 1H), 3.75–3.64 (m, 1H), 3.36–3.27 (m, 2H); Anal. calcd for $C_4H_7NO_3$: C, 41.03; H, 6.02; N, 11.96. Found: C, 41.03; H, 5.85; N, 11.83.

Part E. 6-Benzyloxy-3-[3-methyl-4-[(1-pyrrolidinyl)methyl]-benzyl]-2-[4-(2-oxooxazolidin-4-ylmethoxy)phenyl]-3-benzo[b]thiophene.

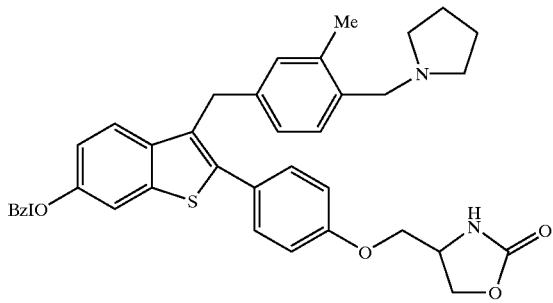

By essentially following the conditions described in Example 2, Part A, the title compound was prepared as an oil from 6-benzyloxy-3-[3-inethyl-4-[(1-pyrrolidinyl)methyl]-benzyl]-2-(4-hydroxyphenyl)benzo[b]thiophene (Part C) and 4-hydroxymethyloxazolidin-2-one (Part D) in 74% yield following radial chromatogrpahy (SiO₂; 30% then 40% THF and 5% TEA in hexanes).

FDMS 619 (M+1); Anal. calcd for $C_{38}H_{38}N_2O_4S$: C, 73.76; H, 6.19; N, 4.53. Found: C, 73.34; H, 6.34; N, 4.18.

Part F. 6-Hydroxy-3-[3-methyl-4-[(1-pyrrolidinyl)methyl]-benzyl]-2-[4-(2-oxooxazolidin-4-ylmethoxy)phenyl]-benzo[b]thiophene Oxalate.

A mixture 390 mg (0.63 mmol) of 6-benzyloxy-3-[3-methyl-4-[(1-pyrrolidinyl)methyl]benzyl]-2-[4-(2-oxo-oxazolidin-4-ylmethoxy)phenyl]benzo[b]thiophene (Part E) and 390 mg of 10% Pd/C in 9 mL of THF was treated with 4 mL of 25% w/v aq $NH_4CO_2$ and the reaction stirred vigorously for 48 h. The mixture was filtered, the two layers separated and the aqueous layer extracted with $CH_2Cl_2$ (2×20 mL). The combined organic layers were dried over $K_2CO_3$, filtered, and concentrated in vacuo to give 430 mg of an oil. Purification by radial chromatography (SiO₂; 1% then 3% then 5% MeOH in CHCl₃ sat'd with $NH_4OH$) afforded 230 mg (0.43 mmol; 69%) of the free base of the title compound as an oil. The product was converted to the oxalate salt according to the conditions described in Example 1, Part G.

FDMS 529 (M+1); Anal. calcd for $C_{31}H_{32}N_2O_4S \cdot C_2H_2O_4$: C, 64.06; H, 5.54; N, 4.53. Found: C, 64.35; H, 5.46; N, 4.32.

The 6-benzyloxy-2-(dimethylamino)benzo[b]thiophene was prepared in a manner similar to the following.

Part G. α-(4-Benzyloxyphenyl)-α-hydroxy-N,N-dimethyl-thioacetamide.

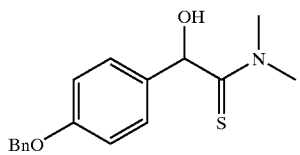

To a solution of distilled diisopropylamine (22.9 mL, 175 mmol) in 400 mL of anhydrous THF at −78° C. was added 1.6 M n-butyllithium in hexanes (100 mL, 160 mmol) over a period of 45 min. The mixture was stirred at −78° C. for 1.5 h. To the solution was cannulated over a period of 1 h a solution of 4-benzyloxybenzaldehyde (30.9 g, 146 mmol) and N,N-dimethylthioformamide (13.7 mL, 160 mmol) in 100 mL of distilled THF. The reaction mixture was stirred at −78° C. for 16 h. The reaction was then quenched with 500 mL of saturated $NH_4Cl$ solution. The mixture was extracted with EtOAc (3×1 L), and the combined organic layers were dried over $MgSO_4$ and concentrated under reduced pressure. The residue was then recrystallyzed from EtOAc/hexanes to afford 20.0 g (66.5 mmol, 46%) of an off-white solid.

mp 104–107° C.; FDMS 301 (M+); Anal. Calcd for $C_{17}H_{19}NO_2S$: C, 67.75; H, 6.35; N, 4.65. Found: C, 67.61; H, 6.37; N, 4.57.

Part H. 6-Benzyloxy-2-(dimethylamino)benzo[b]thiophene.

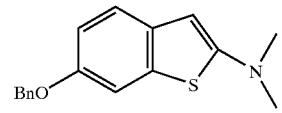

To a solution of thioacetamide (Part G) (500 mg, 1.66 mmol) in 65 mL of dry dichloroethane at room temperature was added dropwise methanesulfonic acid (0.54 ml, 8.3 mmol). The red reaction mixture was stirred for 1.5 h and then poured into 10 mL of saturated aqueous $NaHCO_3$ solution, followed by addition of 3 mL of $H_2O$, and stirred vigorously. The layers were separated and the organic layer was dried over $MgSO_4$ and concentrated under reduced pressure. The residue was then purified by flash chromatography (silica gel, 10% $Et_2O$/hexanes) to afford 327 mg (1.15 mmol, 70%) of a white solid.

mp 78–81° C.; FDMS 283 (M+); Anal. Calcd for $C_{17}H_{17}NOS$: C, 72.05; H, 6.05; N, 4.94. Found: C, 72.22; H, 6.15; N, 4.89.

Part I. 6-Benzyloxy-2-(dimethylamino)benzo[b]thiophen-3-yl 3-Methyl-4-(1-pyrrolidinylmethyl)phenyl Ketone.

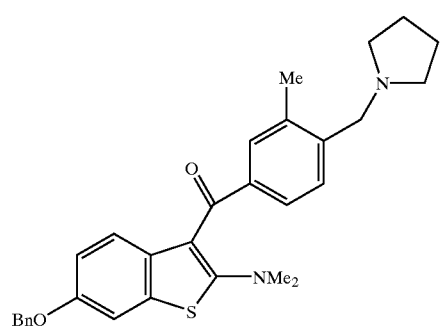

The title compound was prepared from 3-methyl-4-[(1-pyrrolidinyl)methyl]benzoic acid HCl (Example 1, Part K) in 80% yield as a brilliant orange solid essentially as follows:

Oxalyl chloride (2.57 mL, 29.5 mmol) was added to a stirred suspension of 3-methyl-4-[(1-pyrrolidinyl)methyl]-benzoic acid hydrochloride (1.76 g, 5.90 mmol) in anhydrous ClCH$_2$CH$_2$Cl (12 mL), followed by the addition of 2 drops of DMF. The suspension was stirred at room temperature under nitrogen atmosphere for 6 h, then it was concentrated to dryness under vacuum at 50° C.

To the crude benzoyl chloride obtained and suspended in anhydrous chlorobenzene (10 mL) was added 2-dimethylamino-6-benzyloxybenzo[b]thiophene (4.92 mmol) The resultant mixture was heated in an oil bath at 110° C. for 2 h. After cooling to room temperature, the mixture was diluted with EtOAc (80 mL), washed with saturated NaHCO$_3$ (25 mL), dried over MgSO$_4$, filtered, concentrated, and chromatographed on silica [gradient 0–10% EtOH/Et$_3$N (2/1) in THF/hexanes (1/1)] to give the ketone.

FDMS 484 (M$^+$); Anal. calcd for C$_{30}$H$_{32}$N$_2$O$_2$S.HCl: C, 69.15; H, 6.38; N, 5.38. Found: C, 69.36; H, 6.39; N, 5.42.

The silyl ether may be obtained as follows.

Part J. 2-(4-Bromophenoxy)ethyl Triisopropylsilyl Ether.

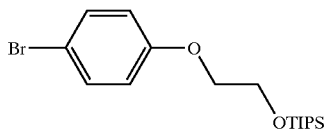

Triisopropylsilyl trifluoromethanesulfonate (24.4 mL, 90.7 mmol) was added to a stirred solution of 2-(4-bromophenoxy)ethanol (15.1 g, 69.8 mmol) and anhydrous triethylamine (19.4 mL, 140 mmol) in anhydrous CH$_2$Cl$_2$ (30 mL) at 0° C. under nitrogen atmosphere. The resultant mixture was stirred for 1 h. The mixture was washed with saturated NaHCO$_3$ (25 mL), extracted with EtOAc (3×75 mL), dried over MgSO$_4$, filtered, concentrated, and chromatographed on silica (10% CH$_2$Cl$_2$ in hexanes) to give 23.4 g (90%) of the silyl ether as a colorless liquid.

IR (thin film) 2944, 1489 cm$^{-1}$; FDMS m/e 372 (M$^+$, $^{79}$Br) and 374 (M$^+$, $^{81}$Br). Anal. Calcd. for C$_{17}$H$_{29}$BrO$_2$Si: C, 54.68; H, 7.83. Found: C, 54.97; H, 7.55.

EXAMPLE 9

Preparation of 6-Hydroxy-3-[3-methyl-4-[(1-pyrrolidinyl)-methyl]benzyl]-2-[4-(2-oxoimidazolidin-4-ylmethoxy)phenyl]-benzo[b]thiophene Oxalate

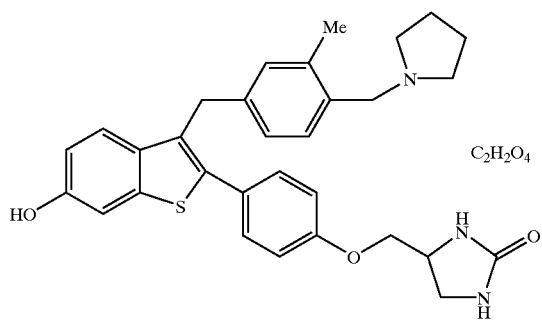

Part A. 6-Benzyloxy-3-[-3-methyl-4-[(1-pyrrolidinyl)methyl]-benzyl]-2-[4-(3-benzyloxycarbonyl-2-oxoimidazolidin-4-yl-methoxy)phenyl]benzo[b]thiophene.

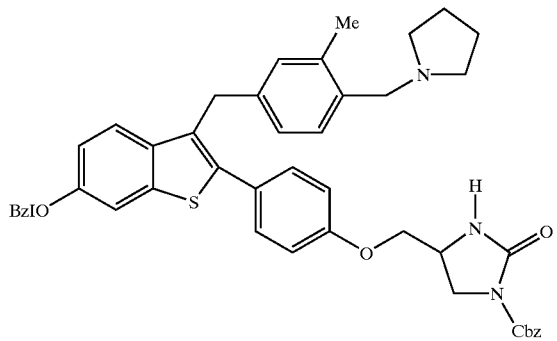

By essentially following the conditions of Example 2, Part A, the title compound was prepared from 1-benzyloxycarbonyl-2-oxo-4-hydroxymethylimidazolidine (Saijo et al. *Chem. Pharm. Bull.* 1980, 28, 1459) and 6-benzyloxy-3-[3-methyl-4-[(1-pyrrolidinyl)methyl]benzyl]-2-(4-hydroxyphenyl)benzo[b]thiophene (Example 8, Part C) in 28% yield following radial chromatography (SiO$_2$; 20% then 25% then 40% THF with 5% TEA in hexanes).

FDMS 753 (M+1); Anal. calcd for C$_{46}$H$_{45}$N$_3$O$_5$S.C$_4$H$_8$O (THF): C, 72.88; H, 6.48; N, 5.10. Found: C, 73.12; H, 6.72; N, 5.22.

Part B. 6-Hydroxy-3-[3-methyl-4-[(1-pyrrolidinyl)methyl]-benzyl]-2-[4-(2-oxoimidazolidin-4-ylmethoxy)phenyl]-benzo[b]thiophene Oxalate.

By essentially following the conditions detailed in Example 8, Part F, the free base of the title compound was prepared as a solid from 6-benzyloxy-3-[3-methyl-4-[(1-pyrrolidinyl)methyl]benzyl]-2-[4-(3-benzyloxycarbonyl-2-oxo-imidazolidin-4-ylmethoxy)phenyl]benzo[b]thiophene (Part A) in 42% yield following radial chromatography (SiO$_2$; 1% then 3% then 5% MeOH in CHCl$_3$ sat'd with NH$_4$OH). The product was converted to the oxalate salt according to the conditions described in Example 1; Part G.

FDMS 528 (M+1); Anal. calcd for C$_{31}$H$_{33}$N$_3$O$_3$S.C$_2$H$_2$O$_4$: C, 64.17; H, 5.71; N, 6.80. Found: C, 64.06; H, 5.81; N, 6.72.

EXAMPLE 10

Preparation of 6-Hydroxy-3-[3-methyl-4-[(1-pyrrolidinyl)-methyl]benzyl]-2-[4-[2-(2-oxoimidazolidin-1-yl)ethoxy]-3-phenyl]benzo[b]thiophene Oxalate

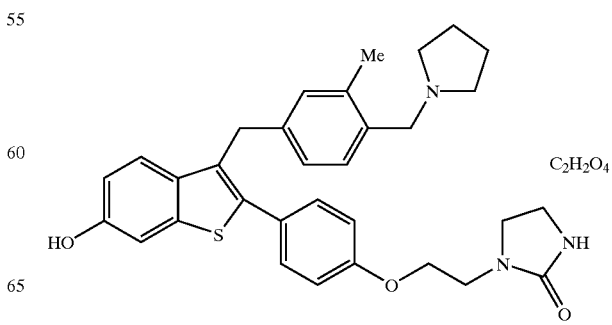

Part A. 6-Benzyloxy-3-[3-methyl-4-[(1-pyrrolidinyl) methyl]-benzyl]-2-[4-[2-(2-oxoimidazolidin-1-yl)ethoxy] phenyl]-benzo[b]thiophene.

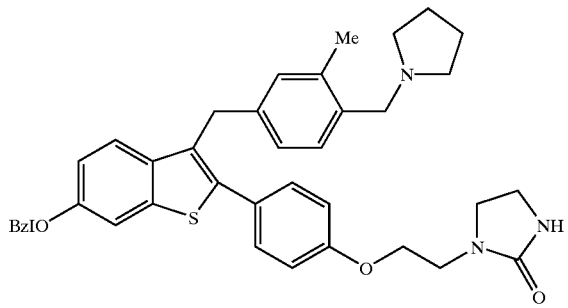

By essentially following the conditions of Example 2, Part A, the title compound was prepared as a foam from 6-benzyloxy-3-[3-methyl-4-[(1-pyrrolidinyl)methyl] benzyl]-2-(4-hydroxyphenyl)benzo[b]thiophene (Example 8, Part C) and 1-(2-hydroxyethyl)-2-imidazolidinone in 71% yield following radial chromatography ($SiO_2$; 20% then 30% then 50% THF with 5% TEA in hexanes).

FDMS 631 (M+).

Part B. 6-Hydroxy-3-[3-methyl-4-[(1-pyrrolidinyl)methyl]-benzyl]-2-[4-[2-(2-oxoimidazolidin-1-yl)ethoxy]phenyl]-benzo[b]thiophene Oxalate.

By essentially following the conditions detailed in Example 8, Part F, the free base of the title compound was prepared as a foam from 6-benzyloxy-3-[3-methyl-4-[(1-pyrrolidinyl)methyl]benzyl]-2-[4-[2-(2-oxoimidazolidin-1-yl)ethoxy]phenyl]benzo[b]thiophene (Part A) in 64% yield following radial chromatography ($SiO_2$; 1% then 3% then 5% MeOH in $CHCl_3$ sat'd with $NH_4OH$). The product was converted to the oxalate salt according to the conditions described in Example 1; Part G.

FDMS 542 (M+1); Anal. calcd for $C_{32}H_{32}N_3O_3S.0.7C_2H_2O_4$: C, 66.34; H, 6.07 N, 6.95. Found: C, 66.32; H, 6.20; N, 6.81.

EXAMPLE 11

Preparation of 6-Hydroxy-3-[3-methyl-4-[(1-pyrrolidinyl)-methyl]benzyl]-2-[4-(2-cyclopentylethoxy)phenyl]-benzo[b]thiophene Oxalate

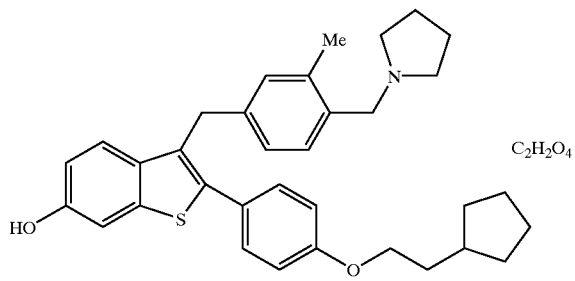

Part A. 6-Benzyloxy-3-[3-methyl-4-[(1-pyrrolidinyl) methyl]-benzyl]-2-[4-(2-cyclopentylethoxy)phenyl]benzo [b]thiophene.

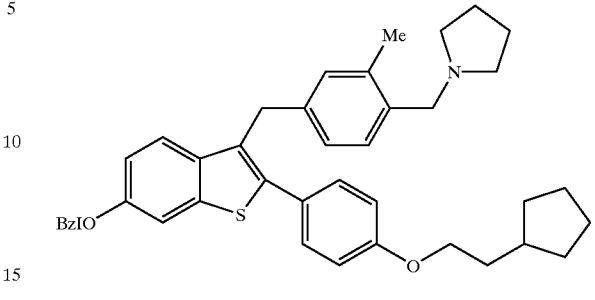

By essentially following the conditions described in Example 2, Part A, the title compound was prepared from 6-benzyloxy-3-[3-methyl-4-[(1-pyrrolidinyl)methyl] benzyl]-2-(4-hydroxyphenyl)benzo[b]thiophene (Example 8; Part C) and 2-cyclopentylethanol in 58% yield following radial chromatography ($SiO_2$; 5% THF and 2.5% TEA in hexanes).

FDMS 615 (M+).

Part B. 6-Hydroxy-3-[3-methyl-4-[(1-pyrrolidinyl)methyl]-benzyl]-2-[4-(2-cyclopentylethoxy)phenyl]benzo[b] thiophene Oxalate.

By essentially following the conditions described in Example 8, Part F, the free base of the title compound was prepared as an oil from 6-benzyloxy-3-[3-methyl-4-[(1-pyrrolidinyl)methyl]benzyl]-2-[4-(2-cyclopentylethoxy) phenyl]-benzo[b]thiophene (Part A) in 97% yield following radial chromatography ($SiO_2$; 10% THF and 2.5% TEA in hexanes). The product was converted to the oxalate salt according to the conditions described in Example 1, Part G.

FDMS 526 (M+1); Anal. calcd for $C_{34}H_{39}NO_2S.1.1C_2H_2O_4$: C, 69.59; H, 6.65; N, 2.24. Found: C, 69.54; H, 6.32; N, 2.55.

EXAMPLE 12

Preparation of (R)-6-Hydroxy-3-[4-[3-methyl-(1-pyrrolidinyl-methyl)benzyl]-2-[4-[(2-oxopyrrolidin-5-yl)methoxy]phenyl]-benzo[b]thiophene

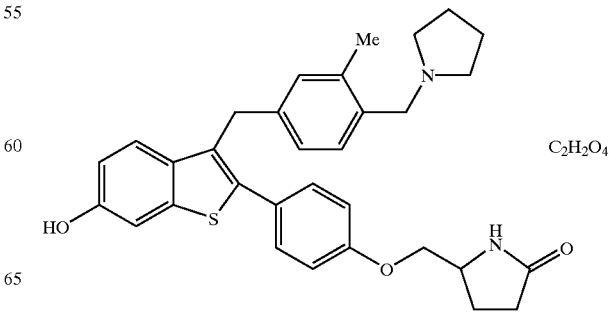

Part A. (R)-6-Benzyloxy-3-[4-[3-methyl-(1-pyrrolidinyl-methyl)benzyl]-2-[4-[(2-oxo-pyrrolidin-5-yl)methoxy]phenyl]-benzo[b]thiophene.

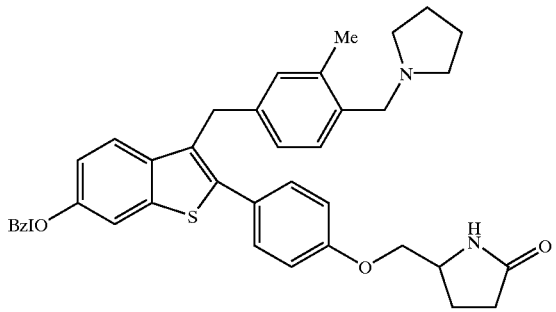

By essentially following the conditions described in Example 2, Part A, the free base of the title compound was prepared as an oil from 6-benzyloxy-3-[methyl-4-[(1-pyrrolidinyl)methyl]benzyl]-2-(4-hydroxyphenyl)benzo[b]thiophene (Example 8, Part C) and (R)-(−)-5-(hydroxymethyl)-2-pyrrolidinone in 61% yield following radial chromatography (SiO$_2$; 30% then 40% then 50% THF with 5% TEA in hexanes).

FDMS 616 (M+)

Part B. (R)-6-Hydroxy-3-[4-[3-methyl-(1-pyrrolidinyl-methyl)benzyl]-2-[4-[(2-oxo-pyrrolidin-5-yl)methoxy]phenyl]-benzo[b]thiophene.

By essentially following the conditions described in Example 8, Part F, the free base of the title compound was prepared as an oil from (R)-(−)-6-benzyloxy-3-[4-[3-methyl-(1-pyrrolidinylmethyl)benzyl]-2-[4-[(2-oxo-pyrrolidin-5-yl)-methoxy]phenyl]benzo[b]thiophene (Part A) in 41% yield following radial chromatography (SiO$_2$; 3% MeOH in CHCl$_3$ sat'd with NH$_4$OH). The product was converted to the oxalate salt according to the conditions described in Example 1, Part G.

FDMS 526 (M+); Anal. calcd for C$_{32}$H$_{34}$N$_2$O$_3$S.1.3C$_2$H$_2$O$_4$: C, 64.56; H, 5.73; N, 4.35. Found: C, 64.69; H, 5.95; N, 4.71.

EXAMPLE 13

Preparation of 6-Hydroxy-2-[4-[2-(methylaminocarbonyl-amino)ethoxy]phenyl]benzo[b]thiophen-3-yl 3-Methoxy-4-[(4-morpholinyl)methyl]phenyl Ketone Oxalate

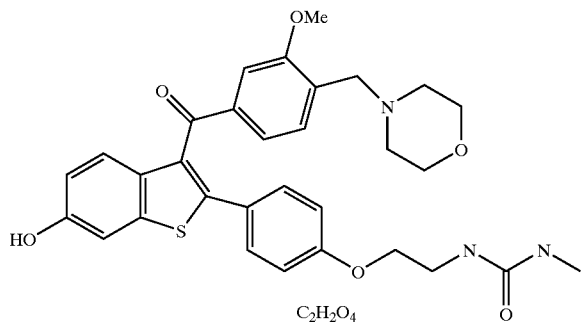

Part A. 2-(4-Bromophenoxy)ethyl Triisopropylsilyl Ether.

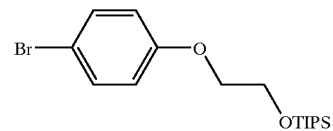

Triisopropylsilyl trifluoromethanesulfonate (24.4 mL, 90.7 mmol) was added to a stirred solution of 2-(4-bromophenoxy)ethanol (15.1 g, 69.8 mmol) and anhydrous triethylamine (19.4 mL, 140 mmol) in anhydrous CH$_2$Cl$_2$ (30 mL) at 0° C. under nitrogen atmosphere. The resultant mixture was stirred for 1 h. The mixture was washed with saturated NaHCO$_3$ (25 mL), extracted with EtOAc (3×75 mL), dried over MgSO$_4$, filtered, concentrated, and chromatographed on silica (10% CH$_2$Cl$_2$ in hexanes) to give 23.4 g (90%) of the silyl ether as a colorless liquid.

IR (thin film) 2944, 1489 cm$^{-1}$; FDMS m/e 372 (M$^+$, $^{79}$Br) and 374 (M$^+$, $^{81}$Br). Anal. Calcd. for C$_{17}$H$_{29}$BrO$_2$Si: C, 54.68; H, 7.83. Found: C, 54.97; H, 7.55.

Part B. 6-Benzyloxy-2-[4-[2-(hydroxy)ethoxy]phenyl]-benzo[b]thiophen-3-yl 3-Methoxy-4-[(4-morpholinyl)methyl]-phenyl Ketone.

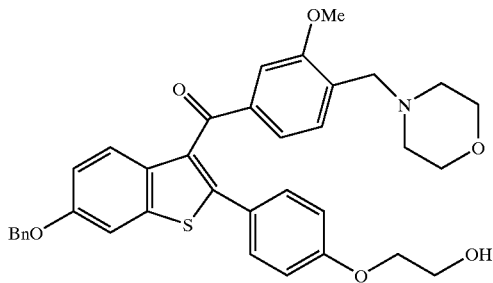

The above silyl ether (2.71 g, 7.26 mmol) was added to a stirred suspension of magnesium ribbons (164 mg, 6.77 mmol) in anhydrous THF (4 mL) under argon atmosphere, followed by the addition of a small iodine chip. The resultant mixture was heated in an oil bath at 60–65° C. for 1.5 h to form a homogeneous Grignard solution. The Grignard solution was cooled to room temperature and diluted with anhydrous THF (10 mL) before it was added to a stirred solution of 6-benzyloxy-2-(dimethylamino)benzo[b]thiophen-3-yl 3-methoxy-4-[(4-morpholinyl)methyl]phenyl ketone (2.50 g, 4.84 mmol) in anhydrous THF (10 mL) at 0° C. under argon atmosphere. The resultant mixture was stirred at 0° C. for 1.5 h, then quenched with saturated aqueous NH$_4$Cl (15 mL). After extraction with EtOAc (70 mL×2), the combined organic layers were dried over MgSO$_4$, filtered, and concentrated to give a gummy residue which was dissolved in anhydrous THF (25 mL) and treated with tetrabutylammonium fluoride (5.80 mL, 1 M in THF) at room temperature under nitrogen atmosphere. After stirring for 1 h, the mixture was concentrated under vacuum; the residue was chromatographed on silica [gradient 0–30% MeOH/Et$_3$N (2/1) in EtOAc] to give 2.61 g (88%) of the keto-alcohol as a foam.

IR (neat) 3426 (br), 1646, 1605 cm$^{-1}$; FDMS m/e 609 (M$^+$); Anal. Calcd. for C$_{36}$H$_{35}$NO$_6$S: C, 70.91; H, 5.79; N, 2.30. Found: C, 70.63; H, 5.65; N, 2.04.

Part C. Preparation of 2-[4-(2-Aminoethoxy)phenyl]-6-(benzyloxy)benzo[b]thiophen-3-yl 3-Methoxy-4-[(4-morpholinyl)methyl]phenyl Ketone.

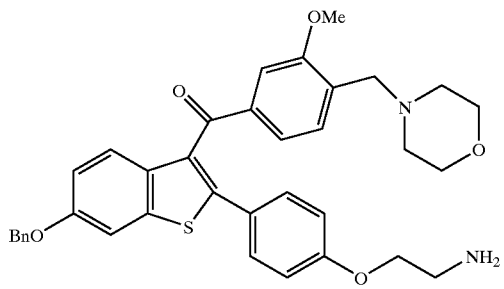

Methanesulfonyl chloride (0.233 mL, 3.01 mmol) was added to a stirred solution of the above benzyloxy-alcohol (1.53 g, 2.51 mmol) and anhydrous triethylamine (1.05 mL) in anhydrous dichloromethane (15 mL) at 0° C. under nitrogen atmosphere, the reaction mixture was allowed to stir at 0° C. for 1.5 h. At room temperature, the mixture was diluted with EtOAc (80 mL), washed with water (20 mL), dried over $MgSO_4$, filtered, and concentrated to give a 1.73 g (100%) of the corresponding mesylate as a foam.

Ammonia gas was bubbled for 5 min through a stirred solution of the mesylate (688 mg, 1.00 mmol) in anhydrous EtOH (15 mL) at 0° C. The solution was then sealed in a thick-walled tube before it was heated in an oil bath at 60° C. for 1.5 days. Concentration and chromatography on silica [gradient 10–50% EtOH/$Et_3N$ (2/1) in EtOAc] gave 395 mg (65%) of the primary amine as a foam.

IR (neat) 3374 (br), 1651, 1605 $cm^{-1}$; FDMS m/e 608 ($M^+$); Anal. Calcd. for $C_{36}H_{36}N_2O_5S$: C,71.03; H,. 5.96; N, 4.60. Found: C, 71.04; H, 5.78; N, 4.63.

Part D. 6-Benzyloxy-2-[4-[2-(methylaminocarbonylamino)-ethoxy]phenyl]benzo[b]thiophen-3-yl 3-Methoxy-4-[(4-morpholinyl)methyl]phenyl Ketone.

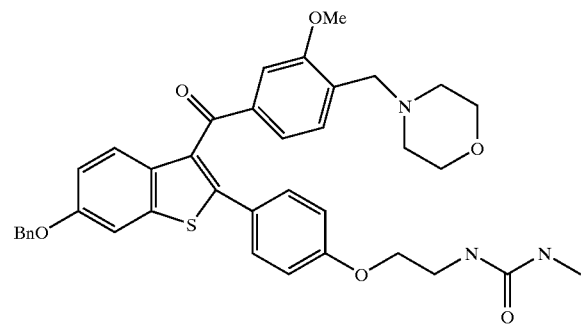

Methyl isocyanate (0.028 mL, 0.475 mmol) was added to a stirred solution of the above primary amine (257 mg, 0.432 mmol) in anhydrous dichloromethane (3 mL) at 0° C. under a nitrogen atmosphere. The reaction mixture was allowed to stir at 0° C. for 30 min, and the reaction mixture was concentrated. The residue was taken up in dichloromethane and chromatographed [gradient 0–25% EtOH/$Et_3N$ (2/1) in EtOAc] to give 287 mg (100%) of the benzyloxy-urea as a yellow foam.

IR (neat) 3354 (br), 2931, 1646 (br), 1600 $cm^{-1}$; FDMS m/e 665 ($M^+$); Anal. Calcd. for $C_{38}H_{39}N_3O_6S$: C, 68.55; H, 5.90; N, 6.31. Found: C, 68.75; H, 5.90; N, 6.41.

Part E. 6-Hydroxy-2-[4-[2-(methylaminocarbonylamino)-ethoxy]phenyl]benzo[b]thiophen-3-yl 3-Methoxy-4-[(4-morpholinyl)methyl]phenyl Ketone Oxalate.

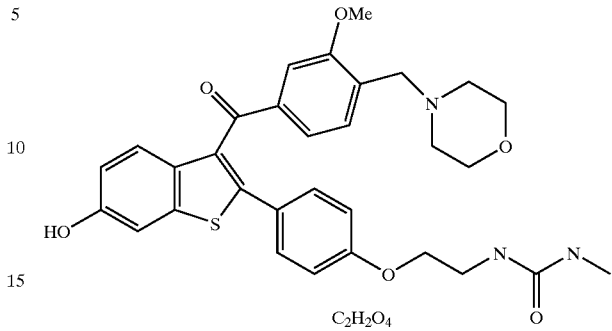

Using procedures similar to those described in Example 8, Part F, (except using $CH_2Cl_2$ instead of EtOAc in the work up and chromatography of the free base on silica [gradient 0–10% EtOH/$Et_3N$ (2/1) in hexanes] rather than radial chromatography) the salt of the hydroxy-urea was obtained from the above benzyloxy-urea as a yellow solid in an overall 72% yield.

IR (KBr) 3378, 3200–2200 (br), 1718, 1642, 1606 $cm^{-1}$; FDMS m/e 576 ($M^++1-1[C_2H_2O_4]$); Anal. Calcd. for $C_{31}H_{33}N_3O_{10}S \cdot C_2H_2O_4$: C, 59.54; H, 5.30; N, 6.31. Found: C, 59.25; H, 5.35; N, 6.42.

The 6-benzyloxy-2-(dimethylamino)benzo[b]thiophen-3-yl 3-methoxy-4-[(4-morpholinyl)methyl]phenyl ketone used in Part B, above, may be obtained using a method similar to that descibed above in Example 8, Part A, but using 3-methoxy-4-(4-morpholinyl)benzoic acid hydrochloride. The benzoic acid hydrochloride may be obtained in a manner similar to the preparation described in Example 1 for the preparation of 3-methyl-4-(1-pyrrolidinylmethyl) benzoic acid hydrochloride; and the ester may be obtained in a manner similar to that described in Example 33, Parts F and G.

EXAMPLE 14

Preparation of (R)-3-[3-Methoxy-4-[2-(1-pyrrolidinyl)-ethoxy]benzyl]-2-[4-(5-oxopyrrolidin-2-ylmethoxy)phenyl]-benzo[b]thiophene Oxalate

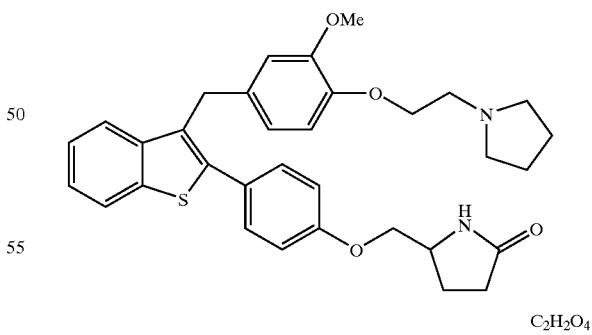

Part A. 2-(4-Hydroxyphenyl)benzo[b]thiophene.

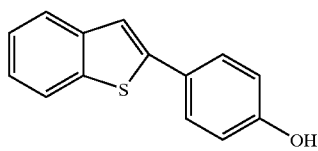

A 0° C. slurry of 12.0 g (49.9 mmol) of 2-(4-methoxyphenyl)benzo[b]thiophene (Example 3; Part C, above) in 250 mL of CH₂Cl₂ was treated with 25 g (99.8 mmol) of BBr₃ in a dropwise manner. The reaction was stirred for 2.5 h and was quenched by the careful addition of 30 mL of MeOH. The mixture was concentrated in vacuo and the residue recrytallized from MeOH to afford 7.94 g (35.1 mmol; 70%) of the title compound as a white solid.

Part B. 2-(4-Triisopropylsilyloxyphenyl)benzo[b]thiophene.

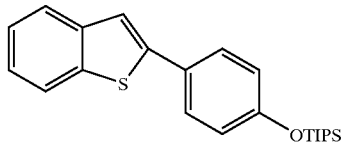

A 0° C. solution of 7.5 g (33.1 mmol) of 2-(4-hydroxyphenyl)benzo[b]thiophene (Part A) and 9.40 mL (66.9 mmol; 2 eq) of TEA in 150 mL of DMF was treated with 13.4 mL (49.8 mmol; 1.5 ea) of triisopropylsilyl triflate. The cold bath was removed and the reaction allowed to stir at ambient temperature for 4 hrs. The mixture was poured into 300 mL of H₂O and the mixture extracted with EtOAc (300 mL). The organic layer was washed with H₂O (3×150 mL) and brine (200 mL), dried over Na₂SO₄, filtered, and concentrated in vacuo to afford an oil. Purification by MPLC (SiO₂; hexanes) afforded 17.20 g (50.1 mmol; 94%) of the title compound as an oil.

FDMS 382 (M+); Anal. calcd for $C_{23}H_{30}OS$: C, 72.20; H, 7.90. Found: C, 72.29; H, 7.99.

Part C. 3-Methoxy-4-[2-(1-pyrrolidinyl)ethoxy]phenyl 2-(4-Triisopropylsilyloxyphenyl)benzo[b]thiophen-3-yl Ketone

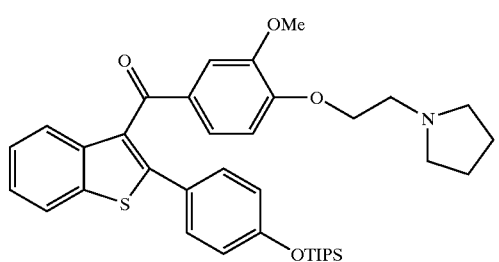

A slurry of 4.34 g (14.4 mmol) of 3-methoxy-4-[2-(1-pyrrolidinyl)ethoxy]benzoic acid hydrochloride (Part G, below) in 75 mL of dichloroethane was treated with 2 drops of DMF followed by 5.00 mL (57.3 mmol; 4 eq) of oxalyl chloride. The reaction was stirred at ambient temperature until gas evolution ceased and was concentrated in vacuo. The solid was reconstituted in 75 mL dichloroethane. The mixture was cooled to 0° C., treated with 5.00 g (13.0 mmol; 0.9 eq) of 2-(4-triisopropylsilyloxyphenyl)benzo[b]thiophene (Part B) and 6.40 mL (58.4 mmol; 4 eq) of TiCl₄, and stirred at ambient temperature for 5 h. The reaction was quenched by the addition of 50 mL of sat'd aq NaHCO₃. The two layers were separated and the aqueous layer was extracted with EtOAc (4×25 mL). The combined organic layers were washed with H₂O (50 mL), dried over K₂CO₃, filtered, and concentrated in vacuo to give an oil. Flash chromatography (SiO₂; 15% THF and 5% TEA in hexanes) afforded 5.60 g (8.90 mmol; 62%) of the title compound as an oil.

FDMS 629 (M+); Anal. calcd for $C_{37}H_{47}NO_4S$: C, 70.55; H, 7.52; N, 2.22. Found: C, 70.71; H, 7.66; N, 2.33.

Part D. 3-Methoxy-4-[2-(1-pyrrolidinyl)ethoxy]phenyl 2-(4-Hydroxyphenyl)benzo[b]thiophen-3-yl Ketone

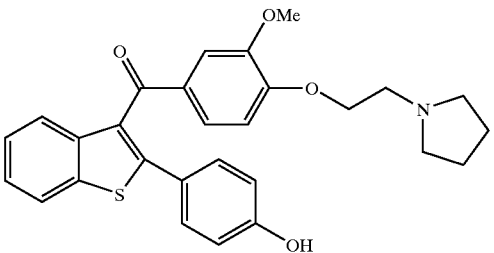

A solution of 5.50 g (8.73 mmol) of 3-methoxy-4-[2-(1-pyrrolidinyl)ethoxy]phenyl 2-(4-triisopropylsilyloxyphenyl)-benzo[b]thiophen-3-yl ketone in 125 mL of THF was treated with 10.0 mL of tetrabutylammonium fluoride solution (1 M in THF; 10.0 mmol). The reaction was allowed to stir for 0.5 h and was poured into 150 mL of sat'd aq NaHCO₃. The two layers were separated and the aqueous layer extracted with EtOAc (4×50 mL). The combined organic extracts were dried over K₂CO₃, filtered, and concentrated in vacuo. The residue was purified by MPLC (SiO₂; 0.5% then 1.5% then 3% MeOH in CHCl₃ sat'd with NH₄OH) to afford 3.85 g (8.13 mmol; 93%) of the title compound as a foam.

FDMS 474 (M+1); Anal. calcd for $C_{28}H_{27}NO_4S \cdot 0.3MeOH$: C, 70.35; H, 5.88; N, 2.90. Found: C, 70.28; H, 5.70; N, 2.66.

Part E. 3-Methoxy-4-[2-(1-pyrrolidinyl)ethoxy]phenyl (R)-2-[4-(5-Oxopyrrolidin-2-ylmethoxy)phenyl]benzo[b]thiophen-3-yl Ketone.

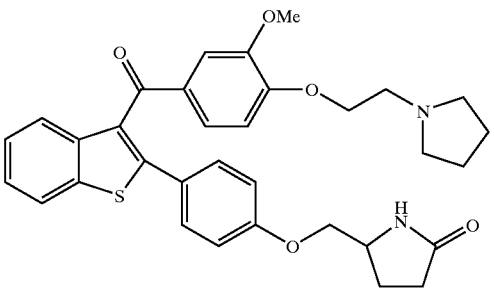

By essentially following the conditions described in Example 2, Part A, the title compound was prepared as an oil from 3-methoxy-4-[2-(1-pyrrolidinyl)ethoxy]phenyl 2-(4-hydroxyphenyl)benzo[b]thiophen-3-yl ketone and (R)-(−)-5-(hydroxymethyl)-2-pyrrolidinone in 70% yield following radial chromatography (SiO₂; 65% then 70% THF with 5% TEA in hexanes).

Part F. (R)-3-[3-Methoxy-4-[2-(1-pyrrolidinyl)ethoxy]-benzyl]-2-[4-(5-oxopyrrolidin-2-ylmethoxy)phenyl]-benzo[b]thiophene Oxalate.

By essentially following the procedures descibed in Example 3, Part A, the title compound was prepared as a white solid from the above ketone in 43% yield following radial chromatography (SiO₂; 1% MeOH in CHCl₃ sat'd with NH₄OH). The product was converted to the oxalate salt by the conditions described in Example 1, Part G.

FDMS 557 (M+1); Anal. calcd for $C_{33}H_{36}N_2O_4S \cdot C_2H_2O_4 \cdot H_2O$: C, 63.24; H, 6.06; N, 4.21. Found: C, 62.91; H, 5.92; N, 4.00.

The benzoic acid for Part C, above, may be obtained as follows.

49

Part G. Methyl 3-Methoxy-4-[2-(1-pyrrolidinyl)ethoxy]-benzoate.

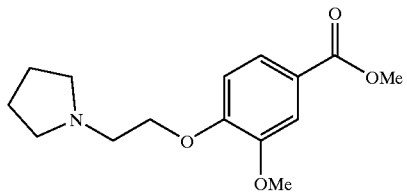

The substituted pyrrolidine was prepared in 94% yield by heating 4-hydroxy-3-methoxybenzoate with excess 1-(2-chloro-ethyl)pyrrolidine hydrochloride and $K_2CO_3$ in DMF, followed by cooling, dilution into cold water and extraction with EtOAc. The product was obtained following drying ($Na_2SO_4$) and evaporation.

$^1$H NMR (CDCl$_3$) δ 7.63 (d, 1H), 7.53 (s, 1H), 6.9 (d, 1H), 4.2 (t, 2H), 3.89 (s, 3H), 3.88 (5, 3H), 2.96 (t, 2H), 2.64–2.61 (m, 4H), 1.85–1.75 (m, 4H); FDMS 279 (M+).

Part E. 3-Methoxy-4-[2-(1-pyrrolidinyl)ethoxy]benzoic Acid Hydrochloride.

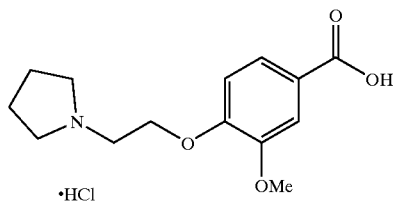

The benzoic acid hydrochloride was prepared in 63% yield from methyl 3-methoxy-4-[2-(1-pyrrolidinyl)ethoxy] benzoate by refluxing the above ester with 5N HCl, followed by mixing with toluene/EtOH before evaporation to dryness. Trituration with hot EtOAc afforded the benzoic acic hydrochloride.

$^1$H NMR (DMSO-d$_6$) δ 11.27 (bs, 2H), 7.57 (d, 1H), 7.55 (s, 1H) 7.12 (d, 1H), 4.44 (t, 2H), 3.82 (s, 3H), 3.5 (bs, 4H), 3.1 (bs, 2H); 1.98 (bs, 2H), 1.89 (bs, 2H); Anal. Calcd for $C_{14}H_{19}NO_4$·HCl: C, 55.72; H, 6.68; N, 4.64. Found: C, 56.01; H, 6.88; N, 4.70.

EXAMPLE 15

Preparation of 3-Methoxy-4-[2-(1-pyrrolidinyl) ethoxy]phenyl (R)-2-[4-(5-Oxopyrrolidin-2-ylmethoxy)phenyl]-benzo[b]thiophen-3-yl Ketone Oxalate

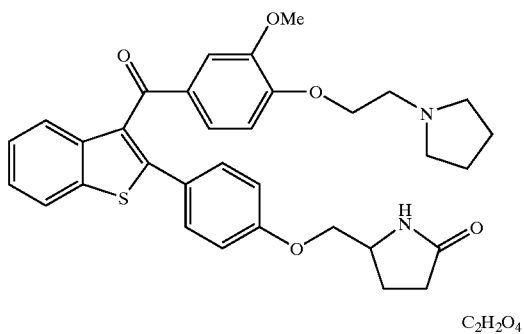

The ketone of Example 14, Part E, was converted to the oxalate salt by the conditions described in Example 1, Part G.

FDMS 571 (M+1); Anal. calcd for $C_{33}H_{34}N_2O_5S·C_2H_2O_4·1.5H_2O$: C, 61.12; H, 5.72; N, 4.07. Found: C, 61.17; H, 5.45; N, 4.14.

EXAMPLE 16

Preparation of 3-[4-[2-(1-Pyrrolidinyl)ethoxy] benzyl]-2-[4-(4-imidazolylcarbonylamino)phenyl] benzo[b]thiophene Dihydrochloride

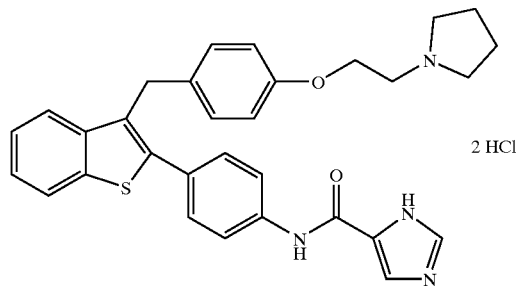

Part A. 2-Dimethylaminobenzo[b]thiophene-3-yl 4-Nitrophenyl Ketone.

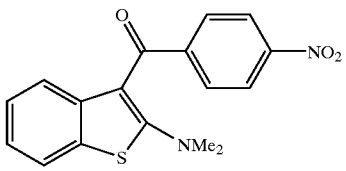

A mixture of 5.00 g (28.2 mmol) of 2-dimethylamino-benzo[b]thiophene (Vesterager et al., *Tetrahedron*, 1973, 29, 321–329) and 6.3 g (33.9 mmol) of 4-nitrobenzoyl chloride in 100 mL of chlorobenzene was heated at 105° C. for 6 h. The reaction was cooled and concentrated in vacuo. Purification of the residue by flash chromatography (SiO$_2$; 5% then 10% then 25% EtOAc in hexanes) afforded 7.51 g (23.0 mmol; 82%) of the title compound as burgundy flakes.

FDMS 326 (M+); Anal. calcd for $C_{17}H_{14}N_2O_3S$: C, 62.56; H, 4.32; N, 8.58. Found: C, 62.71; H, 4.04; N, 8.37.

Part B. 2-Dimethylaminobenzo[b]thiophene-3-yl 4-[2-(1-Pyrrolidinyl)ethoxy]phenyl Ketone.

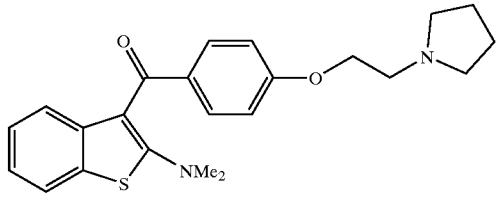

A mixture of 7.00 g (21.4 mmol) of 2-dimethylamino-benzo[b]thiophene-3-yl 4-nitrophenyl ketone (Part A) and sodium hydride (2.0 g, 50 mmol; 60% dispersion in mineral oil) in 150 mL of DMF was treated slowly with a solution of 5.30 mL (45.3 mmole) of 1-(2-hydroxyethyl)pyrrolidine in 25 mL of DMF. The reaction was stirred at ambient temperature for 4 hrs, cooled to 0° C. and quenched by the careful addition of 10 mL of H$_2$O. The solution was poured into 500 mL of H$_2$O and the mixture extracted with EtOAc (5×100 mL). The combined organic layers were washed with H$_2$O (3×100 mL), dried over K$_2$CO$_3$, filtered, and concentrated in vacuo to give 12.41 g of an oil. Purification by MPLC (0.5% then 1% then 2% MeOH in CHCl$_3$ sat'd with NH$_4$OH) afforded a quantitative yield of the title compound as an oil.

FDMS 394 (M+); Anal. calcd for $C_{23}H_{26}N_2O_2S·0.3MeOH$: C, 69.25; H, 6.78 N, 6.93 Found: C, 69.15; H, 6.76; N, 6.98.

Part C. 2-(4-Aminophenyl)benzo[b]thiophene-3-yl 4-[2-(1-Pyrrolidinyl)ethoxy]phenyl Ketone.

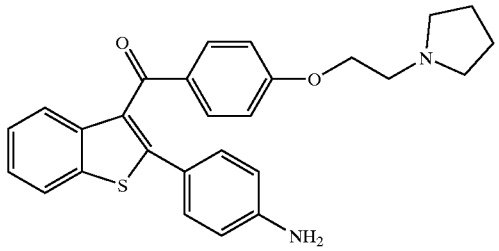

A 3-neck flask containing 580 mg of Mg ribbon was flame-dried under a stream on $N_2$. A solution of 6.7 mL (23.7 mmol) of 4-bromo-N,N-bis(trimethylsilyl)aniline in 15 mL of THF was introduced via cannula and the mixture heated to 60° C. until all the Mg had been consumed. The warm mixture was added via cannula to a 0° C. solution of 8.40 g (21.3 mmol) of 2-dimethylaminobenzo[b]thiophene-3-yl 4-[2-(1-pyrrolidinyl)ethoxy]phenyl ketone (Part B) in 80 mL of THF. The reaction was stirred for 3 h and was quenched by the addition of 150 mL of sat'd aq. $NH_4Cl$. The two layers were separated and the aqueous layer was extracted with EtOAc (3×300 mL). The combined organic layers were dried over $K_2CO_3$, filtered and concentrated in vacuo to give 11.91 g of an oil.

The crude product was taken up in 250 mL of THF and was treated with 30 mL of a 1 M solution of tetrabutylammonium fluoride in THF. The reaction was stirred for 1 hr and was poured into 300 mL of sat'd aq $NaHCO_3$. The two layers were separated and the aqueous layer extracted with EtOAc (4×150 mL). The combined organic layers were dried over $K_2CO_3$, filtered and concentrated in vacuo to give an oil. Purification by MPLC ($SiO_2$; 30% then 40% then 50% THF in hexanes containing 5% triethylamine) afforded 8.31 g (18.8 mmol; 88% over two steps) of the title compound as a yellow foam.

FDMS 442 (M+); Anal. calcd for $C_{27}H_{26}N_2O_2S \cdot C_2H_2O_4 \cdot 1.2 H_2O$: C, 62.85 H, 5.53; N, 5.05. Found: C, 62.52; H, 5.14; N, 4.77.

Part D. 2-(4-Aminophenyl)-3-[4-[2-(1-pyrrolidinyl)ethoxy]-benzyl]benzo[b]thiophene.

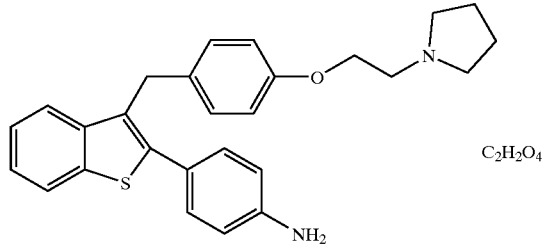

By essentially following the conditions described in Example 3, Part A, the free base of the title compound was prepared as an oil from 2-(4-aminophenyl)benzo[b]thiophene-3-yl 4-[2-(1-pyrrolidinyl)ethoxy]phenyl ketone (Part C) in 85% yield following MPLC ($SiO_2$; 30% then 40% THF with 5% TEA in hexanes). The product was converted to the oxalate salt according to the conditions described in Example 1, Part G.

FDMS 442 (M+); Anal. calcd for $C_{27}H_{28}N_2OS \cdot 2C_2H_2O_4$: C, 61.17; H, 5.30; N, 4.60. Found: C, 61.38; H, 5.57; N, 4.43.

Part E. 3-[4-[2-(1-Pyrrolidinyl)ethoxy]benzyl]-2-[4-(4-imidazolylcarbonylamino)phenyl]benzo[b]thiophene Dihydrochloride.

A slurry of 40 mg (0.35 mmol) of 4-imidazolecarboxylic acid in 5 mL of dichloroethane was treated with 1 drop DMF followed by 0.10 mL (1.37 mmol) of $SOCl_2$. The mixture was heated to mild reflux for 2 h, concentrated in vacuo, and the residue reconstituted in 5 mL dichloroethane. A solution of 300 mg (0.70 mmol) of 2-(4-aminophenyl)-3-[4-[2-(1-pyrrolidinyl)ethoxy]benzyl]benzo[b]thiophene (Part D) in 5 mL of dichloroethane was added and the mixture heated to mild reflux for 16 h. The reaction was diluted with 10 mL of sat'd aq $NaHCO_3$, the two layers were separated, and the aqueous layer extracted with $CHCl_3$ (3×10 mL). The combined organic layers were dried ($K_2CO_3$), filtered and concentrated in vacuo. Radial chromatography ($SiO_2$; 2% then 4% then 5% MeOH in $CHCl_3$ sat'd with $NH_4OH$) afforded 90 mg (0.17 mmol; 49%) of the free base of the title compound as a solid. The product was taken up in 2 mL of $H_2O$ and was treated with 1 mL of 1 N aq HCl. The solution was lyophilized to give the title compound.

$^1$H NMR ($CDCl_3$; free base) δ 9.23 (s, 1H), 7.89–7.03 (m, 1H), 5 7.78–7.70 (m, 3H), 7.59–7.46 (m, 4H), 7.35–7.26 (m, 2H), 7.06 (d, J=8.5 Hz, 2H), 6.76 (d, 8.6 Hz, 2H), 4.23 (s, 2H), 4.08 (t, J=5.6 Hz, 2H), 2.94 (t, J=5.6 Hz, 2H), 2.74–2.63 (m, 4H), 1.91–1.80 (m, 4H).

EXAMPLE 17

Preparation of 3-[4-[2-(1-Pyrrolidinyl)ethoxy] benzyl]-2-[4-(3-pyrazolylcarbonylamino)phenyl] benzo[b]thiophene Dihydrochloride

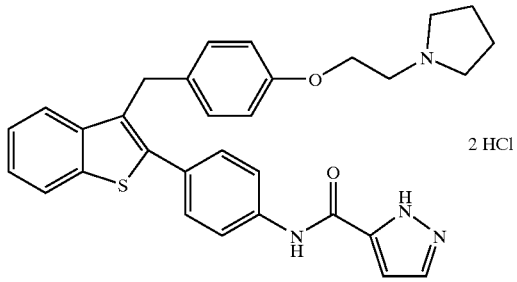

By essentially following the conditions described in Example 16, Part E, the free base of the title compound was prepared as a solid from 2-(4-aminophenyl)-3-[4-[2-(1-pyrrolidinyl)ethoxy]benzyl]benzo[b]thiophene (Example 16; Part D) and 3-pyrazole carboxylic acid in 48% yield following radial chromatography ($SiO_2$; 1% then 3% then 5% MeOH in $CHCl_3$ sat'd with $NH_4OH$). The solid was taken up in 5 mL MeOH, and the solution was treated with 1 mL of 1 N HCl. The solution was concentrated to give the title compound.

FDMS (M+); Anal. calcd for $C_{31}H_{30}N_4O_2S \cdot 2HCl$: C, 62.51; H, 5.42; N, 9.41. Found: C, 62.40; H, 5.62; N, 9.35.

EXAMPLE 18

Preparation of 3-[4-[2-(1-Pyrrolidinyl)ethoxy]benzyl]-2-[4-(3-oxocyclopentylcarbonylamino)phenyl]benzo[b]thiophene Trifluoroacetate

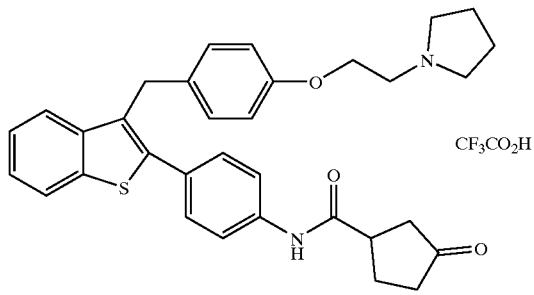

CF$_3$CO$_2$H

By essentially following the conditions described in Example 1, Part F, the free base of the title compound was prepared as a foam from 2-(4-aminophenyl)-3-[4-[2-(1-pyrrolidinyl)ethoxy]benzyl]benzo[b]thiophene (Example 16; Part D) and 3-carboxycyclopentanone in 98% yield following radial chromatography (SiO$_2$; 1% then 2% then 5% MeOH in CHCl$_3$ sat'd with NH$_4$OH). The solid was taken up in 5 mL of MeOH and was treated with 1.2 eq of CF$_3$CO$_2$H. The solution was concentrated in vacuo to give the title compound.

FDMS 539 (M+1); Anal. calcd for C$_{33}$H$_{34}$N$_2$O$_3$S.0.1CF$_3$CO$_2$H: C, 72.49; H, 6.25; N, 5.09. Found: C, 72.33; H, 6.03; N, 5.20.

EXAMPLE 19

Preparation of 3-[4-[2-(1-Pyrrolidinyl)ethoxy]benzyl]-2-[4-[1-oxo-2-(5-oxopyrrolidin-2-yl)ethyl]phenyl]-benzo[b]thiophene Oxalate

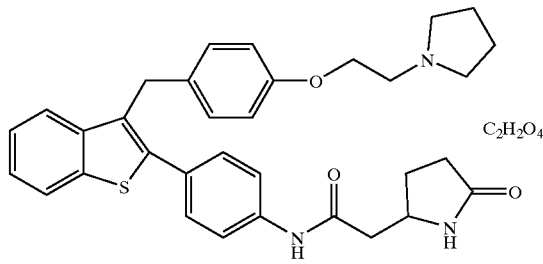

C$_2$H$_2$O$_4$

By essentially following the conditions described in Example 1, Part F, the free base of the title compound was prepared as a foam from 2-(4-aminophenyl)-3-[4-[2-(1-pyrrolidinyl)ethoxy]benzyl]benzo[b]thiophene (Example 16; Part D) and 2-pyrrolidinone-5-acetic acid in 91% yield following radial chromatography (SiO$_2$; 1% then 2% then 5% MeOH in CHCl$_3$ sat'd with NH$_4$OH). The product was converted to the oxalate salt according to the proceedure described in Example 1, Part G.

FDMS 554 (M+1); Anal. calcd for C$_{33}$H$_{34}$N$_3$O$_3$S.C$_2$H$_2$O$_4$.1.3H$_2$O: C, 63.01; H, 5.98; N, 6.30. Found: C, 63.39; H, 5.77; N, 5.91.

EXAMPLE 20

Preparation of 3-[4-[2-(1-Pyrrolidinyl)ethoxy]benzyl]-2-[4-(5-oxopyrrolidin-2-ylcarbonylamino)phenyl]benzo[b]thiophene Oxalate

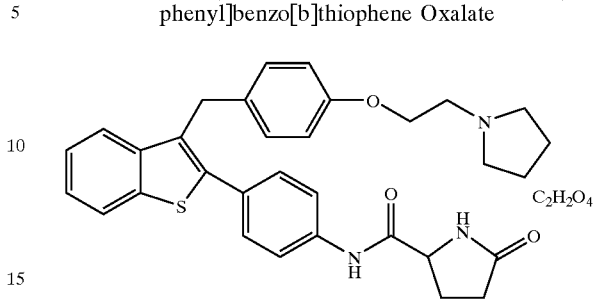

C$_2$H$_2$O$_4$

By essentially following the conditions described in Example 1, Part A, the free base of the title compound was prepared as a foam from 2-(4-aminophenyl)-3-[4-[2-(1-pyrrolidinyl)ethoxy]benzyl]benzo[b]thiophene (Example 16; Part D) and 2-pyrrolidinone-5-carboxylic acid in 51% yield following radial chromatography (SiO$_2$; 2% then 3% then 4% MeOH in CHCl$_3$ sat'd with NH$_4$OH). The product was converted to the oxalate salt according to the proceedure described in Example 1, Part G.

$^1$H NMR (CDCl$_3$; free base) δ 9.00 (s, 1H), 7.83–7.78 (m, 1H), 7.70–7.64 (m, 3H), 7.53–7.48 (m, 1H), 7.32–7.26 (m, 2H), 7.01 (d, J=8.5 Hz, 2H), 6.79 (d, J=8.5 Hz, 2H), 4.34–4.28 (m, 1H), 4.17 (s, 2H), 4.04 (t, J=6.0 Hz, 2H), 2.87 (t, J=6.0 Hz, 2H), 2.66–2.58 (m, 4H), 2.54–2.24 (m, 4H), 1.84–1.74 (m, 4H); FDMS 554 (M+1).

EXAMPLE 21

Preparation of 3-[4-[2-(1-Pyrrolidinyl)ethoxy]benzyl]-2-[4-[(1-methyl-5-oxopyrrolidin-3-ylcarbonyl)amino]phenyl]-benzo[b]thiophene Oxalate

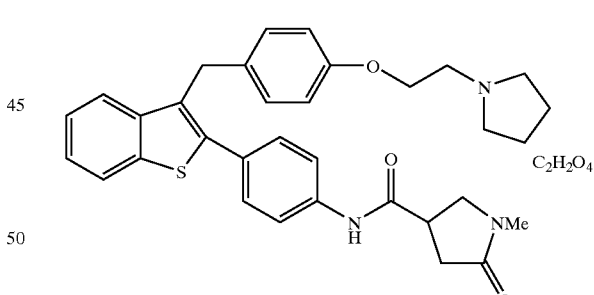

C$_2$H$_2$O$_4$

By essentially following the conditions described in Example 1, Part F, the free base of the title compound was prepared as a foam from 2-(4-aminophenyl)-3-[4-[2-(1-pyrrolidinyl)ethoxy]benzyl]benzo[b]thiophene (Example 16; Part D) and 1-methyl-2-pyrrolidinone-5-carboxylic acid in 95% yield following radial chromatography (SiO$_2$; 1% then 2% then 5% MeOH in CHCl$_3$ sat'd with NH40H). The product was converted to the oxalate salt according to the proceedure described in Example 1, Part G.

FDMS 554 (M+1); Anal. calcd for C$_{33}$H$_{34}$N$_3$O$_3$S.1.0C$_2$H$_2$O$_4$. 1.1H$_2$O: C, 63.35; H, 5.95; N, 6.33. Found: C, 63.11; H, 5.71; N, 6.01.

EXAMPLE 22

Preparation of 3-[4-[2-(1-Pyrrolidinyl)ethoxy] benzyl]-2-[4-[(2-oxoimidazolidin-4-ylcarbonyl) amino]phenyl]-benzo[b]thiophene Oxalate

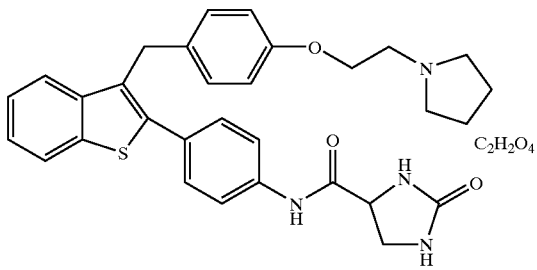

By essentially following the conditions described in Example 1, Part F, the free base of the title compound was prepared as a foam from 2-(4-aminophenyl)-3-[4-[2-(1-pyrrolidinyl)ethoxy]benzyl]benzo[b]thiophene (Example 16; Part D) and 2-imidazolidone-4-carboxylic acid in 67% yield following radial chromatography (SiO$_2$; 2% then 4% then 10% MeOH in CHCl$_3$ sat'd with NH$_4$OH). The product was converted to the oxalate salt according to the proceedure described in Example 1, Part G.

FDMS 541 (M+1); Anal. calcd for C$_{31}$H$_{32}$N$_4$O$_3$S.1.1C$_2$H$_2$O$_4$. 0.3H$_2$O: C, 61.81; H, 5.44; N, 8.68. Found: C, 61.56; H, 5.10; N, 8.98.

EXAMPLE 23

Preparation of (R)-3-[4-[2-(1-Pyrrolidinyl)ethoxy] benzyl]-2-[4-[(2-oxothiazolidin-4-ylcarbonyl)amino] phenyl]-benzo[b]thiophene Oxalate

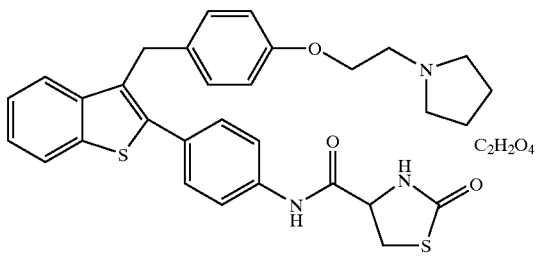

By essentially following the conditions described in Example 1, Part F, the free base of the title compound was prepared as a foam from 2-(4-aminophenyl)-3-[4-[2-(1-pyrrolidinyl)ethoxy]benzyl]benzo[b]thiophene (Example 16; Part D) and (−)-2-oxo-4-thiazolidinecarboxylic acid in 67% yield following radial chromatography (SiO$_2$; 1% then 2% then 4% MeOH in CHCl$_3$ sat'd with NH$_4$OH). The product was converted to the oxalate salt according to the proceedure described in Example 1, Part G.

FDMS 559 (M+1); Anal. calcd for C$_{31}$H$_{31}$N$_3$O$_3$S$_2$.C$_2$H$_2$O$_4$: C, 61.19; H, 5.14; N, 6.49. Found: C, 61.08; H, 5.17; N, 6.25.

EXAMPLE 24

Preparation of 3-[4-[2-(1-Pyrrolidinyl)ethoxy] benzyl]-2-[4-[1-oxo-2-(5-oxopyrrolidin-3-yl)ethyl] phenyl]benzo[b]thiophene Oxalate

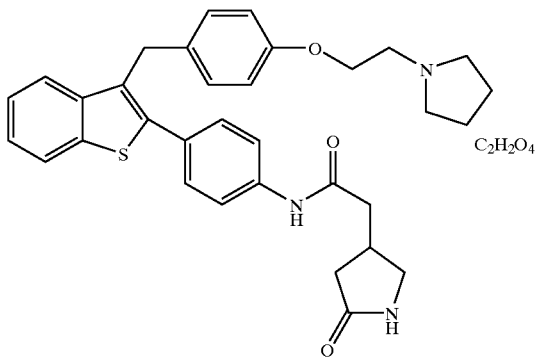

By essentially following the conditions described in Example 1, Part F, the free base of the title compound was prepared as a foam from 2-(4-aminophenyl)-3-[4-[2-(1-pyrrolidinyl)ethoxy]benzyl]benzo[b]thiophene (Example 16; Part D) and 2-pyrrolidinone-4-acetic acid in 67% yield following radial chromatography (SiO$_2$; 1% then 2% then 4% MeOH in CHCl$_3$ sat'd with NH$_4$OH). The product was converted to the oxalate salt according to the proceedure described in Example 1, Part G.

EXAMPLE 25

Preparation of 3-[4-[2-(1-Pyrrolidinyl)ethoxy] benzyl]-2-[4-(3-isoxazolylcarbonylamino)phenyl] benzo[b]thiophene Oxalate

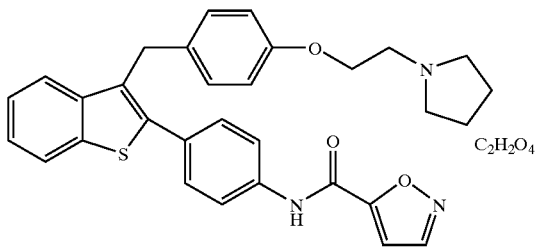

By essentially following the conditions described in Example 1, Part F, the free base of the title compound was prepared as a foam from 2-(4-aminophenyl)-3-[4-[2-(1-pyrrolidinyl)ethoxy]benzyl]benzo[b]thiophene (Example 16; Part D) and 5-isoxazolecarboxylic acid in 95% yield following radial chromatography (SiO$_2$; 1% then 2% then 3% MeOH in CHCl$_3$ sat'd with NH$_4$OH). The product was converted to the oxalate salt according to the proceedure described in Example 1, Part G.

EXAMPLE 26

Preparation of 3-[4-[2-(1-Pyrrolidinyl)ethoxy] benzyl]-2-[4-(5-isoxazolylcarbonylamino)phenyl] benzo[b]thiophene Oxalate

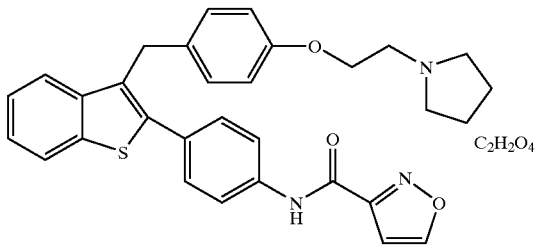

By essentially following the conditions described in Example 1, Part F, the free base of the title compound was prepared as a foam from 2-(4-aminophenyl)-3-[4-[2-(1-pyrrolidinyl)ethoxy]benzyl]benzo[b]thiophene (Example 16; Part D) and 3-isoxazolecarboxylic acid in 88% yield following radial chromatography (SiO$_2$; 1% then 2% then 3% MeOH in CHCl$_3$ sat'd with NH$_4$OH). The product was converted to the oxalate salt according to the proceedure described in Example 1, Part G.

EXAMPLE 27

Preparation of 6-Hydroxy-3-[4-[2-(1-pyrrolidinyl) ethoxy]benzyl]-2-[4-(3-cyanopropyloxy)phenyl] benzo[b]thiophene

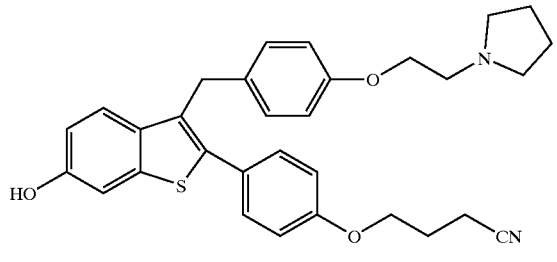

Part A. 6-Benzyloxy-2-dimethylaminobenzo[b]thiophene-3-yl 4-[2-(1-Pyrrolidinyl)ethoxy]phenyl Ketone.

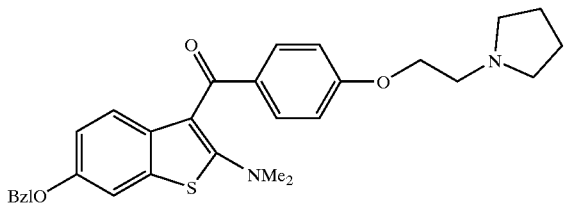

By essentially following the proceedure described in Example 16, Part A, the title compound was prepared as an oil starting from 6-benzyloxy-2-dimethylaminobenzo[b]thiophene and 4-[2-(1-pyrrolidinyl)ethoxy]benzoyl chloride hydrochloride in 38% yield following MPLC (SiO$_2$; 15% then 20% then 30% THF with 5% TEA in hexanes).

FDMS 500 (M+); Anal. calcd for C$_{30}$H$_{32}$N$_2$O$_3$S: C, 71.97; H, 6.44; N, 5.60. Found: C, 72.18; H, 6.29; N, 5.53.

Part B. 6-Benzyloxy-2-(4-triisopropylsilyloxyphenyl)benzo[b]thiophene-3-yl 4-[2-(1-Pyrrolidinyl)ethoxy]phenyl Ketone.

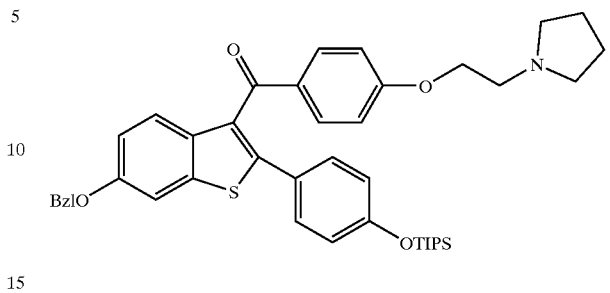

By essentially following the proceedure described in Example 16, Part C, the title compound was prepared as an oil starting from 6-benzyloxy-2-dimethylaminobenzo[b]thiophene-3-yl 4-[2-(1-pyrrolidinyl)ethoxy]phenyl ketone (Part A) and 1-bromo-4-(triisopropylsilyloxy)benzene in 57% yield following MPLC (SiO$_2$; 10% then 15% then 20% THF with 5% TEA in hexanes).

FDMS 706 (M+); Anal. calcd for C$_{43}$H$_{51}$NO$_4$S: C, 74.63; H, 7.72; N, 2.02. Found: C, 74.43; H, 7.59; N, 2.10.

Part C. 6-Benzyloxy-2-(4-hydroxy)phenylbenzo[b]thiophen-3-yl 4-[2-(1-Pyrrolidinyl)ethoxy]phenyl Ketone.

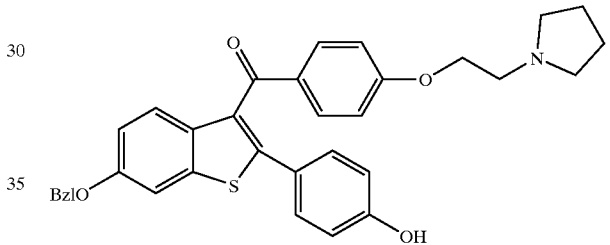

By essentially following the proceedure described in Example 14, Part D, the title compound was prepared as a foam starting from 6-benzyloxy-2-(4-triisopropylsilyloxyphenyl)benzo[b]thiophene-3-yl 4-[2-(1-pyrrolidinyl)ethoxy]phenyl ketone (Part B) in quantitative yield following MPLC (SiO$_2$; 0.5% in CHCl$_3$ sat'd with NH$_4$OH).

FDMS 550 (M+1).

Part D. 6-Benzyloxy-2-(4-hydroxyphenyl)-3-[4-[2-(1-pyrrolidinyl)ethoxy]benzyl]benzo[b]thiophene.

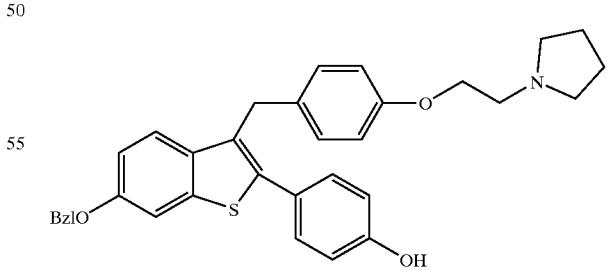

By essentially following the proceedure described in Example 3, Part A, the title compound was prepared as a foam starting from 6-benzyloxy-2-(4-hydroxy)phenylbenzo[b]thiophen-3-yl 4-[2-(1-pyrrolidinyl)ethoxy]phenyl ketone (Part C) in 52% yield following MPLC (SiO$_2$; 0.5% in CHCl$_3$ sat'd with NH$_4$OH).

FDMS 536 (M+1); Anal. calcd for $C_{34}H_{33}NO_3S$: C, 76.23; H, 6.21; N, 2.62. Found: C, 76.45; H, 6.09; N, 2.91.

Part E. 6-Benzyloxy-3-[4-[2-(1-pyrrolidinyl)ethoxy]benzyl]-2-[4-(3-cyanopropyloxy)phenyl]benzo[b]thiophene.

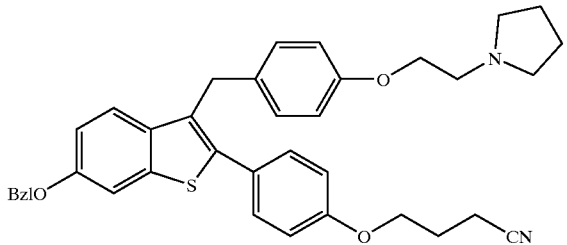

A mixture of 6-benzyloxy-2-(4-hydroxyphenyl)-3-[4-[2-(1-pyrrolidinyl)ethoxy]benzyl]benzo[b]thiophene (Part D), 4-bromobutyronitrile (1.2 mol/mol of phenol), and $Cs_2CO_3$ (2 mol/mol of phenol) in DMF (about 10 mL/mmol of phenol) was heated to 80° C. for 3 h, poured into 4 volumes of water and extracted with EtOAc. After drying ($K_2CO_3$) and evaporation, the title compound was obtained as a foam in 98% yield following MPLC ($SiO_2$; 0.5% in $CHCl_3$ sat'd with $NH_4OH$).

FDMS 603 (M+); Anal. calcd for $C_{38}H_{38}N_2O_3S$: C, 75.72; H, 6.35; N, 4.65. Found: C, 75.66; H, 6.18; N, 4.72.

Part F. 6-Hydroxy-3-[4-[2-(1-pyrrolidinyl)ethoxy]benzyl]-2-[4-(3-cyanopropyloxy)phenyl]benzo[b]thiophene.

By essentially following the proceedure described in Example 8, Part F, the title compound was prepared as an oil starting from 6-benzyloxy-3-[4-[2-(1-pyrrolidinyl)ethoxy]benzyl]-2-[4-(3-cyanopropyloxy)phenyl]benzo[b]thiophene (Part E) in 71% yield following radial chromatography ($SiO_2$; 1.0% in $CHCl_3$ sat'd with $NH_4OH$).

FDMS 513 (M+1); Anal. calcd for $C_{31}H_{32}N_2O_3S$: C, 72.63; H, 6.29; N, 5.46. Found: C, 72.87; H, 6.26; N, 5.52.

EXAMPLE 28

Preparation of (R)-3-[4-[2-(1-Pyrrolidinyl)ethoxy]benzyl]-2-[3-methyl-4-(5-oxopyrrolidin-2-ylmethoxy)phenyl]benzo[b]thiophene Oxalate

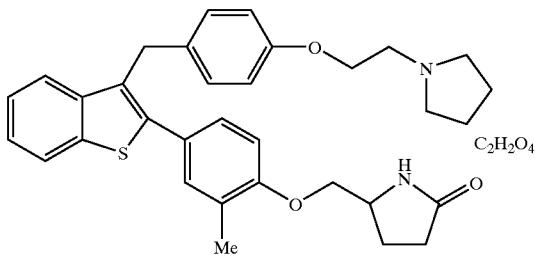

Part A. (R)-5-(4-Bromo-2-methylphenoxymethyl)-2-pyrrolidinone.

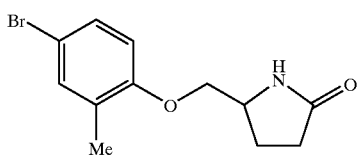

By essentially following the procedure described in Example 2, Part A, the title compound was prepared as a solid starting from 2-methyl-4-bromophenol and (R)-(–)-5-(hydroxymethyl)-2-pyrrolidinone in 83% yield following MPLC ($SiO_2$; 25% then 35% then 45% then 55% EtOAc in hexanes)

FDMS 283 and 285 (M+); Anal. calcd for $C_{12}H_{14}BrNO_2$: C, 50.72; H, 4.97; N, 4.93. Found: C, 50.66; H, 4.98; N, 4.66.

Part B. (R)-2-[3-Methyl-4-(5-oxopyrrolidin-2-ylmethoxy)phenyl]benzo[b]thiophene.

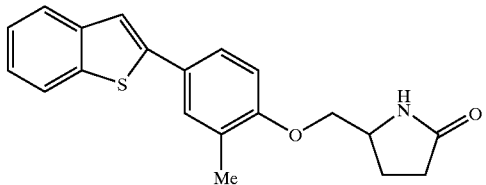

By essentially following the procedure described in Example 1, Part A, the title compound was prepared as a solid starting from benzo[b]thiophene-2-boronic acid and the bromide of Part A in 65% yield following recrystallization from EtOAc.

FDMS 337 (M+); Anal. calcd for $C_{20}H_{19}NO_2S$: C, 71.19; H, 5.67; N, 4.15. Found: C, 71.04; H, 5.79; N, 3.92.

Part C. (R)-2-[3-Methyl-4-(5-oxopyrrolidin-2-ylmethoxy)phenyl]benzo[b]thiophen-2-yl 4-[2-(1-Pyrrolidinyl)ethoxy]phenyl Ketone.

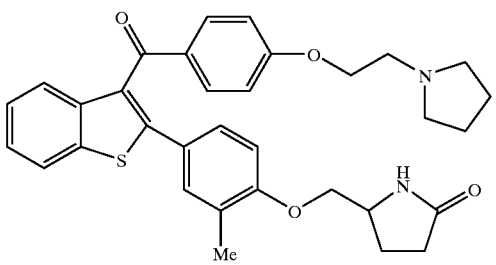

By essentially following the procedure described in Example 1, Part D, the title compound was prepared as a yellow solid starting from the above benzothiophene (Part B) and 4-[2-(1-pyrrolidinyl)ethoxy]benzoyl chloride in 74% yield following radial chromatography.

Part D. (R)-3-[4-[2-(1-Pyrrolidinyl)ethoxy]benzyl]-2-[3-methyl-4-(5-oxopyrrolidin-2-ylmethoxy)phenyl]benzo[b]thiophene Oxalate.

By essentially following the procedure described in Example 3, Part A, the free base of the title compound was prepared from the above ketone Part C) in 33% yield. The product was converted to the oxalate salt by the procedure described in Example 1, Part G.

FDMS 541 (M+1); Anal. calcd for $C_{33}H_{36}N_2O_3S \cdot C_2H_2O_4$: C, 66.65; H, 6.07; N, 4.44. Found: C, 66.36; H, 5.95; N, 4.51.

EXAMPLE 29

Preparation of 6-Hydroxy-3-[3-methyl-4-(1-pyrrolidinylmethyl)benzyl]-2-[4-(1-methyl-5-oxopyrrolidin-2-ylcarbonylamino)phenyl]benzo[b]thiophene Oxalate

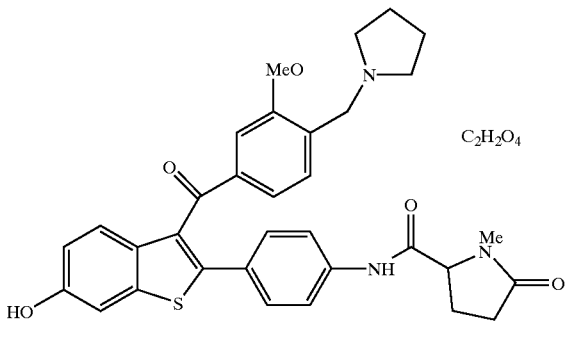

Part A. 6-Methoxy-2-[4-(1-methyl-5-oxopyrrolidin-2-ylcarbonylamino)phenyl]benzo[b]thiophen-3-yl 3-[3-Methyl-4-(1-pyrrolidinylmethyl)phenyl Ketone.

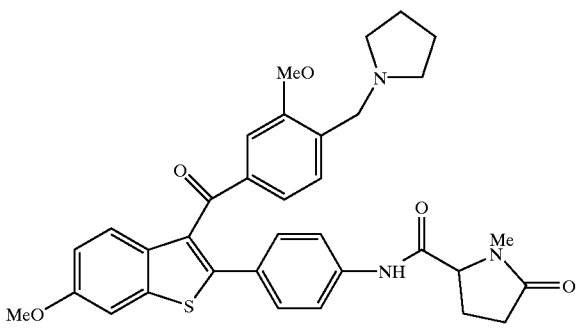

A 0° C. solution of N-methylpyroglutamic acid (621 mg; 3.29 mmol; *Bull Soc Chim Fr*, 1973, (3) (Pt. 2), 1053–6), 3-methyl-4-(1-pyrrolidinylmethyl)phenyl 6-methoxy-2-(4-aminophenyl)benzo[b]thiophen-3-yl ketone (Example 1, Part E; 1.5 g; 3.29 mmol) and 1-hydroxy-7-azabenzotriazole (448 mg; 3.29 mmol) in 50 mL of dry DMF was treated with 1,3-dicyclohexylcarbodiimide (629 mg, 3.29 mmol). The resulting mixture was allowed to gradually warm to ambient temperature. After stirring for 48 h, the reaction mixture was poured into 100 mL of saturated NaHCO$_3$. The aqueous layer was extracted with EtOAc (2×50 mL). The combined organic layers were washed with H$_2$O (2×50 mL) and brine (50 mL), dried over K$_2$CO$_3$, filtered and concentrated in vacuo. Radial chromatography (SiO2; gradient of 0.5% to 2% MeOH in CHCl$_3$, saturated with NH$_4$OH) afforded 816 mg (1.4 mmol; 43%) of the title product as a bright yellow foam.

FDMS 581 (M$^+$); *Anal. Calcd.* for C$_{34}$H$_{35}$N$_3$O$_4$S.H$_2$O: C, 68.09; H, 6.22; N, 7.01. Found: C, 67.97; H, 5.99; N, 6.97.

Part B. 6-Methoxy-3-[3-methyl-4-(1-pyrrolidinylmethyl)benzyl]-2-[4-(1-methyl-5-oxopyrrolidin-2-ylcarbonylamino)phenyl]benzo[b]thiophene.

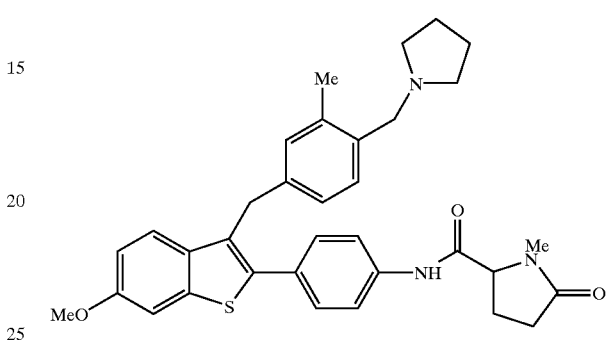

A −40° C. solution of the ketone (387 mg, 0.665 mmol) from Part A in 10 mL of THF was treated with LAH (1.3 mL, 1M in THF). After 3 h, the reaction mixture was quenched with saturated NH$_4$Cl solution (50 mL). The aqueous layer was extracted with CHCl$_3$ (3×50 mL). The combined organic layers were dried over K$_2$CO$_3$, filtered and concentrated in vacuo. The crude alcohol was purified by radial chromatography (1% to 3% MeOH in CHCl$_3$, saturated with NH$_4$OH). The resultant benzyl alcohol was dissolved in 10 mL of dichloroethane. Et$_3$SiH (0.745 mL, 4.66 mmol) was added, and the resulting mixture was cooled to 0° C. The reaction mixture was treated with TFA (0.51 mL, 6.65 mmol). After 4 h, the reaction mixture was poured into saturated NaHCO$_3$ solution (100 mL). The aqueous layer was extracted with 5% MeOH in CHCl$_3$ (3×50 mL). The combined organic layers were dried over K$_2$CO$_3$, filtered and concentrated. Purification by radial chromatography (2% MeOH in CHCl$_3$, saturated with NH$_4$OH) afforded 329 mg of the title compound (0.579 mmol; 87%). A small sample was converted to the oxalate salt according to the conditions described in Example 1, Part G.

FDMS 567 (M$^+$); Anal. Calcd. for C$_{34}$H$_{37}$N$_3$O$_3$S.C$_2$H$_2$O$_4$.1.3H$_2$O: C, 63.48; H, 6.16; N, 6.17. Found: C, 63.56; H, 6.24; N, 5.78.

Part C. 6-Hydroxy-3-[3-methyl-4-(1-pyrrolidinylmethyl)benzyl]-2-[4-(1-methyl-5-oxopyrrolidin-2-ylcarbonylamino)phenyl]benzo[b]thiophene Oxalate.

By essentially following the procedure outlined in Example 2, Part B, the title compound was prepared in 58% yield from the product of Part B above.

FDMS 553 (M$^+$); Anal. Calcd. for C$_{33}$H$_{35}$N$_3$O$_3$S.2C$_2$H$_2$O$_4$: C, 60.56; H, 5.36; N, 5.73; found: C, 60.73; H, 5.36; N, 5.80.

EXAMPLE 30

Preparation of 6-Hydroxy-3-[3-methyl-4-(1-pyrrolidinylmethyl)benzyl]-2-[4-[(methyl)(1-methyl-5-oxopyrrolidin-2-ylcarbonyl)amino]phenyl]benzo[b]thiophene Oxalate

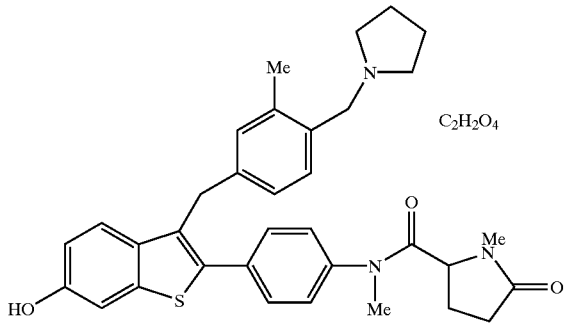

Part A. 6-Methoxy-3-[3-methyl-4-(1-pyrrolidinylmethyl) benzyl]-2-[4-[(methyl)(1-methyl-5-oxopyrrolidin-2-ylcarbonyl)amino]phenyl]benzo[b]thiophene.

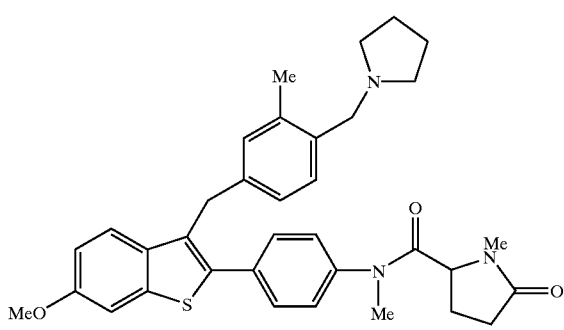

A 0° C. solution of 6-hydroxy-3-[3-methyl-4-(1-pyrrolidinylmethyl)benzyl]-2-[4-(1-methyl-5-oxopyrrolidin-2-ylcarbonylamino)phenyl]benzo[b]thiophene from Example 29, Part B (150 mg; 0.264 mmol) in 5 mL of dry DMF was treated with NaH (16 mg; 0.37 mmol). After 1 hr, methyl iodide (0.017 mL; 0.264 mmol) was quickly added via a syringe. The resulting mixture was stirred at 0° C. for 30 min, then it was allowed to warm to ambient temperature. The reaction mixture was poured into saturated aqueous NH$_4$Cl and EtOAc (25 mL each). The aqueous layer was extracted with 5% MeOH/EtOAc (2×25 mL). The combined organics were dried over K$_2$CO$_3$, filtered and concentrated in vacuo. The crude residue was purified by radial chromatography (SiO$_2$; gradient of 0.5% to 2% MeOH in CHCl$_3$, saturated with NH$_4$OH) afforded 37 mg (24%) of the title product as a yellow oil.

FAB-HRMS: m/e, calcd for C$_{35}$H$_{40}$N$_3$O$_3$S: 582.2790. Found: 582.2803 (M+1).

Part B. 6-Hydroxy-3-[3-methyl-4-(1-pyrrolidinylmethyl) benzyl]-2-[4-[(methyl)(1-methyl-5-oxopyrrolidin-2-ylcarbonyl)amino]phenyl]benzo[b]thiophene Oxalate.

The title compound was prepared from the product of Part A by essentially following the procedure outlined in Example 2, Part B.

FAB-HRMS: m/e, calcd for C$_{34}$H$_{38}$N$_3$O$_3$S: 568.2634. Found: 568.2638 (M+1).

EXAMPLE 31

Preparation of 6-Hydroxy-3-[3-methoxy-4-(1-pyrrolidinylmethyl)benzyl]-2-[4-(phenylsulfonylamino)phenyl]benzo[b]thiophene Oxalate

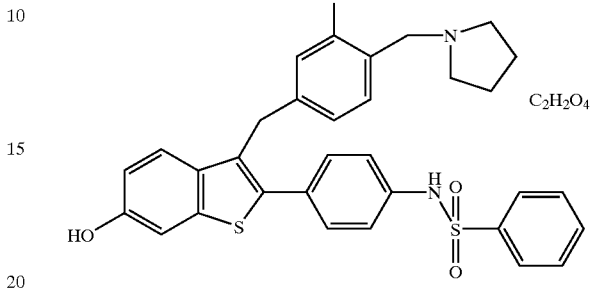

Part A. 6-Benzyloxy-2-(4-aminophenyl)benzo[b]thiophen-3-yl 3-Methoxy-4-(1-pyrrolidinylmethyl)phenyl Ketone.

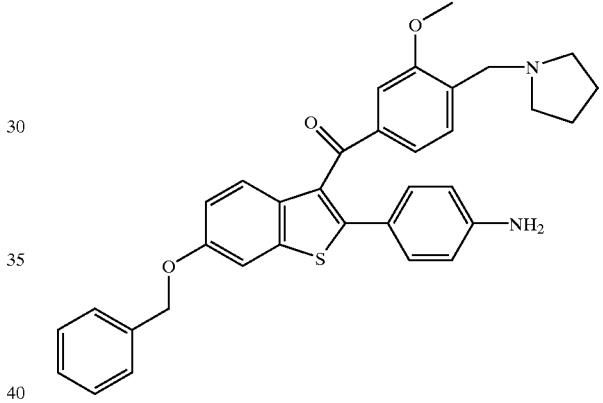

To (0.47 mL, 1.65 mmol) of 4-bromo-N,N-bis (trimethylsilyl)aniline dissolved in 3.3 mL of freshly distilled THF was added 40 mg of magnesium turnings. This mixture was heated at reflux for one hour. All the magnesium was consumed at this point. 6-Benzyloxy-2-dimethylaminobenzo[b]thiophen-3-yl 3-methoxy-4-(1-pyrrolidinylmethyl)phenyl ketone (750 mg, 1.50 mmol) was dissolved in 15 mL of dry THF and cooled to 0° C. The Grignard solution was then transferred via cannula to the ketone solution at 0° C. The reaction was allowed to slowly warm to room temperature. over a period of 2 h. The reaction was then quenched with 15 mL of satd NH$_4$Cl solution. The resulting slurry was stirred at room temperature overnight. The layers were separated and the aqueous layer was extracted with EtOAc (3×150 mL). The combined organic layers were washed with brine (1×100 mL), dried over MgSO$_4$ and concentrated under reduced pressure. Purification by flash chromatography (silica gel, 5% to 7%[10% NH$_4$OH/MeOH]/CH$_2$Cl$_2$) afforded 598 mg (1.09 mmol, 73%) of a yellow foam.

$^1$HNMR (CDCl$_3$) d 7.71 (d, J=8.9 Hz, 1H), 7.28–7.48 (m, 8H), 7.12 (d, J=8.4 Hz, 2H), 7.08 (dd, J=2.4 Hz, 9.0 Hz, 1H), 6.47 (d, J=8.4 Hz, 2H), 5.15 (s, 2H), 3.82 (br s, 2H), 3.78 (s, 3H), 2.76 (m, 4H), 1.90 (m, 4H); FDMS 548 (M$^+$);

Part B. 6-Benzyloxy-2-[4-(phenylsulfonylamino)phenyl]benzo[b]thiophen-3-yl 3-Methoxy-4-(1-pyrrolidinylmethyl)phenyl Ketone.

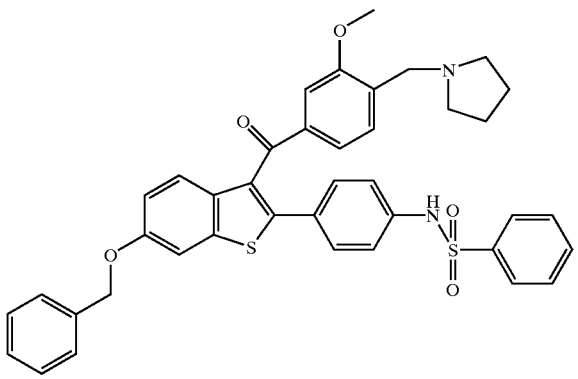

To a solution of (299 mg, 0.545 mmol) 6-benzyloxy-2-(4-aminophenyl)benzo[b]thiophen-3-yl 3-methoxy-4-(1-pyrrolidinylmethyl)phenyl ketone (Part A) in 6 mL of pyridine was added 104 mL of benzenesulfonyl chloride. The red solution was stirred at room temperature for 2 h. The reaction mixture was then concentrated to dryness under reduced pressure. The residue was taken up in 50 mL of $CH_2Cl_2$. The mixture was washed with (1×15 mL) with water and the aqueous layer was back extracted with $CH_2Cl_2$ (2×50 mL). The combined organic layers were washed with brine (1×50 mL), dried over $MgSO_4$ and concentrated under reduced pressure. Purification by flash chromatography (silica gel, 3% to 5%[10% $NH_4OH$ in $MeOH$]/$CH_2Cl_2$) afforded 301 mg (0.437 mmol, 80%) of a yellow foam.

FDMS 689 (M$^+$); Anal. Calcd for $C_{40}H_{36}N_2O_5S_2$:2.48$H_2O$: C, 68.49; H, 5.89; N, 3.99. Found: C, 68.50; H, 5.73; N, 3.65.

Part C. 6-Hydroxy-3-[3-methoxy-4-(1-pyrrolidinylmethyl)benzyl]-2-[4-(phenylsulfonylamino)phenyl]benzo[b]thiophene.

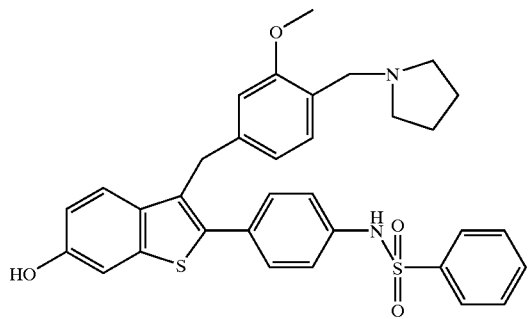

6-Benzyloxy-2-[4-(phenylsulfonylamino)phenyl]benzo[b]thiophen-3-yl 3-methoxy-4-(1-pyrrolidinylmethyl)phenyl ketone (Part B) was reduced to the corresponding benzyl compound using a procedure similar to that described in Example 3, Part A, except using LAH instead of DIBAL-H; and the benzyl protecting group was removed using a procedure similar to that described in Example 8, Part F, to afford the title compound in 85% yield.

FDMS 585 (M$^+$); Anal. calcd for $C_{35}H_{32}N_2O_4S_2$: C, 67.78; H, 5.52; N, 4.79. Found: C, 67.52; H, 5.74; N, 4.52.

Part D. 6-Hydroxy-3-[3-methoxy-4-(1-pyrrolidinylmethyl)benzyl]-2-[4-(phenylsulfonylamino)phenyl]benzo[b]thiophene Oxalate.

The title salt was prepared in 92% yield from 6-hydroxy-3-[3-methoxy-4-(1-pyrrolidinylmethyl)benzyl]-2-[4-(phenylsulfonylamino)phenyl]benzo[b]thiophene (Part C) by treating a solution in EtOAc with an excess of oxalic acid dissolved in EtOAc. The resulting solid was filtered, dried and characterized.

mp 150° C. (dec.); FDMS 584 (M$^+$); Anal. calcd for $C_{35}H_{32}N_2O_4S_2$·0.80$C_2H_2O_4$·0.20$C_4H_8O_2$: C, 63.05; H, 5.26; N, 4.15. Found: C, 63.20, H, 5.64; N, 3.90.

EXAMPLE 32

Preparation of 6-Hydroxy-2-[4-(phenylsulfonylamino)phenyl)benzo[b]thiophen-3-yl 3-Methoxy-4-(1-pyrrolidinylmethyl)phenyl Ketone Oxalate

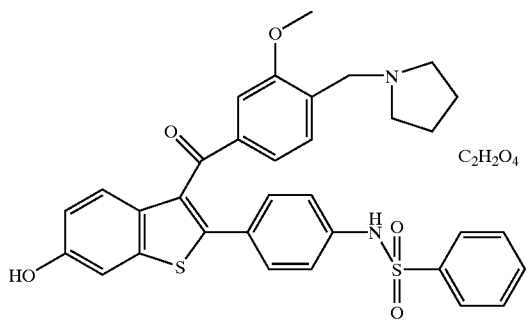

The benzyl protecting group was removed from 6-benzyloxy-2-[4-(phenylsulfonylamino)phenyl]benzo[b]thiophen-3-yl 3-methoxy-4-(1-pyrrolidinylmethyl)phenyl ketone (Example 31, Part B) using a procedure similar to that described in Example 8, Part F; and the oxalate was formed using a procedure similar to that of Example 31, Part D, to afford the title salt in 58% yield.

mp 180° C. (dec.); FDMS 598 (M$^+$); Anal. calcd for $C_{33}H_{30}N_2O_5S_2$·0.72$C_2H_2O_4$: C, 62.34; H, 4.78; N, 4.22. Found: C, 62.32; H, 5.08; N, 4.12.

EXAMPLE 33

Preparation of 2-[4-(2-Acetylaminoethyl)phenyl]-6-hydroxy-3-[3-methoxy-4-[(1-pyrrolidinyl)methyl]benzyl]benzo[b]thiophene Oxalate

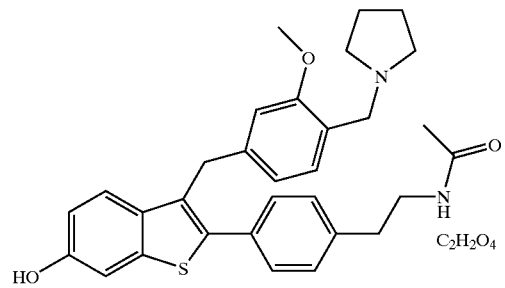

Part A. 6-Benzyloxy-2-dimethylaminobenzo[b]thiophen-3-yl 3-Methoxy-4-(1-pyrrolidinyl)methyl]phenyl Ketone. Following essentially the procedure of Example 8,

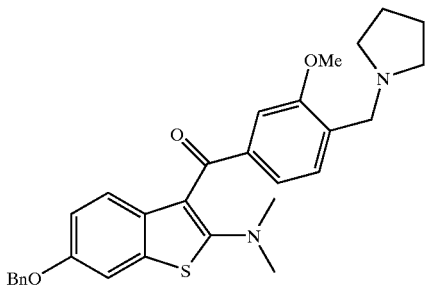

Following essentially the procedure of Example 8, Part I, the title compound was prepared from 3-methoxy-4-[(1-pyrrolidinyl)methyl]benzoic acid hydrochloride and 6-benzyloxy-2-dimethylaminobenzo[b]thiophene (Example 8, Part H) in 80% yield.

$^1$H NMR (CDCl$_3$) δ 7.45–7.32 (m, 9H), 7.19 (s, 1H), 6.88 (d, J=8.9, 1H), 5.08 (s, 2H), 3.88 (s, 3H), 3.73 (s, 2H), 2.89 (s, 6H), 2.60 (br s, 4H), 1.81 (br s, 4H). FDMS 500.0 (M).

Part B. 2-[4-(2-Aminoethyl)phenyl]-6-benzyloxybenzo[b]thiophen-3-yl 3-Methoxy-4-[(1-pyrrolidinyl)methyl]phenyl Ketone.

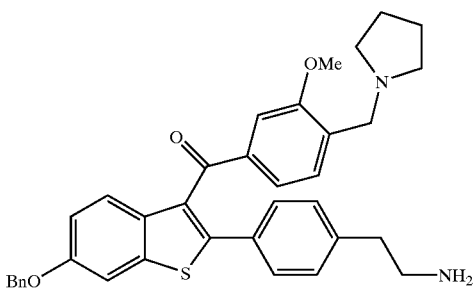

4-(2-Aminoethyl)bromobenzene (1.7 g; 8.4 mmol) and 2.3 mL (2 eq) of Et$_3$N were combined with 3 mL of anhydrous DMF in a flame-dried, argon-filled flask. 1,2-Bis(chlorodimethylsilyl)ethane was added in 3.0 mL of DMF. The mixture was stirred at room temperature for 2 h. The mixture was filtered through a sintered glass funnel, and concentrated under reduced pressure. The colorless oil subsequently crystallized.

The protected bromobenzene derivative was converted to the corresponding Grignard reagent. Magnesium (33 mg; 1.35 mmol) was placed in a flask which was subsequently flame-dried and filled with argon. Anhydrous THF (3 mL) and the protected aminoarylbromide were added with a small crystal of I$_2$. The mixture was heated under reflux for 3 h. The resulting reagent was used without purification.

The above aminobenzothiophene (Part A) (4.10 g; 8.2 mmol) was dissolved in anhydrous THF in a flame-dried, argon-filled flask, and cooled in an ice-water bath. The Grignard reagent prepared above (1.5 eq) was added dropwise. The mixture was stirred in the cold for 1 h, then saturated NH$_4$Cl was added, and extraction was carried out with CH$_2$Cl$_2$. The combined organics were dried by passage through Na$_2$SO$_4$. The product (4.2 g of yellow oil; 89% yield) was purified by flash chromatography on silica gel, eluting with a gradient of EtOAc(100–85%)/Et$_3$N(0–5%)/NH$_4$OH(0–5%).

$^1$H NMR (CDCl$_3$) δ 7.63 (d, J=8.9 Hz, 1H), 7.5–7.2 (m, 11H), 7.05 (m, 3H), 5.16 (s, 2H), 3.79 (s, 3H), 3.61 (s, 2H), 2.89 (t, J=6.6 Hz, 2H), 2.67 (t, J=6.7 Hz, 2H), 2.50 (br s, 4H), 1.77 (br s, 4H), 1.40 (br s, 2H). FDMS 577.1 (M+1).

Part C. 2-[4-(2-Aminoethyl)phenyl]-6-benzyloxy-3-[3-methoxy-4-[(1-pyrrolidinyl)methyl]benzyl]benzo[b]thiophene.

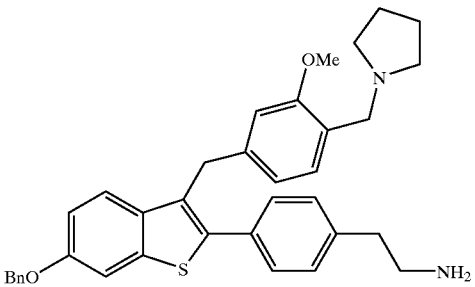

Using a procedure similar to that described in Example 1, Part G, (except using EtOAc instead of CH$_2$Cl$_2$ in the final work up), the above ketone (Part B) was reduced to the title compound compound in 59% yield. Purification was carried out by flash chromatography on silica gel, eluting with a gradient of EtOAc(100–85%)/MeOH(0–10%)/NH$_4$OH (0–5%).

$^1$H NMR (CDCl$_3$) δ 7.47–7.33 (m, 9H), 7.23 (m, 3H), 6.98 (d, J=8.7 Hz, 1H), 6.69 (d, J=7.6 Hz, 1H), 6.65 (s, 1H), 5.13 (s, 2H), 4.23 (s, 2H), 3.69 (s, 3H), 3.63 (s, 2H), 2.98 (t, J=6.8 Hz, 2H), 2.77 (t, J=6.8 Hz, 2H), 2.57 (br s, 4H), 1.79 (br s, 4H). FDMS 563.1 (M+1).

Part D. 2-[4-(2-Acetylaminoethyl)phenyl]-6-benzyloxy-3-[3-methoxy-4-[(1-pyrrolidinyl)methyl]benzyl]benzo[b]thiophene.

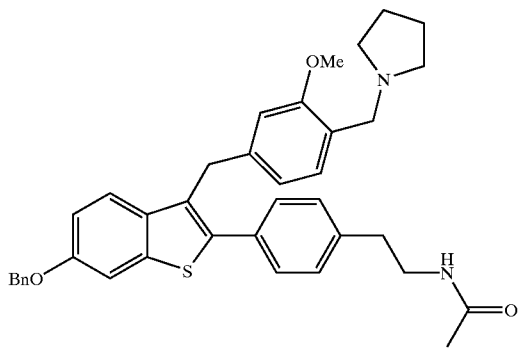

The above amine (Part C) (0.11 g; 0.20 mmol) was dissolved in 5 mL of acetic anhydride, and stirred at room temperature for 45 min. Water was added, and extraction was carried out with CH$_2$Cl$_2$. The combined organics were washed with brine and dried by passage through Na$_2$SO$_4$. The title compound (44 mg; 37% yield) was isolated by flash chromatography on silica gel, eluting with a gradient of EtOAc(100–95%)/Et$_3$N(0–5%).

$^1$H NMR (CDCl$_3$) δ 7.6–7.3 (m, 9H), 7.25 (m, 3H), 7.00 (d, J=8.6 Hz, 1H), 6.71 (d, J=7.5 Hz, 1H), 6.68 (s, 1H), 5.55 (br s, 1H), 5.10 (s, 2H), 4.25 (s, 2H), 3.70 (br s, 5H), 3.54 (q, J=6.6 Hz, 2H), 2.86 (t, J=6.7 Hz, 2H), 2.63 (br s, 4H), 1.96 (s, 3H), 1.80 (br s, 4H); FDMS 605.3 (M+1).

Part E. 2-[4-(2-Acetylaminoethyl)phenyl]-6-hydroxy-3-[3-methoxy-4-[(1-pyrrolidinyl)methyl]benzyl]benzo[b]thiophene Oxalate.

By essentially following the procedure of Example 9, Part F, except drying the CH$_2$Cl$_2$ solution with MgSO$_4$ and using flash chromatography, the title compound was obtained from its benzyl ether (Part D) in 67% yield. Conversion to the oxalate was effected by dissolving the free base in EtOAc and adding a solution of oxalic acid in EtOAc. The resultant slurry was centrifuged, the supernatant was decanted, fresh EtOAc was added, and the process was repeated twice more. The solid product was dried in vacuo overnight.

$^1$H NMR (MeOH-d$_4$) δ 7.4–7.3 (m, 3H), 7.3–7.1 (m, 4H), 6.8–6.7 (m, 2H), 6.68 (d, J=7.2, 1H), 4.21 (s, 2H), 3.98 (s, 2H), 3.71 (s, 3H), 3.38 (t, J=7.1, 2H), 2.96 (br s, 4H), 2.79 (t, J=7.5, 2H), 1.90 (br s, 7); FDMS 515 (M+1).

The 3-methoxy-4-[(1-pyrrolidinyl)methyl]benzoic acid hydrochloride for Part A, above may be obtained from the methyl ester using a procedure similar to that described above in Example 1, Part K. The ester may be obtained as follows.

Part F. Methyl 4-Bromomethyl-3-methoxybenzoate.

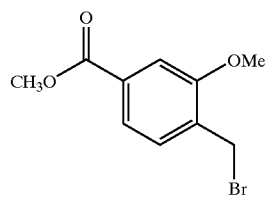

Methyl 3-methoxy-4-methylbenzoate (9.95 g; 55.2 mmol) and 10.81 g (60.7 mmol) of NBS were combined in 250 mL of CCl$_4$ and heated to reflux. AIBN (0.75 g; 5.5 mmol) was added and the resultant mixture was heated at reflux for 8 h. The mixture was refrigerated, then filtered and concentrated under reduced pressure. The residue was triturated with hexanes and filtered to give the title compound as white needles (11.7 g; 82% yield).

$^1$H NMR (CDCl$_3$) δ 7.63 (d, J=7.6 Hz, 1H), 7.58 (s, 1H), 7.41 (d, J=7.9 Hz, 1H), 4.56 (s, 2H), 3.98 (s, 3H), 3.94 (s, 3H); FDMS 528 (M+).

Part G. Methyl 3-Methoxy-4-[(1-pyrrolidinyl)methyl]benzoate.

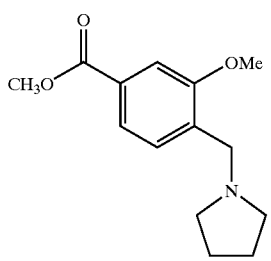

Methyl 4-bromomethyl-3-methoxybenzoate (1.0 g; 3.9 mmol) (Part F) was dissolved in THF (10 mL) and pyrrolidine (1.3 mL; 15.4 mmol) was added at room temperature. The mixture was stirred overnight at room temperature, then poured into 50 mL of water. Extraction was carried out with EtOAc (4×25 mL). The combined organics were washed with brine and dried by passage through sodium sulfate. The title compound was isolated (0.92 g; 96% yield) by flash chromatography on silica gel eluting with EtOAc (100–95%)/Et$_3$N(0–5%).

$^1$H NMR (CDCl$_3$) δ 7.62 (d, J=7.8 Hz, 1H), 7.51 (s, 1H), 7.43 (d, J=7.7 Hz, 1H), 3.90 (s, 3H), 3.87 (s, 3H), 3.69 (s, 2H), 2.57 (m, 4H), 1.79 (m, 4H).

EXAMPLE 34

Preparation of 2-[4-(3-Cyanopropyloxy)phenyl]-3-[4-[2-(1-pyrrolidinyl)ethoxy]benzyl]benzo[b]thiophene Oxalate

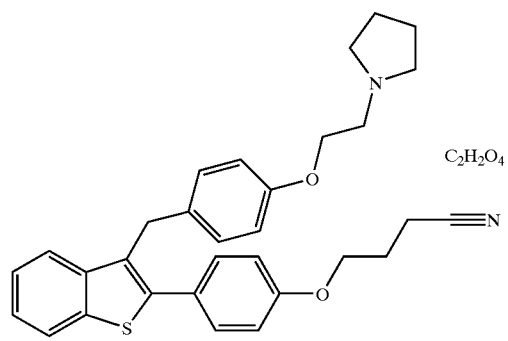

Part A. 2-(4-Methoxyphenyl)benzo[b]thiophen-3-yl 4-[2-(1-Pyrrolidinyl)ethoxy]phenyl Ketone.

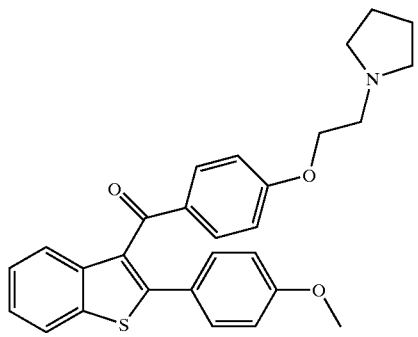

Sodium hydride (0.69 g of 60% NaH in mineral oil; 17.22 mMol) was suspended in 15 mL of dry DMF in a flame-dried, argon-filled flask. After stirring for 15 min, a solution of 4-(1-pyrrolidinyl)ethanol was added. After stirring for 15 min and gas evolution had ceased, 4-fluorophenyl 2-(4-methoxyphenyl)benzo[b]thiophen-3-yl ketone [prepared by acylation of 2-(4-methoxyphenyl)benzo[b]thiophene (Example 3, Part C) with 4-fluorobenzoyl chloride] (5.2 g; 14.34 mmol) in 15 mL of dry DMF was added. The mixture was stirred at room temperature for 5 h, then poured into 25 mL of water. Extraction was carried out with EtOAc (4×25 mL). The combined organics were washed with brine and dried by passage through sodium sulfate. The title compound (5.12 g; 78% yield) was isolated as a colorless oil by flash chromatography on silica gel, eluting with a gradient of EtOAc(100–85%)/Et$_3$N(0–5%)/MeOH(0–10%).

$^1$NMR (CDCl$_3$) δ 7.85 (m, 1H), 7.76 (d, J=6.3, 2H), 7.63 (m, 1H), 7.36 (m, 4H), 6.77 (d, J=7.2, 4H), 4.22 (t, J=5.3, 2H), 3.75 (s, 3H), 3.04 (t, J=5.2, 2H), 2.83 (br s, 4H), 1.90 (br s, 4H); FDMS 457 (M).

Part B. 2-(4-Methoxyphenyl)-3-[4-[2-(1-pyrrolidinyl)ethoxy]benzyl]benzo[b]thiophene.

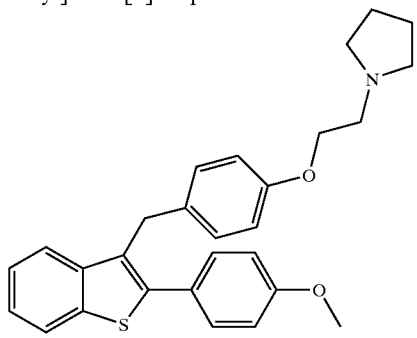

To the above ketone (Part A) (3.12 g; 11.2 mmol) in 40.0 mL of THF was added 0.42 g (11.2 mmol) of LAH at 0° C. The bath was removed and the mixture was stirred for 1 h. Hydrolysis was effected by addition of 0.42 mL of water, 0.42 mL of 5N NaOH, and 1.26 mL of water, followed by stirring for 1 h. After the mixture was filtered and washed with THF, the filtrate was concentrated; and the intermediate carbinol was dried in vacuo for 25 min. The carbinol was dissolved in methylene chloride (40.0 mL) under argon atmosphere and cooled in an ice-water bath. Triethylsilane (12.5 mL; 78.3 mmol) was added, followed by dropwise addition of 8.6 mL (112.0 mmol) of TFA. Upon completion of addition of TFA, the bath was removed and stirring was continued for 2 h. Saturated aqueous sodium bicarbonate (50 mL) was added, and extraction was carried out with EtOAc. The combined organics were washed with brine and dried by passage through sodium sulfate. The title compound (4.45 g; 90% yield) was isolated as a colorless oil by flash chromatography on silica gel, eluting with a gradient of EtOAc (100–95%)/Et$_3$N(0–5%).

$^1$NMR (CDCl$_3$) δ 7.87 (m, 1H), 7.77 (d, J=6.4, 2H), 7.65 (m, 1H), 7.34 (m, 4H), 6.78 (d, J=7.4, 4H), 4.20 (s, 2H), 4.15 (t, J=5.3, 2H), 3.73 (s, 3H), 3.14 (t, J=5.4, 2H), 2.91 (br s, 4H), 1.90 (br s, 4H); FDMS 444 (M+1).

Part C. 2-(4-Hydroxyphenyl)-3-[4-[2-(1-pyrrolidinyl)ethoxy]benzyl]benzo[b]thiophene.

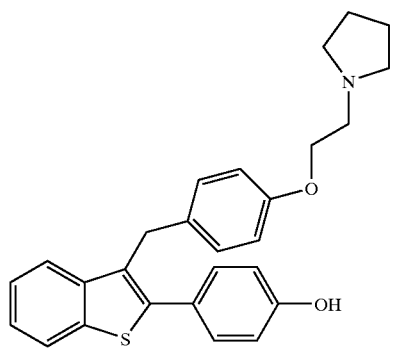

The above methyl ether (4.5 g; 10.1 mmol) (Part B) was dissolved in 45 mL of dichloroethane under an argon atmosphere and cooled in an ice-water bath. To this was added ethanethiol (6.0 mL; 81.1 mmol) and 5.41 g (40.6 mmol) of aluminum chloride, and the mixture was stirred in the cold bath for 1 h. Saturated NaHCO$_3$ was added, and stirring was continued while warming to room temperature for 1 h. The title compound (0.23 g; 74% yield) was isolated by filtration and washed with water.

$^1$NMR (CDCl$_3$) δ 7.83 (m, 1H), 7.47 (m, 1H), 7.29 (m, 2H), 6.98 (d, J=8.5, 2H), 6.83 (m, 4H), 6.69 (d, J=8.6, 2H), 4.15 (m, 4H), 3.05 (m, 2), 2.85 (br s, 4H), 1.91 (br s, 4H); FDMS 430 (M+1).

Part D. 2-[4-(3-Cyanopropyloxy)phenyl]-3-[4-[2-(1-pyrrolidinyl)ethoxy]benzyl]benzo[b]thiophene Oxalate.

Using a procedure similar to that of Example 27, Part E, the title compound was prepared from the above phenol (Part C) and 4-chlorobutyronitrile in 79% yield. Purification was effected by flash chromatography on silica gel eluting with a gradient of EtOAc(100–94%)/Et$_3$N(0–5%)/MeOH (0–2%). Conversion to the oxalate was effected essentially by the method of Example 33, Part E.

Anal. calc'd for C$_{31}$H$_{32}$N$_2$O$_2$S.C$_2$H$_2$O$_4$: C, 67.56; H, 5.84; N, 4.77. Found: C, 67.17; H, 5.86; N, 4.39; FDMS 496.0 (M for free base).

EXAMPLE 35

Preparation of 2-[4-(4-Amino-4-oxobutyloxy)phenyl]-3-[4-[2-(1-pyrrolidinyl)ethoxy]benzyl]benzo[b]thiophene Hydrochloride

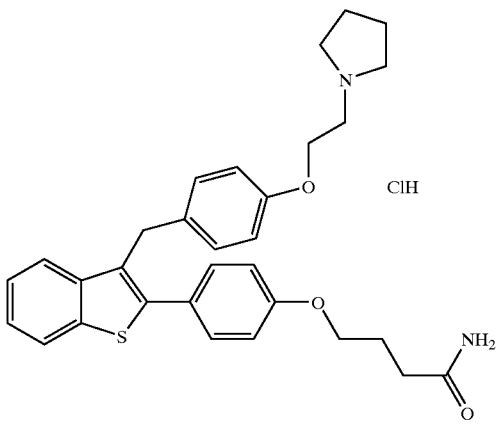

The free base of the above nitrile (Example 34, Part D) (0.15 g; 0.3 mmol) was combined with 7 mL of conc HCl and stirred at room temperature for 3 days. The mixture was concentrated under reduced pressure, and the product (0.16 g; 100% yield) was dried in vacuo overnight.

Anal. calc'd for C$_{31}$H$_{34}$N$_2$O$_3$S.HCl.4H$_2$O: C, 59.75; H, 6.95; N, 4.50. Found: C, 59.78; H, 6.46; N, 4.27. FDMS 515 (M+1 for free base).

EXAMPLE 36

Preparation of 2-[4-(2-Amino-2-oxoethoxy)phenyl]-6-hydroxy-3-[3-methoxy-4-[(1-pyrrolidinyl)methyl]benzyl]benzo[b]thiophene

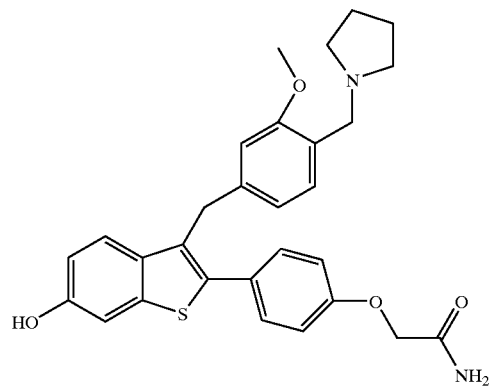

73

Part A. 4-Bromophenyl Triisopropylsilyl Ether.

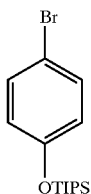

To 4-bromophenol (6.1 g, 35 mmol) and imidazole (2.6 g) in DMF (30 mL) at ambient temperature was added slowly triisopropylsilyl trifluoromethanesulfonate (10.5 mL) while stirring. The resulting mixture was stirred at ambient temperature for 1 h before dilution with water (200 mL) and extraction with EtOAc (100 mL×3). The combined organic layers were dried with sodium sulfate and concentrated under reduced pressure. Chromatography with EtOAc-hexanes (0–5% gradient elusion) afforded the product as a colorless oil (11.2 g, 96%).

$^1$H NMR (CDCl$_3$): δ 7.32 (d, J=9.1 Hz, 2H), 6.77 (d, J=9.1 Hz, 2H), 1.23 (m, 3H), 1.10 (d, J=7.0 Hz, 18H); FDMS m/e: 330 (M+H$^+$).

Part B. 6-Benzyloxy-2-[4-hydroxyphenyl]benzo[b]thiophen-3-yl 3-Methoxy-4-[(1-pyrrolidinyl)methyl]phenyl Ketone.

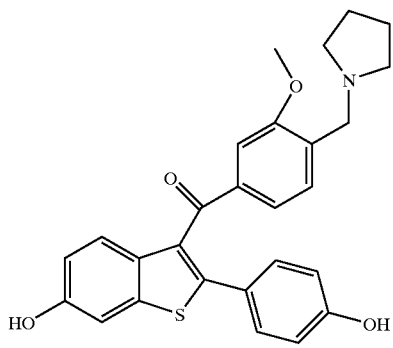

Magnesium turnings (0.24 g) were placed in a two-neck 100 mL round-bottom flask fitted with a reflux condenser and a magnetic stir bar. The whole apparatus was flame-dried and allowed to cool to ambient temperature. Dry THF (17 mL) and a small crystal of iodine were then introduced followed by slow addition of 4-bromophenyl triisopropyl-silyl ether (3.5 g) while stirring at ambient temperature. The reaction mixture was warmed to a gentle reflux for 1 h or until the magnesium turnings were completely consumed to give a 0.5 M solution of the Grignard reagent. This freshly prepared Grignard solution (15 mL) was added slowly to a stirring solution of 6-benzyloxy-2-(dimethylamino)benzo[b]thiophen-3-yl 3-methoxy-4-[(1-pyrrolidinyl)methyl]phenyl ketone (2.5 g, 5.0 mmol) in THF (15.0 mL) at 0° C. under argon. The mixture was stirred at 0° C. for 2 h before quenching with saturated aqueous NH$_4$Cl solution (50 mL) and extraction with CH$_2$Cl$_2$ (50 mL×3). The combined organic layers were dried with sodium sulfate and concentrated under reduced pressure. Chromatography with EtOAc afforded a oily brown material as the major fraction. This material was dissolved in THF (25 mL), treated with a solution of tetrabutylammonium fluoride (1.0 M in THF, 6 mL) at ambient temperature for 1 h, and then concentrated under reduced pressure. Chromatography with Et$_3$N:MeOH:EtOAc (5:10:85) afforded the title compound as a yellow foam (2.75 g, 100%).

$^1$H NMR (CDCl$_3$): δ 7.75 (d, 1H), 7.52–7.30 (m, 6H), 7.20 (d, 2H), 7.20–7.08 (m, 4H), 6.60 (d, 2H), 5.18 (s, 2H), 3.70 (s, 5H), 2.68 (m, 4H), 1.85 (m, 4H).

74

Part C. 6-Benzyloxy-2-(4-hydroxyphenyl)-3-[3-methoxy-4-[(1-pyrrolidinyl)methyl]benzyl]benzo[b]thiophene.

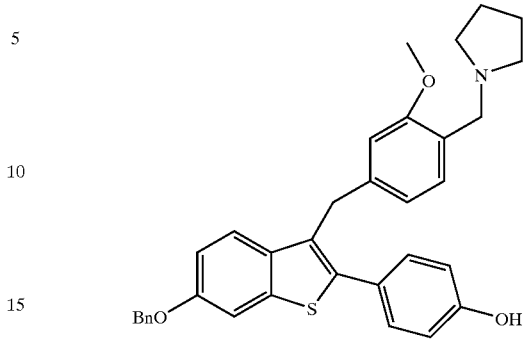

6-Benzyloxy-2-(4-hydroxyphenyl)benzo[b]thiophen-3-yl 3-methoxy-4-[(1-pyrrolidinyl)methyl]phenyl ketone (2.75 g, 5.0 mmol) in THF (25 mL) was treated with lithium aluminum hydride (420 mg) at 0° C. for 2 h, then quenched with water (1 mL) and sodium hydroxide (1.0 M, 3 mL). Stirring was continued for 45 min. The reaction mixture was diluted with brine (100 mL) and extracted with dichloromethane (100 mL×3). The combined organic layers were dried with sodium sulfate and concentrated in vacuo to give a white foam-like material. This material was dissolved in dichloromethane (50 mL), treated with triethylsilane (6.0 mL) and trifluoroacetic acid (5.0 mL) at 0° C. for 2 h, and concentrated under reduced pressure. The residue was extracted with dichloromethane (100 mL×3) which was washed with saturated aqueous sodium bicarbonate (100 mL). The combined organic layers were dried with sodium sulfate and concentrated. Chromatography with Et$_3$N:MeOH:EtOAc (5:5:90) afforded the product as a white solid (2.1 g, 78%).

$^1$H NMR (CDCl$_3$): δ 7.50–7.27 (m, 9H), 7.15 (d, 1H), 6.96 (d, 1H), 6.69 (d, 2H), 6.65 (d, 1H), 6.55 (s, 1H), 5.12 (s, 2H), 4.18 (s, 2H), 3.71 (s, 2H), 3.57 (s, 3H), 2.70 (m, 4H), 1.83 (m, 4H); FDMS m/e: 536 (M+H$^+$).

Part D. 2-[4-(2-Amino-2-oxoethoxy)phenyl]-6-benzyloxy-3-[3-methoxy-4-[(1-pyrrolidinyl)methyl]benzyl]benzo[b]thiophene.

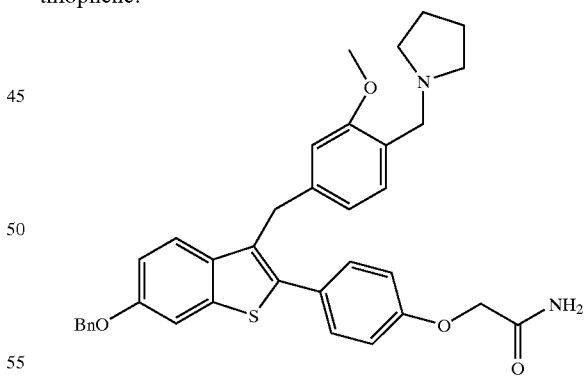

A suspension of 6-benzyloxy-2-(4-hydroxyphenyl)-3-[3-methoxy-4-[(1-pyrrolidinyl)methyl]benzyl]benzo[b]thiophene (154 mg, 0.29 mmol) and cesium carbonate (536 mg) in DMF (4 mL) was treated with 2-chloroacetamide (106 mg) at ambient temperature then heated at 90° C. under nitrogen for 2 h. The cooled reaction mixture was diluted with brine (50 mL) and extracted with EtOAc (30 mL×3). The combined organic layers were dried with sodium sulfate and concentrated under reduced pressure. Chromatography with Et$_3$N:MeOH:EtOAc (5:10:85) afforded the product (93 mg, 54%).

¹H NMR (CDCl₃): δ 7.60–7.27 (m, 9H), 7.20 (d, 1H), 7.02 (d, 1H), 6.95 (d, 2H), 6.70 (d, 1H), 6.65 (s, 1H), 6.55 (bs, 1H), 5.90 (bs, 1H), 5.12 (s, 2H), 4.52 (s, 2H), 4.23 (s, 2H), 3.70 (s, 3H), 3.63 (s, 2H), 2.62 (m, 4H), 1.80 (m, 4H).

Part E. 2-[4-(2-Amino-2-oxoethoxy)phenyl]-6-hydroxy-3-[3-methoxy-4-[(1-pyrrolidinyl)methyl]benzyl]benzo[b]thiophene.

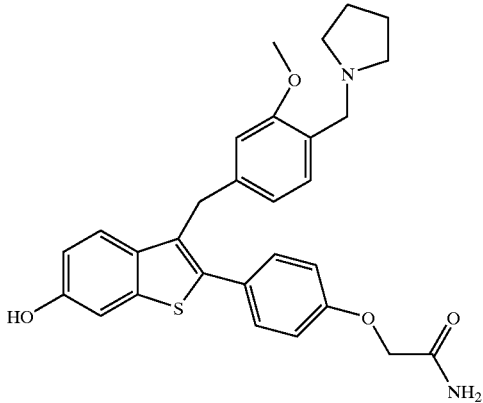

2-[4-(2-Amino-2-oxoethoxy)phenyl]-6-benzyloxy-3-[3-methoxy-4-[(1-pyrrolidinyl)methyl]benzyl]benzo[b]thiophene (90 mg) in THF (5.0 mL) was treated with a solution of ammonium formate (25% in H₂O, 2.0 mL) and 10% palladium on carbon (100 mg) sequentially at ambient temperature. The resulting mixture was stirred at ambient temperature under argon for 24 h before filtered through diatomaceous earth followed by rinsing with dichloromethane and methanol. The filtrate was extracted with dichloromethane (20 mL×3) from water (30 mL). The combined organic layers were dried with sodium sulfate and concentrated under reduced pressure. Chromatography with Et₃N:MeOH:EtOAc (5:10:85) afforded the product as a white solid (30 mg).

FDMS m/e: found 503 (M+H⁺); ¹H NMR (CDCl₃): δ 7.51 (d, 2H), 7.39 (s, 1H), 7.27 (d, 2H), 7.19 (s, 1H), 7.03 (d, 2H), 6.74 (d, 1H), 6.70 (s, 1H), 6.67 (bs, 1H), 6.49 (d, 1H), 5.88 (bs, 1H), 4.61 (s, 2H), 4.27 (s, 2H), 3.80 (s, 2H), 3.60 (s, 3H), 2.80 (m, 4H), 1.90 (m, 4H).

EXAMPLE 37

Preparation of 6-Hydroxy-3-[3-methoxy-4-(1-pyrrolidinyl)benzyl]-2-[4-[2-methylamino-2-oxoethoxyl]phenyl]benzo[b]thiophene

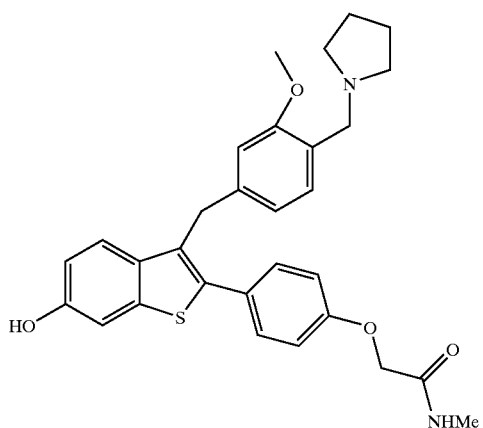

A suspension of 6-benzyloxy-2-(4-hydroxyphenyl)-3-[3-methoxy-4-[(1-pyrrolidinyl)methyl]benzyl]benzo[b]thiophene (140 mg) and cesium carbonate (500 mg) in DMF (5.0 mL) was treated with 2-chloro-N-methylacetamide (100 mg) at ambient temperature and allowed to stir at 90° C. under nitrogen for 4 h. Cooled reaction mixture was diluted with brine (50 mL) and extracted with EtOAc (30 mL×3). The combined organic layers were dried with sodium sulfate and concentrated under reduced pressure. The residue was desolved in THF (5.0 mL) and treated with a solution of ammonium formate (25% in H₂O, 2.0 mL) and 10% palladium on carbon (100 mg) sequentially at ambient temperature. The resulting mixture was stirred at ambient temperature under argon for 1 h before filtered through diaatomaceous earth followed by rinsing with dichloromethane and methanol. The filtrate was extracted with dichloromethane (20 mL×3) from water (30 mL). The combined organic layers were dried with sodium sulfate and concentrated under reduced pressure. Chromatography with Et₃N:MeOH:EtOAc (5:10:85) afforded the product (84 mg).

FDMS m/e: found 517 (M+H⁺); ¹H NMR (CDCl₃): δ 7.41 (d, 2H), 7.18 (d, 2H), 7.12 (s, 1H), 6.91 (d, 2H), 6.64 (d, 1H), 6.60 (s, 1H), 6.40 (d, 1H), 4.51 (s, 2H), 4.18 (s, 2H), 3.71 (bs, 2H), 3.51 (s, 3H), 2.93 (d, 3H), 2.69 (m, 4H), 1.82 (m, 4H).

EXAMPLE 38

Preparation of 6-hydroxy-3-[3-methoxy-4-(1-pyrrolidinyl)benzyl]-2-[4-[2-dimethylamino-2-oxoethoxy]phenyl]benzo[b]thiophene

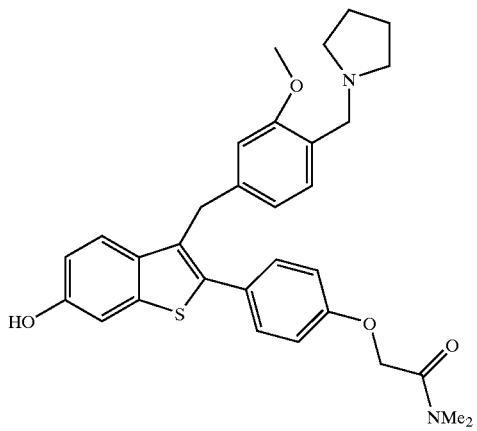

A suspension of 6-benzyloxy-2-(4-hydroxyphenyl)-3-[3-methoxy-4-[(1-pyrrolidinyl)methyl]benzyl]benzo[b]thiophene (52 mg) and cesium carbonate (150 mg) in DMF (2.0 mL) was treated with 2-chloro-N,N-dimethylacetamide (11 μL) and allowed to stir at ambient temperature under nitrogen for 1 h. The reaction mixture was diluted with brine (50 mL) and extracted with EtOAc (30 mL×3). The combined organic layers were dried with sodium sulfate and concentrated under reduced pressure. The residue was dissolved in THF (4.0 mL) and treated with a solution of ammonium formate (25% in H₂O, 2.0 mL) and 10% palladium on carbon (100 mg) sequentially at ambient temperature. The resulting mixture was stirred at ambient temperature under argon for 1 h before filtered through diatomaceous earth followed by rinsing with dichloromethane and methanol. The filtrate was extracted with dichloromethane (20 mL×3) from water (30 mL). The combined organic layers were dried with sodium sulfate and concentrated under reduced pressure. Chromatography with Et$_3$N:MeOH:EtOAc (5:5:90) afforded the product (46 mg).

FDMS m/e: found 531 (M+H$^+$); $^1$H NMR (CDCl$_3$): δ 7.35 (d, 2H), 7.20 (d, 1H), 7.16 (d, 1H), 7.10 (s, 1H), 6.94 (d, 2H), 6.65 (d, 1H), 6.61 (s, 1H), 6.51 (d, 1H), 4.72 (s, 2H), 4.15 (s, 2H), 3.79 (s, 2H), 3.54 (s, 3H), 3.10 (s, 3H), 2.99 (d, 3H), 2.79 (m, 4H), 1.85 (m, 4H).

EXAMPLE 39

Preparation of 6-Hydroxy-3-[3-methoxy-4-(1-pyrrolidinyl)benzyl]-2-[4-[(1-pyrrolidinyl)carbonyloxy]phenyl]benzo[b]thiophene

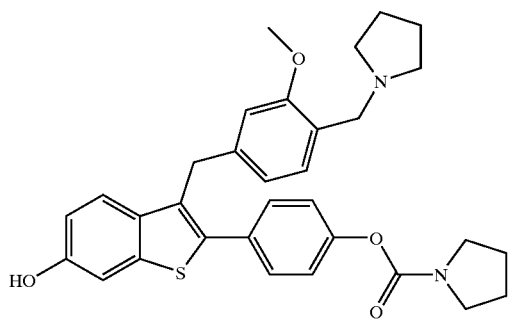

6-Benzyloxy-2-(4-hydroxyphenyl)-3-[3-methoxy-4-[(1-pyrrolidinyl)methyl]benzyl]benzo[b]thiophene (97 mg) was dissolved in pyridine (2.0 mL). Pyrrolidine carbonyl chloride (35 μL) was introduced at ambient temperature under argon through a syringe while stirring. The resulting mixture was allowed to stir under argon at 60° C. for 2 h. Cooled reaction mixture was diluted with brine (30 mL), extracted with dichloromethane (20 mL×3). The combined organic layers were dried with sodium sulfate and concentrated under reduced pressure. Chromatography with Et$_3$N:EtOAc (0–5%) afforded the acylation product (18 mg). This product was dissolved in THF (2.0 mL) and treated with a solution of ammonium formate (25% in H$_2$O, 1.0 mL) and 10% palladium on carbon (50 mg) sequentially at ambient temperature. The resulting mixture was stirred at ambient temperature under argon for 1 h before filtered through diatomaceous earth followed by rinsing with dichloromethane and methanol. The filtrate was extracted with dichloromethane (20 mL×3) from water (30 mL). The combined organic layers were dried with sodium sulfate and concentrated under reduced pressure. Chromatography with Et$_3$N:MeOH:EtOAc (5:5:90) afforded the title compound (6 mg).

FDMS m/e: found 543 (M+H$^+$); $^1$H NMR (CDCl$_3$): δ 7.38 (d, 2H), 7.27 (d, 1H), 7.25 (d, 1H), 7.14 (d, 2H), 7.05 (s, 1H), 6.68 (d, 1H), 6.66 (d, 1H), 6.61 (s, 1H), 4.15 (s, 2H), 3.90 (s, 2H), 3.60 (s, 3H), 3.58 (t, 2H), 3.56 (t, 2H), 2.91 (m, 4H), 1.98 (m, 4H), 1.95 (m, 4H).

EXAMPLE 40

Preparation of 6-Hydroxy-3-[3-methoxy-4-(1-pyrrolidinyl)benzyl]-2-[4-[(dimethylamino)carbonyloxy]phenyl]benzo[b]thiophene

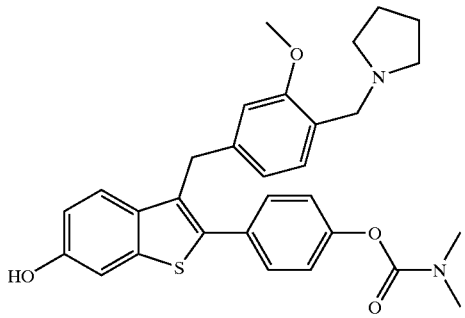

6-Benzyloxy-2-(4-hydroxyphenyl)-3-[3-methoxy-4-[(1-pyrrolidinyl)methyl]benzyl]benzo[b]thiophene (103 mg) was dissolved in pyridine (2.0 mL). Dimethylcarbamoyl carbonyl chloride (37 μL) was introduced at ambient temperature under argon through a syringe while stirring. The resulting mixture was allowed to stir under argon at 65° C. for 6 h. Cooled reaction mixture was concentrated under reduced pressure. Chromatography with Et$_3$N:EtOAc (0–5%) afforded the acylation product (93 mg). This product was dissolved in THF (5.0 mL) and treated with a solution of ammonium formate (25% in H$_2$O, 2.0 mL) and 10% palladium on carbon (100 mg) sequentially at ambient temperature. The resulting mixture was stirred at ambient temperature under argon for 1 h before filtered through diatomaceous earth followed by rinsing with dichloromethane and methanol. The filtrate was extracted with dichloromethane (20 mL×3) from water (30 mL). The combined organic layers were dried with sodium sulfate and concentrated under reduced pressure. Chromatography with Et$_3$N:MeOH:EtOAc (5:5:90) afforded the title compound (82 mg).

FDMS m/e: found 517 (M+H$^+$); $^1$H NMR (CDCl$_3$): δ 7.38 (d, 2H), 7.24 (d, 1H), 7.16 (d, 1H), 7.11 (d, 2H), 6.97 (s, 1H), 6.66 (d, 1H), 6.60 (s, 1H), 6.50 (d, 1H), 4.16 (s, 2H), 3.80 (s, 2H), 3.54 (s, 3H), 3.12 (s, 3H), 3.03 (s, 3H), 2.80 (m, 4H), 1.85 (m, 4H).

EXAMPLE 41

Preparation of 6-Hydroxy-3-[3-methoxy-4-(1-pyrrolidinyl)benzyl]-2-[4-[(4-morpholinyl)carbonyloxy]phenyl]benzo[b]thiophene

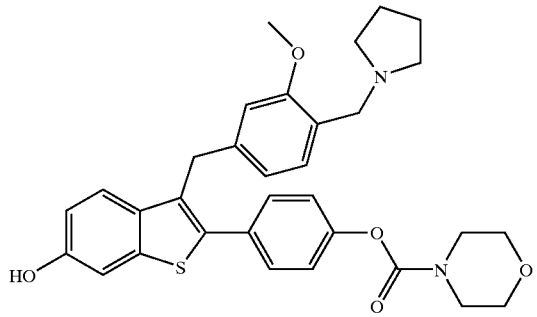

6-Benzyloxy-2-(4-hydroxyphenyl)-3-[3-methoxy-4-[(1-pyrrolidinyl)methyl]benzyl]benzo[b]thiophene (96 mg) was dissolved in pyridine (2.0 mL). 4-Morpholine carbonyl chloride (45 µL) was introduced at ambient temperature under argon through a syringe while stirring. The resulting mixture was allowed to stir under argon at ambient temperature for 24 h. Cooled reaction mixture was concentrated under reduced pressure. Chromatography with Et₃N:EtOAc (0–5%) afforded the acylation product (96 mg). This product was dissolved in THF (5.0 mL) and treated with a solution of ammonium formate (25% in H₂O, 2.0 mL) and 10% palladium on carbon (100 mg) sequentially at ambient temperature. The resulting mixture was stirred at ambient temperature under argon for 3 h before filtered through diatomaceous earth followed by rinsing with dichloromethane and methanol. The filtrate was extracted with dichloromethane (20 mL×3) from water (30 mL). The combined organic layers were dried with sodium sulfate and concentrated under reduced pressure. Chromatography with Et₃N:MeOH:EtOAc (5:5:90) afforded the title compound as a white foam (78 mg).

FDMS m/e: found 559 (M+H⁺); ¹H NMR (CDCl₃): δ 7.41 (d, 2H), 7.18 (d, 1H), 7.15 (d, 1H), 7.11 (d, 2H), 6.97 (s, 1H), 6.63 (d, 1H), 6.58 (s, 1H), 6.34 (d, 1H), 4.18 (s, 2H), 3.76 (m, 4H), 3.75 (m, 4H), 3.73 (s, 2H), 3.68 (s, 3H), 2.67 (m, 4H), 1.80 (m, 4H).

EXAMPLE 42

Preparation of 6-Hydroxy-3-[3-methoxy-4-[(1-pyrrolidinyl)methyl)benzyl]-2-[4-(methylaminocarbonylamino)phenyl]benzo[b]thiophene

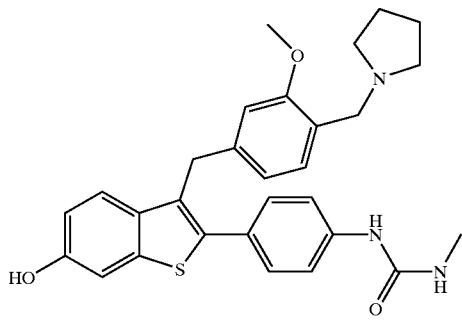

Part A. 6-Benzyloxy-2-[4-[bis(trimethylsilyl)amino]phenyl]benzo[b]thiophen-3-yl 3-Methoxy-4-[(1-pyrrolidinyl)methyl]phenyl Ketone.

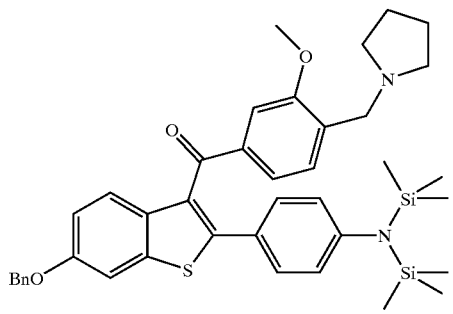

Magnesium turnings (0.25 g) were placed in a two-neck 100 mL round-bottom flask fitted with a reflux condenser and a magnetic stir bar. The whole apparatus was flame-dried and allowed to cool to ambient temperature. Dry THF (17 mL) and a small crystal of iodine were then introduced followed by slow addition of 4-bromo-N,N-bis(trimethylylsilyl)aniline (3.36 g) while stirring at ambient temperature. The reaction mixture was warmed to a gentle reflux for 1.5 h or until magnesium turnings were completely consumed to give a 0.5 M solution of the Grignard reagent. This freshly prepared Grignard solution (15 mL) was added slowly to a stirring solution of 6-benzyloxy-2-(dimethylamino)benzo[b]thiophen-3-yl 3-methoxy-4-[(1-pyrrolidinyl)methyl]phenyl ketone (2.48 g, 5.0 mmol) in THF (15.0 mL) at 0° C. under argon. The mixture was stirred at 0° C. for 3 h before quenched with saturated aqueous NH₄Cl solution (50 mL) and extracted with CH₂Cl₂ (50 mL×3). The combined organic layers were dried with sodium sulfate and concentrated under reduced pressure. Chromatography with EtOAc-hexane (0–100% gradient elution) afforded the title compound (0.73 g).

FDMS m/e: found 693 (M⁺); ¹H NMR (CDCl₃): δ 7.74 (d, 1H), 7.55–7.35 (m, 7H), 7.28 (d, 2H), 7.22 (d, 1H), 7.20 (d, 1H), 7.10 (d, 1H), 6.68 (d, 2H), 5.17 (s, 2H), 3.76 (s, 3H), 3.55 (s, 2H), 2.51 (m, 4H), 1.78 (m, 4H), 0.00 (s, 18H).

Part B. 6-Benzyloxy-3-[3-methoxy-4-[(1-pyrrolidinyl)methyl]benzyl]-2-(4-aminophenyl)benzo[b]thiophene.

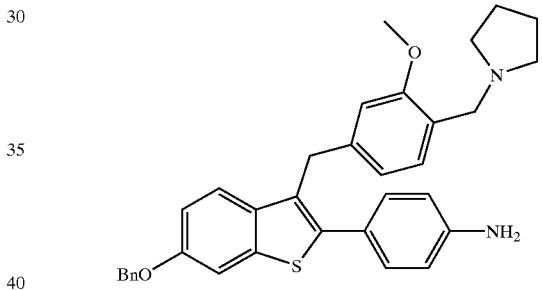

6-Benzyloxy-2-[4-[bis(trimethylsilyl)amino]phenyl]benzo[b]thiophen-3-yl 3-methoxy-4-[(1-pyrrolidinyl)methyl]phenyl ketone (0.73 g) was dissolved in THF (10 mL), cooled to 0° C. in an ice bath before treated with lithium aluminum hydride (110 mg) at 0° C. for 1 h, then quenched with water (1 ml) and sodium hydroxide (1.0 M, 1 mL). Stirring continued for 30 min. The reaction mixture was diluted with brine (30 mL) and extracted with dichloromethane (20 mL×3). The combined organic layers were dried with sodium sulfate and concentrated in vacuo to give the crude alcohol. This material was dissolved in dichloromethane (15 mL), treated with triethylsilane (1.5 mL) and trifluroacetic acid (1.5 mL) sequentially, allowed to stir at ambient temperature for 1.5 h, and concentrated under reduced pressure. The residue was extracted with dichloromethane (20 mL×3) from saturated aqueous sodium bicarbonate (30 mL). The combined organic layers were dried with sodium sulfate and concentrated. Chromatography with Et₃N:MeOH:EtOAc (5:5:90) afforded the title compound as a yellow foam (0.53 g).

FDMS m/e: found 535 (M+H⁺); ¹H NMR (CDCl₃): δ 7.60–7.45 (m, 7H), 7.30 (d, 2H), 6.98 (d, 1H), 6.70 (m, 4H), 5.13 (s, 2H), 4.21 (s, 2H), 3.78 (s, 2H), 3.70 (s, 3H), 3.62 (s, 2H), 2.56 (m, 4H), 1.78 (m, 4H).

Part C. 6-Hydroxy-3-[3-methoxy-4-(1-pyrrolidinyl)benzyl]-2-(4-aminophenyl)benzo[b]thiophene.

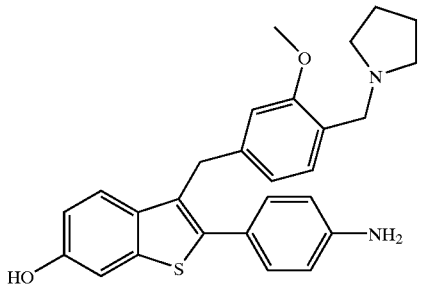

6-Benzyloxy-3-[3-methoxy-4-[(1-pyrrolidinyl)methyl]benzyl]-2-(4-aminophenyl)benzo[b]thiophene (103 mg) in THF (4.0 mL) was treated with a solution of ammonium formate (25% in H$_2$O, 2.0 mL) and 10% palladium on carbon (100 mg) sequentially at ambient temperature. The resulting mixture was stirred at ambient temperature under argon for 21 h before filtered through diatomaceous earth followed by rinsing with dichloromethane and methanol. The filtrate was extracted with dichloromethane (20 mL×3) from water (30 mL). The combined organic layers were dried with sodium sulfate and concentrated under reduced pressure. Chromatography with Et$_3$N:MeOH:EtOAc (5:10:85) afforded the product (80 mg).

$^1$H NMR (CDCl$_3$): δ 7.23 (d, 2H), 7.18 (d, 1H), 7.15 (d, 1H), 7.13 (s, 1H), 6.67 (d, 3H), 6.62 (s, 1H), 6.42 (d, 1H), 4.17 (s, 2H), 3.74 (s, 2H), 3.52 (s, 3H), 2.74 (m, 4H), 1.83 (m, 4H).

Part D. 6-Hydroxy-3-[3-methoxy-4-[(1-pyrrolidinyl)methyl)benzyl]-2-[4-(methylaminocarbonylamino)phenyl]benzo[b]thiophene.

6-Hydroxy-3-[3-methoxy-4-[(1-pyrrolidinyl)methyl]benzyl]-2-[4-aminophenyl]benzo[b]thiophene (80 mg) was dissolved in THF (5.0 mL), treated with sodium bicarbonate (45 mg) while stirring at ambient temperature, cooled to 0° C. in an ice bath before treated with methyl isocyanate (42 μL) under argon. The reaction mixture. was stirred at ambient temperature for 24 h and concentrated. Chromatography with Et$_3$N:MeOH:EtOAc (5:10:85) afforded the title compound (50 mg).

FDMS m/e: 502 (M+H$^+$); $^1$H NMR (CDCl$_3$): δ 7.62 (d, 2H), 7.51 (d, 1H), 7.30–7.10 (m, 5H), 6.68 (s, 1H), 6.67 (d, 1H), 5.80 (m, 1H), 5.65 (m, 1H), 4.20 (s, 2H), 3.76 (s, 2H), 3.74 (s, 3H), 3.03 and 3.2.90 (two d, 3H), 2.70 (m, 4H), 1.87 (m, 4H).

EXAMPLE 43

Preparation of 2-[4-(Cyanomethoxy)phenyl]-3-[4-[2-(1-pyrrolidinyl)ethoxy]benzyl]benzo[b]thiophene

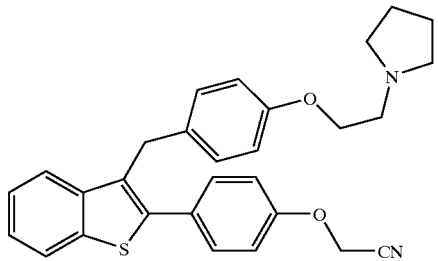

A suspension of 2-(4-hydroxyphenyl)-3-[4-[2-(1-pyrrolidinyl)ethoxy]benzyl]benzo[b]thiophene (102 mg) and cesium carbonate (386 mg) in DMF (3.0 mL) was treated with bromoacetonitrile (20 μL) while stirring at ambient temperature. Stirring was continued for 2 h and the reaction mixture was diluted with brine (30 mL) and extracted with EtOAc (20 mL×3). The combined organic layers were dried with sodium sulfate and concentrated under reduced pressure. Chromatography with Et$_3$N-EtOAc (0–5%) afforded the product (98 mg).

FDMS m/e: 469 (M+H$^+$); $^1$H NMR (CDCl$_3$): δ 7.88 (d, 1H), 7.59 (d, 1H), 7.57 (d, 2H), 7.34 (m, 2H), 7.09 (d, 2H), 7.03 (d, 2H), 6.85 (d, 2H), 4.82 (s, 2H), 4.24 (s, 2H), 4.14 (t, 2H), 3.00 (t, 2H), 2.73 (m, 4H), 1.86 (m, 4H).

EXAMPLE 44

Preparation of 2-[4-(Cyanomethyl)phenyl]benzo[b]thiophen-3-yl 4-[2-(1-Pyrrolidin-1-yl)ethoxy]phenyl Ketone

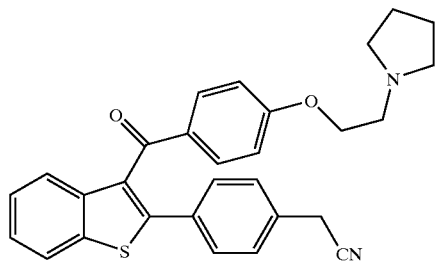

Part A. 2-[4-(Cyanomethyl)phenyl]benzo[b]thiophene.

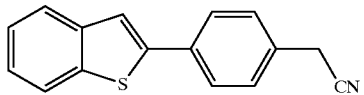

Benzo[b]thiophen-2-yl boronic acid (1.25 g) and 4-bromobenzyl nitrile (1.51 g) were dissolved in THF (25 mL), treated with a solution of sodium carbonate in water (2.0 M, 7.0 mL) and tetrakis(triphenylphosphine)palladium (0.25 g) and allowed to stir at reflux in the dark for 15 h. The cooled reaction mixture was diluted with water (100 mL) and extracted with dichloromethane (100 mL×3). The combined organic layers were dried with sodium sulfate and concentrated. The off-white solid was triturated with ethyl acetate and the product was collected as a white precipitate by centrifugation (1.5 g).

$^1$H NMR (CDCl$_3$): δ 7.77 (d, 1H), 7.68 (d, 1H), 7.31 (d, 2H), 7.30 (d, 2H), 7.28 (m, 2H), 7.20 (s, 1H), 3.75 (s, 2H).

Part B. 2-[4-(Cyanomethyl)phenyl]benzo[b]thiophen-3-yl 4-[2-(1-Pyrrolidin-1-yl)ethoxy]phenyl Ketone.

To a solution of 2-[4-(cyanomethyl)phenyl]benzo[b]thiophene (265 mg) and 4-[2-(1-pyrrolidinyl)ethoxy]benzoyl chloride (385 mg) in dichloromethane (20 mL) at 0° C. in the dark was added TiCl$_4$ (1.3 mL, neat) slowly under argon. The resulting mixture was stirred at 0° C. to ambient temperature for 5.5 h before it was transferred carefully to a stirring solution of saturated aqueous NaHCO$_3$ (100 mL). After stirring for 30 min, the mixture was extracted with CH$_2$Cl$_2$ (3×100 mL). The combined organic layers were dried (Na$_2$SO$_4$) and concentrated under reduced pressure. Chromatography with Et$_3$N:EtOAc (5%) afforded the product (230 mg).

$^1$H NMR (CDCl$_3$): δ 7.97 (d, 1H), 7.86 (d, 2H), 7.75 (d, 1H), 7.56 (d, 2H), 7.47 (m, 2H), 7.33 (d, 2H), 6.87 (d, 2H), 4.21 (t, 2H), 3.80 (s, 2H), 3.00 (t, 2H), 2.72 (m, 4H), 1.91 (m, 4H).

EXAMPLE 45

Preparation of 2-[4-(Cyanomethyl)phenyl]-3-[4-[2-(1-pyrrolidinyl)ethoxy]benzyl]benzo[b]thiophene

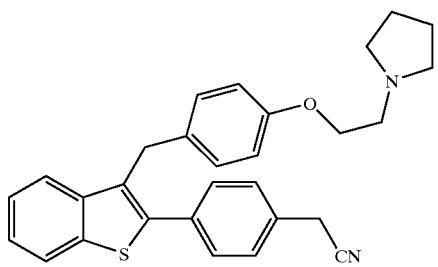

2-[4-(Cyanomethyl)phenyl]benzo[b]thiophen-3-yl 4-[2-(1-pyrrolidinyl)ethoxy]phenyl ketone (158 mg) in THF (5.0 mL) was treated with lithium aluminum hydride (13 mg) at 0° C. for 2 h, and then quenched with water (0.5 mL) and sodium hydroxide (5.0 M, 0.5 mL). Stirring was continued for 10 min. The reaction mixture was diluted with brine (50 mL) and extracted with dichloromethane (3×50 mL). The combined organic layers were dried with sodium sulfate and concentrated in vacuo to give a yellow foam-like material. This material was dissolved in dichloromethane (5 mL), treated with triethylsilane (0.3 mL) and trifluroacetic acid (0.2 mL) at 0° C. for 1.5 h, and concentrated under reduced pressure. The residue was extracted with dichloromethane (50 mL×3) from saturated aqueous sodium bicarbonate (50 mL). The combined organic layers were dried with sodium sulfate and concentrated. Chromatography with Et$_3$N:EtOAc (0–5%) afforded the product (106 mg).

$^1$H NMR (CDCl$_3$): δ 7.93 (d, 1H), 7.60 (d, 1H), 7.58 (d, 2H), 7.42 (d, 2H), 7.34 (m, 2H), 7.09 (d, 2H), 6.86 (d, 2H), 4.24 (s, 2H), 4.15 (t, 2H), 3.83 (s, 2H), 2.97 (t, 2H), 2.67 (m, 4H), 1.85 (m, 4H).

EXAMPLE 46

Preparation of 2-[4-[2-(Benzoylamino)ethyl]phenyl]-3-[4-[2-(1-pyrrolidinyl)ethoxy]benzyl]benzo[b]thiophene

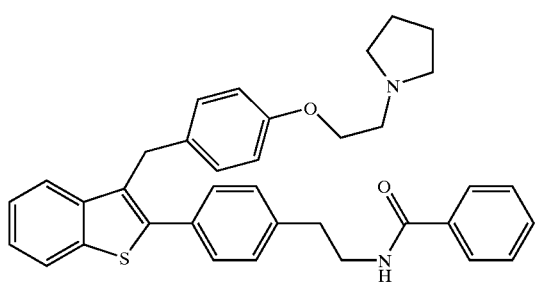

Part A. 2-[4-(2-Aminoethyl)phenyl]-3-[4-[2-(1-pyrrolidinyl)ethoxy]benzyl]benzo[b]thiophene.

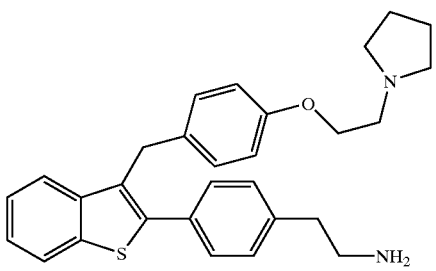

2-[4-(Cyanomethyl)phenyl]-3-[4-[2-(1-pyrrolidinyl)ethoxy]benzyl]benzo[b]thiophene (1.39 g) was dissolved in ethanol and warmed to 55° C. before it was treated with Raney nickel (1 mL slurry in water) followed by addition of hydrazine monohydrate (1.5 mL). The resulting mixture was allowed to stir at 55° C. for 30 min or until the evolution of gas had stopped. The cooled reaction mixture was filtered through diatomaceous earth, rinsed with methanol and dichloromethane. The filtrate was diluted with saturated sodium bicarbonate (50 mL) and extracted with dichloromethane (50 mL×3). The combined organic layers were dried with sodium sulfate and concentrated. Chromatography with NH$_4$OH:MeOH:EtOAc (5:10:85) afforded the product (1.30 g)

$^1$H NMR (CDCl$_3$): δ 7.89 (d, 1H), 7.54 (d, 1H), 7.49 (d, 2H), 7.30 (m, 4H), 7.09 (d, 2H), 6.86 (d, 2H), 4.27 (s, 2H), 4.11 (t, 2H), 3.04 (t, 2H), 2.92 (t, 2H), 2.82 (m, 2H), 2.65 (m, 4H), 1.84 (m, 4H).

Part B. 2-[4-[2-(Benzoylamino)ethyl]phenyl]-3-[4-[2-(1-pyrrolidinyl)ethoxy]benzyl]benzo[b]thiophene.

A solution of 2-[4-(2-aminoethyl)phenyl]-3-[4-[2-(1-pyrrolidinyl)ethoxy]benzyl]benzo[b]thiophene (140 mg) in dichloro-methane (3.0 mL) was treated benzoic acid (40 mg) and DCC (60 mg) sequentially and allowed to stir at ambient temperature for 17 h. The reaction mixture was then concentrated and fractionated by column chromatography with 5% Et$_3$N in EtOAc to afford the product (141 mg).

$^1$H NMR (CDCl$_3$): δ 7.96 (d, 1H), 7.80 (d, 2H), 7.65–7.30 (m, 9H), 7.14 (d, 2H), 6.91 (d, 2H), 6.40 (m, 1H), 4.33 (s, 2H), 4.22 (t, 2H), 3.81 (m, 2H), 3.06 (t, 2H), 3.01 (t, 2H), 2.76 (m, 4H), 1.89 (m, 4H).

EXAMPLE 47

Preparation of 3-[4-[2-(1-Pyrrolidinyl)ethoxy]benzyl]-2-[4-[2-(4-pyridinylcarbonylamino)ethyl]phenyl]benzo[b]thiophene

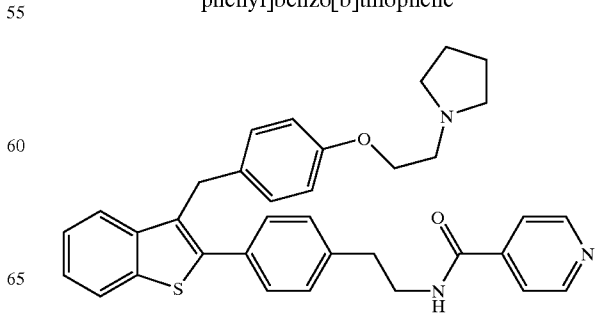

A solution of 2-[4-(2-aminoethyl)phenyl]-3-[4-[2-(1-pyrrolidinyl)ethoxy]benzyl]benzo[b]thiophene (111 mg) in dichloromethane (3.0 mL) was treated isonicotinic acid (35 mg) and DCC (50 mg) sequentially and allowed to stir at ambient temperature for 25 h. The reaction mixture was then concentrated and fractionated by column chromatography with $Et_3N$:MeOH:EtOAc (5:10:85) to afford the product (45 mg).

$^1$H NMR ($CDCl_3$): δ 8.80 (d, 2H), 7.97 (d, 1H), 7.68 (d, 2H), 7.60 (d, 1H), 7.55 (d, 2H), 7.38 (m, 3H), 7.12 (d, 2H), 6.91 (d, 2H), 6.75 (m, 1H), 4.33 (s, 2H), 4.22 (m, 2H), 3.81 (m, 2H), 3.08 (m, 4H), 2.83 (m, 4H), 1.96 (m, 4H).

EXAMPLE 48

Preparation of 3-[4-[2-(1-Pyrrolidinyl)ethoxy] benzyl]-2-[4-(2-oxopyrrolidin-4-ylcarbonylamino) phenyl]benzo[b]thiophene Oxalate

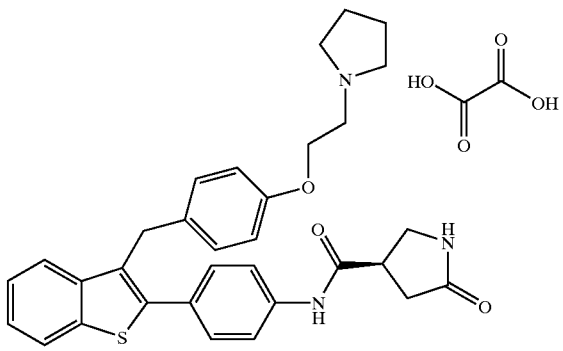

By essentially following the conditions described in Example 16, Part E, the free base of the title compound was prepared from 4-carboxy-2-oxopyrrolidine and 2-(4-aminophenyl)-3-[4-[2-(1-pyrrolidinyl)ethoxy]benzyl]benzo[b]thiophene (Example 16; Part D). The product was converted to the oxalate salt according to the conditions described in Example 1, Part G.

FDMS 540 (M+1); Anal. calcd for $C_{32}H_{33}N_3O_3S.C_2H_2O_4$: C, 64.85; H, 5.60; N, 6.67. Found: C, 64.99; H, 5.78; N, 6.81.

EXAMPLE 49

Preparation of 3-[4-[2-(1-Pyrrolidinyl)ethoxy] benzyl]-2-[4-(6-oxopiperidin-2-ylcarbonylamino) phenyl]benzo[b]thiophene Oxalate

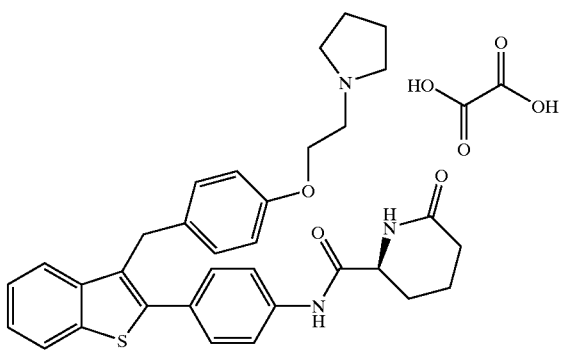

By essentially following the conditions described in Example 16, Part E, the free base of the title compound was prepared from 6-oxo-2-piperidine carboxylic acid (Miller et al., GB 1569486) and 2-(4-aminophenyl)-3-[4-[2-(1-pyrrolidinyl)ethoxy]benzyl]benzo[b]thiophene (Example 16; Part D). The product was converted to the oxalate salt according to the conditions described in Example 1, Part G.

FDMS 600 (M+1); Anal. calcd for $C_{33}H_{35}N_3O_3S.C_2H_2O_4.H_2O$: C, 63.52; H, 5.94; N, 6.35. Found: C, 64.99; H, 5.78; N, 6.81.

EXAMPLE 50

Preparation of 3-[4-[2-(1-Pyrrolidinyl)ethoxy] benzyl]-2-[4-(1,1-dioxo-isothiazolidin-3-ylcarbonylamino)phenyl]benzo[b]thiophene Oxalate

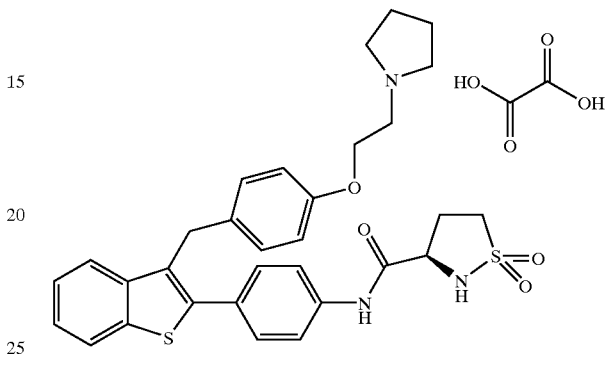

Part A. 3-[4-[2-(1-Pyrrolidinyl)ethoxy]benzyl]-2-[4-(2-benzyloxycarbonyl-1,1-dioxo-isothiazolidin-3-ylcarbonylamino)phenyl]benzo[b]thiophene.

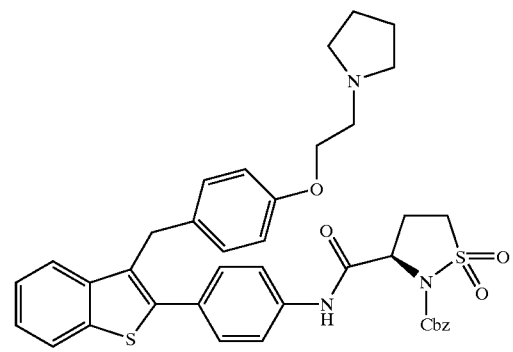

By essentially following the conditions described in Example 16, Part E, the free base of the title compound was prepared from 2-benzyloxycarbonylisothiazolidine-3-carboxylic acid 1,1-dioxide (Luisi and Pinnen, Arch. Pharm., 1993, 326, 139–141) and 2-(4-aminophenyl)-3-[4-[2-(1-pyrrolidinyl)ethoxy]benzyl]benzo[b]thiophene (Example 16; Part D).

FDMS 710 (M+1); Anal. calcd for $C_{39}H_{39}N_3O_6S_2.0.5$ MeOH: C, 65.36; H, 5.69; N, 5.79. Found: C, 65.06; H, 5.64; N, 5.84.

Part B. 3-[4-[2-(1-Pyrrolidinyl)ethoxy]benzyl]-2-[4-(1,1-dioxo-isothiazolidin-3-ylcarbonylamino)phenyl]benzo[b]thiophene Oxalate.

By essentially following the conditions described in Example 1, Part F, the free base of the title compound was prepared from 3-[4-[2-(1-pyrrolidinyl)ethoxy]benzyl]-2-[4-(2-benzyloxycarbonyl-1,1-dioxo-isothiazolidin-3-ylcarbonylamino)phenyl]benzo[b]thiophene (Part A). The product was converted to the oxalate salt according to the conditions described in Example 1, Part G.

FDMS 576 (M+1); Anal. calcd for $C_{31}H_{33}N_3O_4S_2.C_2H_2O_4.0.5$ $H_2O$: C, 58.74; H, 5.38; N, 6.23. Found: C, 58.93; H, 5.25; N, 5.99.

EXAMPLE 51

Preparation of 3-Methoxy-4-(1-pyrrolidinylmethyl)phenyl (R)-2-[4-(5-Oxopyrrolidinyl-2-ylmethoxy)phenyl]benzo[b]thiophen-3-yl Ketone Oxalate

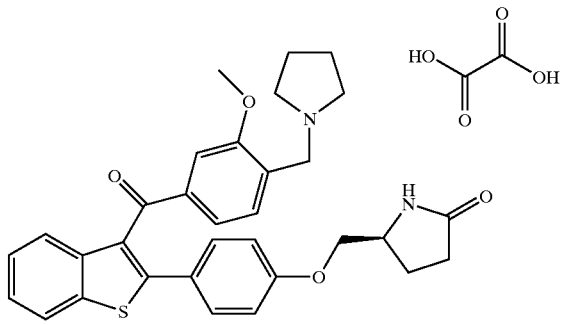

A. 2-[4-(Triisopropylsilyloxy)phenyl]benzo[b]thiophen-3-yl 3-Methoxy-4-(1-pyrrolidinylmethyl)phenyl Ketone.

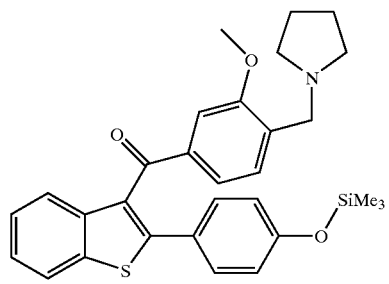

By essentially following the conditions described in Example 16, part A, 2-(dimethylamino)benzo[b]thiophen-3-yl 3-methoxy-4-(1-pyrrolidinylmethyl)phenyl ketone was prepared from 2-dimethylaminobenzo[b]thiophene (Vesterager et al., Tetrahedron, 1973, 29, 321–329) and 3-methoxy-4-(1-pyrrolidinylmethyl)benzoic acid in 65% yield. This material was converted to the title compound in 75% yield by essentially following the conditions described in Example 8, Part A.

FDMS 600 (M+1); Anal. calcd for $C_{36}H_{45}NO_3SSi$: C, 71.95; H, 7.58; N, 2.46. Found: C, 58.93; H, 5.25; N, 5.99.

Part B. 2-(4-Hydroxyphenyl)benzo[b]thiophen-3-yl 3-Methoxy-4-(1-pyrrolidinylinethyl)phenyl Ketone.

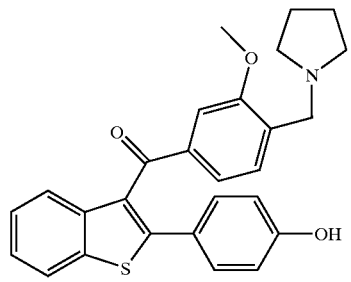

By essentially following the procedure described in Example 8, Part B, the title compound was prepared from 2-[4-(triisopropylsilyloxy)phenyl]benzo[b]thiophen-3-yl 3-methoxy-4-(1-pyrrolidinylmethyl)phenyl ketone (Part A) in 82% yield.

FDMS 444 (M+1); Anal. calcd for $C_{27}H_{25}NO_3S$: C, 73.11; H, 5.68; N, 3.16. Found: C, 72.93; H, 5.71; N, 3.39.

C. 3-Methoxy-4-(1-pyrrolidinylmethyl)phenyl (R)-2-[4-(5-Oxopyrrolidinyl-2-ylmethoxy)phenyl]benzo[b]thiophen-3-yl Ketone Oxalate.

By essentially following the conditions described in Example 10, Part F, the free base of the title compound was prepared from 2-(4-hydroxyphenyl)benzo[b]thiophen-3-yl 3-methoxy-4-(1-pyrrolidinylmethyl)phenyl ketone (Part B) and R-(−)-pyrrolidinone in 61% yield. The product was converted to the oxalate salt according to the conditions described in Example 1, Part G.

FDMS 541 (M+1).

EXAMPLE 52

Preparation of 3-[4-[2-(1-Pyrrolidinyl)ethoxy]benzyl]-2-[4-(phenyloxoacetylamino)phenyl]benzo[b]thiophene Oxalate

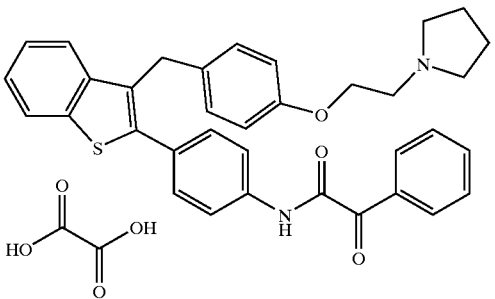

To a solution of the aniline (50 mg, 0.117 mmol), described above in Example 16, Part D, in dichloromethane (1 mL) was added 1-(3-dimethylaminopropyl)-3-ethyl-carbodiimide hydrochloride (45 mg, 0.233 mmol, 2.0 eq), benzoylformic acid (17.5 mg, 0.117 mmol, 1.0 eq) and a catalytic amount of 4-dimethylaminopyridine. After 18 h, the reaction mixture was diluted 50-fold with ethyl acetate, washed with saturated sodium bicarbonate (15 mL), then brine (15 mL). The solvent was removed under reduced pressure then the residue was purified by chromatography (silica, 20% THF in chloroform) to give 50 mg of the free base. This material was taken up in ethyl acetate and a solution of oxalic acid in ethyl acetate (89 μL of 0.1 M) was added. The resultant precipitate was collected via centrifugation to provide 50 mg (77%) of the title oxalate salt as a tan solid. Analysis for $C_{35}H_{32}N_2O_3S \cdot C_2H_2O_4$: Calcd: C, 68.29; H, 5.27; N, 4.30; Found: C, 68.44; H, 5.40; N, 4.32.

EXAMPLE 53

Preparation of 3-[4-[2-(1-Pyrrolidinyl)ethoxy]benzyl]-2-[4-(aminooxoacetylamino)phenyl]benzo[b]thiophene Hydrochloride

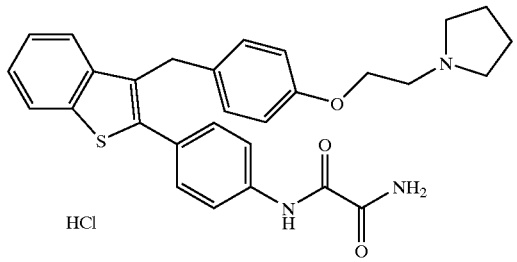

To a solution of the aniline (71 mg, 0.165 mmol) described above in Example 16, Part D, in dichloromethane (10 mL) was added oxalyl chloride (144 μL, 1.65 mmol, 10 eq). The solvent was removed under reduced pressure after 5 min; then the residue was treated with a solution of concentrated ammonium hydroxide (1 mL) in THF (5 mL). The reaction mixture was diluted 50-fold with THF and water was added (60 mL). The aqueous layer was saturated with sodium chloride then the THF layer was separated. The solvent was removed under reduced pressure and the residue passed through 1 g of SCX resin with two column volumes of methanol then two column volumes of 2 N ammonia in methanol. The latter fractions were combined, and the solvent was removed under reduced pressure. The resultant residue was purified by preparative HPLC to give 24 mg (29%) of the title product as the hydrochloride salt.

$^1$HNMR (300 MHz, DMSO-$d_6$) δ 1.82 (bm, 2H), 1.95 (bm, 2H), 2.48 (bm, 2H), 3.05 (bm, 2H), 3.29 (bm, 2H), 3.48 (bm, 2H), 4.19 (s, 2H), 6.85 (d, J=8.3 Hz, 2H), 7.01 (d, J=8.3 Hz, 2H), 7.32 (m, 1H), 7.48 (d, J=7.7 Hz, 2H), 7.54 (m, 1H), 7.91 (d, J=7.7 Hz, 2H), 7.95 (m, 2H), 8.31 (bs, 1H), 10.37 (bs, 1H), 10.76 (bs, 1H) ppm.

EXAMPLE 54

Preparation of 2-Hydroxy-3-[3-methoxy-4-(1-pyrrolidinylmethyl)benzyl]-2-[4-(methoxyoxoacetylamino)phenyl]benzo[b]thiophene Oxalate

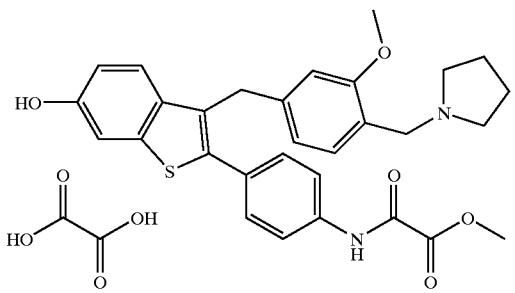

Part A. 2-Benzyloxy-3-[3-Methoxy-4-(1-pyrrolidinylmethyl)benzyl]-2-[4-(methoxyoxoacetylamino)phenyl]benzo[b]thiophene.

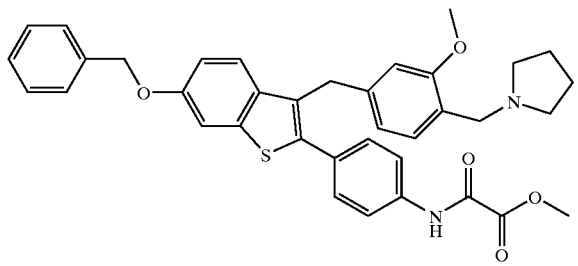

To a solution of the aniline (60 mg, 0.112 mmol) described above in Example 42, Part B, in dichloromethane (1 mL) and pyridine (1 mL) was added a solution of oxalyl chloride (10 μL, 0.112 mmol, 1.0 eq) in dichloromethane (1 mL) at −78° C. The reaction was quenched at −78° C. after 15 min by the addition of methanol (1 mL) followed by addition of 5% aqueous sodium bicarbonate. The reaction mixture was diluted 50-fold with ethyl acetate and allowed to warm to ambient temperature. The layers were separated; then the organic layer was washed with brine (25 mL), dried (magnesium sulfate), filtered, and stripped of solvent under reduced pressure. The residue was purified by chromatography (silica, 5% methanol in chloroform) to give 65 mg (93%) of the desired product.

FDMS (methanol) m/z=621 (M+H).

Part B. 2-Hydroxy-3-[3-Methoxy-4-(1-pyrrolidinylmethyl)benzyl]-2-[4-(methoxyoxoacetylamino)phenyl]benzo[b]thiophene Oxalate.

To a solution of the material prepared above (55 mg, 0.91 mmol) in THF (5 mL) was added an aqueous solution of ammonium formate (0.2 mL of 25% w/v) and 5% Pd on carbon (55 mg, 1 wt eq). The reaction mixture was stirred vigorously at ambient temperature. After 18 h, the reaction mixture was filtered through a bed of diatomaceous earth. The solvent was removed under reduced pressure and the residue was passed through 1 g of SCX resin elution with two column volumes of methanol then two column volumes of 2 N ammonia in methanol. The latter fractions were combined, then the solvent was removed under reduced pressure. The residue was taken up in ethyl acetate, and a solution of oxalic acid (48 μL of 0.1 N in ethyl acetate) was added. The resultant precipitate was isolated via centrifugation to give 30 mg (63%) of the title product.

$^1$HNMR (300 MHz, methanol-$d_4$) δ 1.79 (bm, 4H), 2.65 (bm, 4H), 3.68 (s, 3H), 3.70 (s, 2H), 4.21 (s, 2H), 6.66 (d, J=7.6 Hz, 1H), 6.73 (d, J=0.78 Hz, 1H), 6.79 (d, J=7.6 Hz, 1H), 7.12 (d, J=7.6 Hz, 1H), 7.20 (d, J=2.11 Hz, 1H), 7.38 (d, J=7.6 Hz, 1H), 7.45 (d, J=6.7 Hz, 2H), 7.76 (d, J=6.7 Hz, 2H) ppm.

EXAMPLE 55

Preparation of 3-[4-[2-(1-Pyrrolidinyl)ethoxy]benzyl]-2-[4-(methylaminocarbonylamino)phenyl]benzo[b]thiophene Oxalate

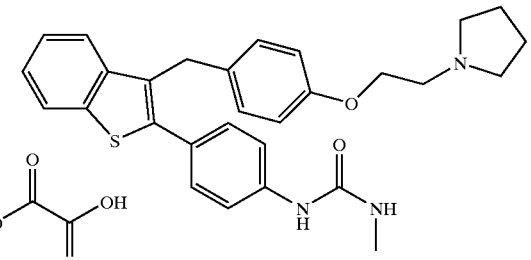

To a solution of the aniline (64 mg, 0.15 mmol) described above in Example 16, Part B, in ethanol-free chloroform (1 mL) was added methyl isocyanate (21 μL, 0.327 mmol, 1.75 eq). After 2 h, the reaction mixture was loaded onto 1 g of SCX resin. The cartridge was washed with two column volumes of chloroform, two column volumes of 20% methanol in chloroform then two column volumes of 20% 2 N ammonia in methanol in chloroform. The last two fractions were combined then the solvent was removed under reduced pressure. The residue was taken up in methanol, loaded onto another 1 g of SCX resin and washed again with the same series of solvents to give 38 mg (52%) of title product after final purification via preparative HPLC.

$^1$HNMR (300 MHz, DMSO-$d_6$) δ 1.81 (bm, 2H), 1.94 (bm, 2H), 2.60 (s, 3H), 3.02 (bm, 2H), 3.48 (m, 4H), 4.17 (s, 2H), 4.23 (s, 2H), 4.60 (bm, 4H), 6.84 (d, J=7.5 Hz, 2H), 7.01 (d, J=7.5 Hz, 2H), 7.30 (m, 4H), 7.50 (m, 3H), 7.92 (m, 1H), 9.06 (s, 1H), 10.64 (bs, 1H) ppm.

EXAMPLE 56

Preparation of 3-[4-[2-(1-Pyrrolidinyl)ethoxy]benzyl]-2-[3-(methylaminocarbonylamino)phenyl]benzo[b]thiophene Oxalate

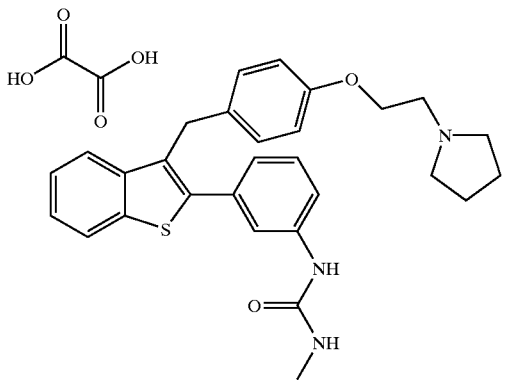

To a solution of the aniline (83 mg, 0.194 mmol) of Example 59, Part B, in ethanol-free chloroform (1 mL) was added methyl isocyanate (35 µL, 0.581 mmol, 2.9 eq). After 18 h, the reaction mixture was purified by passage through 1 g of SXC resin. The residue was further purified by chromatography (silica, 5% methanol in chloroform) to give 89 mg of the free base. An 86 mg portion was converted into the oxalate salt by dissolution into ethyl acetate and treatment with a solution of oxalic acid in ethyl acetate (1.77 mL of 0.1 M). The resultant precipitate was collected via centrifugation to give the desired salt as a tan solid (101 mg, 100%).

Analysis for $C_{29}H_{31}N_3O_2S \cdot C_2H_2O_4$: Calcd: C, 64.68; H, 5.78; N, 7.30; Found: C, 64.89; H, 5.92; N, 7.29.

EXAMPLE 57

Preparation of 3-[4-[2-(1-Pyrrolidinyl)ethoxy]benzyl]-2-[3-(aminocarbonylamino)phenyl]benzo[b]thiophene Hydrochloride

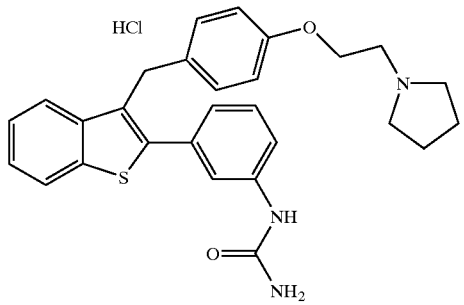

To a solution of the aniline (54 mg, 0.127 mmol) of Example 59, Part B, in ethanol-free chloroform (2 mL) was added a solution of phosgene in toluene (0.884 mL of 20% wt/v, 0.636 mmol, 5.0 eq). After 15 min, the solvents were removed under reduced pressure. The residue was treated with concentrated ammonium hydroxide (1 mL) in THF (2 mL) for 1 h. The reaction mixture was diluted 30-fold with THF then brine was added to separate the layers. The organic layer was separated; then the solvent was removed under reduced pressure. The residue was purified by preparative HPLC to give 23 mg (36%) of the title product.

Analysis for $C_{28}H_{29}N_3O_2S \cdot HCl \cdot H_2O$: Calcd: C, 63.92; H, 6.13; N, 7.99; Found; C, 63.90; H, 5.63; N, 7.70.

EXAMPLE 58

Preparation of 3-[4-[2-(1-Pyrrolidinyl)ethoxy]benzyl]-2-[4-(methoxyoxoacetylamino)phenyl]benzo[b]thiophene

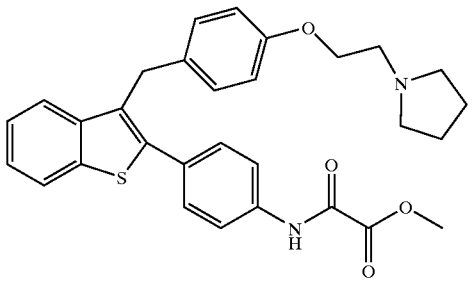

To the aniline (124 mg, 0.289 mmol) of Example 16, Part D, in pyridine/$CH_2Cl_2$ (1:1, 2 mL) at 0° C. and under $N_2$, was added methyl oxalyl chloride and the solution stirred at 0° C. for 25 minutes. After diluting 50 fold with EtOAc, the organics were washed with saturated $NaHCO_3$, $H_2O$, brine, and concentrated in vacuo. Material was purified by flash chromatography ($SiO_2$, 10% MeOH in $CHCl_3$), yielding 128 mg of the title product.

FDMS 515 (M+); Anal. Calcd. for $C_{30}H_{30}N_2O_4S \cdot 0.5 H_2O$: C, 68.81; H, 5.97; N, 5.35 Found: C, 68.81; H, 5.68; N, 5.31.

EXAMPLE 59

Preparation of 3-[4-[2-(1-Pyrrolidinyl)ethoxy]benzyl]-2-[3-(methoxyoxoacetylamino)phenyl]benzo[b]thiophene

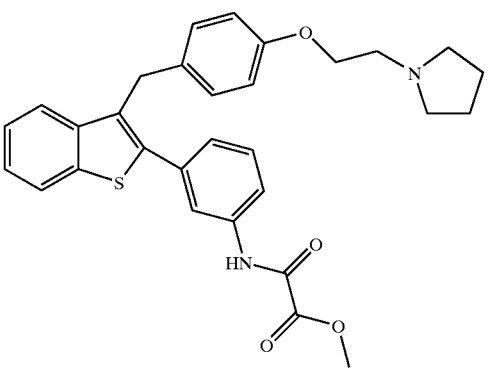

Part A. 2-(3-Aminophenyl)benzo[b]thiophen-3-yl 4-[2-(1-Pyrrolidinyl)ethoxy]phenyl Ketone.

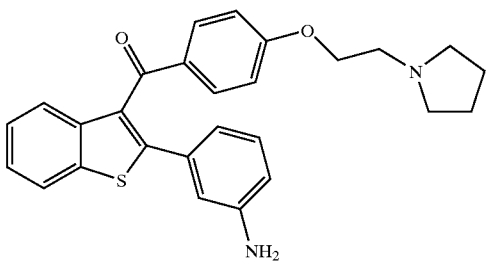

The above titled compound was prepared from 8.43 g (22.3 mmol) of 2-dimethylaminobenzo[b]thiophene-3-yl 4-[2-(1-pyrrolidinyl)ethoxy]phenyl ketone (Example 16, Part B) and 10.6 g (33.48 mmol) of 3-bromo-N,N-bis(trimethylsilyl)aniline by following the procedure outlined in Example 16, Part C, affording 7.0 g of desired product.

FDMS 442 (M+); Anal. Calcd. for $C_{27}H_{26}N_2O_2S \cdot 0.75$ $H_2O$: C, 71.10; H, 6.08; N, 6.14 Found: C, 71.02; H, 5.80; N, 6.19.

Part B. 2-(3-Aminophenyl)-3-[4-[2-(1-pyrrolidinyl)ethoxy]benzyl]benzo[b]thiophene.

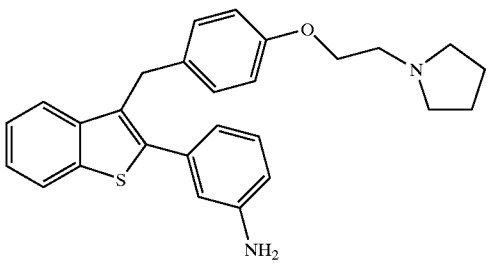

The above-titled compound was prepared from the product of Part A by essentially following the procedure outlined in Example 3, Part A. Material was purified by flash chromatography ($SiO_2$, 10% MeOH in $CHCl_3$), yielding 6.1 g of the title product.

FDMS 428.1 (M+); Anal. Calcd. for $C_{27}H_{28}N_2OS \cdot 0.5$ $H_2O$: C, 74.10; H, 6.68; N, 6.40 Found: C, 73.84; H, 6.66; N, 6.56.

Part C. 3-[4-[2-(1-Pyrrolidinyl)ethoxy]benzyl]-2-[3-(methoxyoxoacetylamino)phenyl]benzo[b]thiophene.

The title compound was prepared from the product of Part B by essentially following the procedure outlined for Example 58. Material was purified by flash chromatography ($SiO_2$, 1% MeOH in $CHCl_3$); yielding 118 mg (87%) of the title product.

$^1$H NMR ($CDCl_3$) δ 8.89 (s, 1H), 7.87 (d, J=1.7 Hz, 1H), 7.85 (d, J=1.7 Hz, 1H), 7.69 (s, 1H), 7.57 (d, J=1.8 Hz, 1H), 7.42 (t, J=7.9 Hz, 1H), 7.34 (m, 3H), 7.05 (d, J=8.5 Hz, 2H), 6.81 (d, J=8.5 Hz, 2H), 4.25 (s, 2H), 4.09 (t, J=6.0 Hz, 2H), 3.99 (s, 3H), 2.91 (t, J=5.9 Hz, 2H), 2.65 (bs, 4H), 1.82 (m, 4H); FDMS 514.1 (M+).

EXAMPLE 60

Preparation of 3-[4-[2-(1-Pyrrolidinyl)ethoxy]benzyl]-2-[4-(2-oxo-oxazolidin-5-yl)phenyl]benzo[b]thiophene

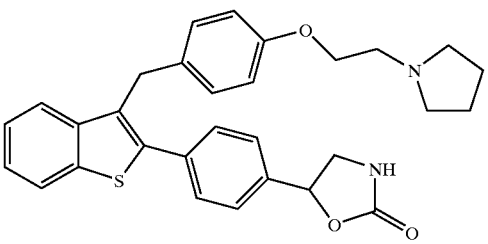

Part A. 2-(4-Formylphenyl)-3-[4-[2-(1-pyrrolidinyl)ethoxy]benzyl]benzo[b]thiophene.

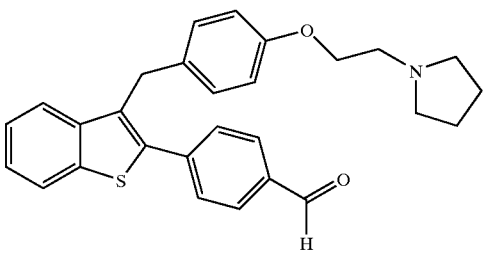

To a solution of $Mg^0$ (0.385 mg, 16.08 mmol), in THF (1 mL), was added p-bromobenzaldehyde dimethylacetal (3.71 g, 16.08 mmol, prepared from p-bromobenzaldehyde and MeOH following standard procedures) and the mixture stirred for 1 h. Additional THF (15 mL) was added to the Grignard reagent and then the solution transferred to a flask containing 2-dimethylaminobenzo[b]thiophene-3-yl 4-[2-(1-pyrrolidinyl)ethoxy]phenyl ketone (3.04 g, 8.04 mmol) in THF (15 mL). The mixture was stirred at room temperature for 2 h, then quenched by the addition of saturated $NH_4Cl$, then $H_2O$, and extracted into EtOAc. The organic extracts were concentrated in vacuo, and the resulting residue purified by flash chromatography ($SiO_2$, 2% MeOH in $CHCl_3$). To LAH (47 mg, 1.25 mmol) in THF (1 mL) was added the above ketone (585 mg, 1.25 mmol) in THF (4 mL). The mixture was stirred at room temperature for 1 h and then quenched by the sequential addition of 50 μL of $H_2O$, 50 μL of 15% NaOH, and 150 μl $H_2O$. The resulting aluminum salts were removed by filtering over a pad of diatomaceous earth and the filtrate concentrated in vacuo. The resulting alcohol was then taken up in 80% HOAc, stirred for 2 h and then concentrated in vacuo. The residue was dissolved in $CH_2Cl_2$, cooled to 0° C. and treated with $Et_3SiH$ (7 equivalents). TFA (10 equivalents) was then added and the reaction stirred at 0° C. for 1 minute and then quenched by the addition of saturated $NaHCO_3$. Material was then diluted 10 fold with EtOAc, the organics washed with $H_2O$, and concentrated in vacuo. Material purified by flash chromatography ($SiO_2$, 1% MeOH in $CHCl_3$ with 1% $Et_3N$ v/v added).

FDMS 441.9 (M+); Anal. Calcd. For $C_{28}H_{27}NO_2S \cdot 0.5$ $H_2O$: C, 74.63; H, 6.26; N, 3.11. Found: C, 74.86; H, 6.17; N, 3.08.

Part B. 3-[4-[2-(1-Pyrrolidinyl)ethoxy]benzyl]-2-[4-(2-oxo-oxazolidin-5-yl)phenyl]benzo[b]thiophene.

To the 229 mg (0.519 mmol) of the benzaldehyde (Part A) was added trimethylsilyl cyanide (103 mg, 1.04 mmol), KCN (catalytic), 18-crown-6 (catalytic), and CH$_2$Cl$_2$ (2 mL). The mixture was stirred at room temperature for 5 h and then a catalytic amount of ZnI$_2$ added and the solution stirred overnight. After diluting 50 fold with EtOAc, the organics were washed with H$_2$O, brine, and concentrated in vacuo. The resulting cyanohydrin was taken up in THF (3 mL) and added to a mixture of LAH (59 mg, 1.56 mmol) in THF (1 mL). The material was stirred at room temperature for 2 h and then quenched by the sequential addition of 60 μL H$_2$O, 60 μL of 15% NaOH, and 120 μL H$_2$O. The resulting aluminum salts were removed by filtering over a pad of diatomaceous earth and the filtrate concentrated in vacuo. Material was purified by flash chromatography (SiO$_2$, 15% MeOH in CHCl$_3$ with 1% Et$_3$N v/v added); yielding 157 mg of the amino-alcohol. To this product was added NaH (1 mg), diethyl carbonate (41 μL, 0.366 mmol), and o-xylenes (5 mL). The mixture was heated at 150° C. for 14 h, then allowed to cool to room temperature. After diluting 25 fold with EtOAc, the organics were washed with H$_2$O, brine, and concentrated in vacuo. Material was purified by flash chromatography (SiO$_2$, 7% MeOH in CHCl$_3$).

FDMS 499 (M+); Anal. Calcd. for C$_{30}$H$_{30}$N$_2$O$_3$S.0.5 H$_2$O: C, 70.97; H, 6.16; N, 5.52 Found: C, 71.23; H, 6.46; N, 5.20.

EXAMPLE 61

Preparation of 3-[4-[2-(1-Pyrrolidinyl)ethoxy] benzyl]-2-[4-[1-hydroxy-2-(methylsulfonylamino) ethyl]phenyl]benzo[b]thiophene Oxalate

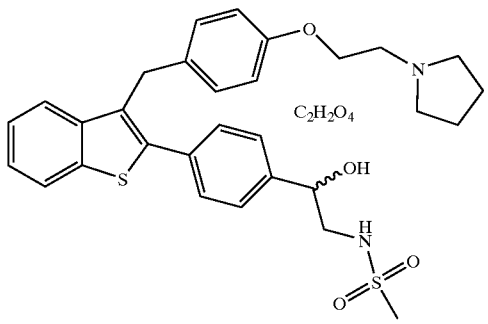

To the 229 mg (0.519 mmol) of the benzaldehyde of Example 60, Part A was added trimethylsilyl cyanide (103 mg, 1.04 mmol), KCN (catalytic), 18-crown-6 (catalytic), and CH$_2$Cl$_2$ (2 mL). The mixture was stirred at room temperature for 5 h and then a catalytic amount of ZnI$_2$ added and the solution stirred overnight. After diluting 50 fold with EtOAc, the organics were washed with H$_2$O, brine, and concentrated in vacuo. The resulting cyanohydrin was taken up in THF (3 mL) and added to a mixture of LAH (59 mg, 1.56 mmol) in THF (1 mL). The material was stirred at room temperature for 2 h and then quenched by the sequential addition of 60 μL H$_2$O, 60 μL of 15% NaOH, and 120 μL H$_2$O. The resulting aluminum salts were removed by filtering over a pad of diatomaceous earth and the filtrate concentrated in vacuo. Material was purified by flash chromatography (SiO$_2$, 15% MeOH in CHCl$_3$ with 1% Et$_3$N v/v added); yielding 157 mg of the amino-alcohol. To 51 mg (0.108 mmol) of this residue in THF (0.5 mL) was added Et$_3$N (15 μL, 0.108 mmol) and methanesulfonyl chloride (8 μL, 0.108 mmol). The mixture was stirred at room temperature for 3 h, then diluted 100 fold with EtOAc. The organics were washed with H$_2$O, saturated NaHCO$_3$, brine, and concentrated in vacuo. Material was purified by flash chromatography (SiO$_2$, 10% MeOH in CHCl$_3$) and the mono-oxalate salt formed by taking the residue up in a minimal amount of EtOAc, adding 1 equivalent of 0.1 N oxalic acid in EtOAc, and the resulting product collected by centrifugation and dried.

$^1$H NMR (CDCl$_3$) δ 7.86 (d, J=7.4 Hz, 1H), 7.51 (m, 4H), 7.40 (d, J=7.4 Hz, 1H), 7.29 (m, 2H), 7.03 (d, J=8.3 Hz, 2H), 6.86 (d, J=8.5 Hz, 2H), 5.09 (m, 1H), 4.28 (t, J=6.8 Hz, 2H), 4.24 (s, 2H), 3.61 (m, 2H), 3.59 (m, 4H), 3.28 (m, 2H), 2.86 (s, 3H), 2.11 (m, 4H).

EXAMPLE 62

Preparation of 2-[4-(Aminooxoacetylamino)phenyl]-2-hydroxy-3-[3-methoxy-4-(1-pyrrolidinyimethyl) benzyl]benzo[b]thiophene Oxalate

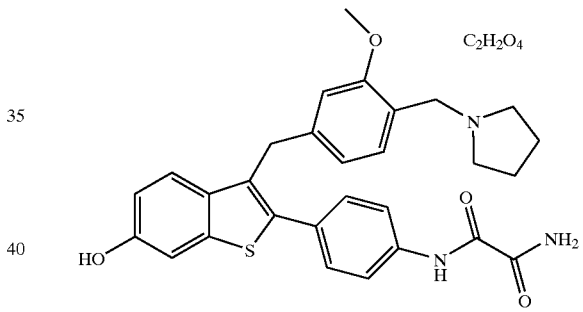

To 121 mg (0.195 mmol) of the oxamide ester of Example 54 in THF (3 mL) was added concentrated NH$_4$OH (1 mL) and the mixture heated at reflux for 30 minutes. After concentrating in vacuo, the crude residue was taken up in MeOH (5 mL) and added to NH$_4$CO$_2$H (123 mg, 1.95 mmol) and 10% Pd/C (120 mg). The mixture was heated at reflux for 45 minutes and then the catalyst removed by filtering over a pad of diatomaceous earth and the filtrate concentrated in vacuo. The resulting residue was partitioned between saturated NaHCO$_3$ and EtOAc, and the organic extracts washed with H$_2$O, brine, and concentrated in vacuo. Material was purified by flash chromatography (SiO$_2$, 10% MeOH in CHCl$_3$ with 1% Et$_3$N v/v added). The mono-oxalate salt was formed by taking the residue up in a minimal amount of EtOAc, adding 1 equivalent of 0.1 N oxalic acid in EtOAc, and the resulting product collected by centrifugation and dried.

$^1$H NMR (CD$_3$OD) δ 7.5 (d, 2H), 7.25 (m, 2H), 7.15 (d, 1H), 7.0 (s, 1H), 6.85 (d, 1H), 6.55 (dd, 1H), 6.45(m, 2H), 3.95 (s, 2H), 3.45 (s, 3H), 3.40 (s, 2H), 2.30 (m, 4H), 1.50 (m, 4H); FAB MS 516.2 (M+1).

EXAMPLE 63

Preparation of (R)-6-Hydroxy-3-[3-methoxy-4-(1-pyrrolidinylmethyl)benzyl]-2-[4-(5-oxopyrrolidin-2-ylmethoxy)phenyl]benzo[b]thiophene Oxalate

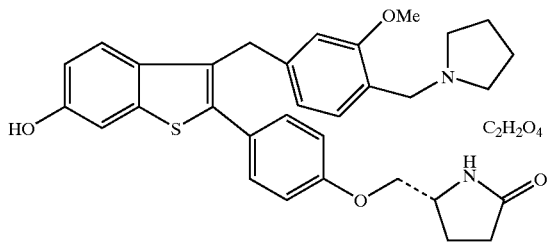

Part A. (R)-6-Benzyloxy-3-[3-methoxy-4-(1-pyrrolidinylmethyl)benzyl]-2-[4-(5-oxopyrrolidin-2-ylmethoxy)phenyl]benzo[b]thiophene.

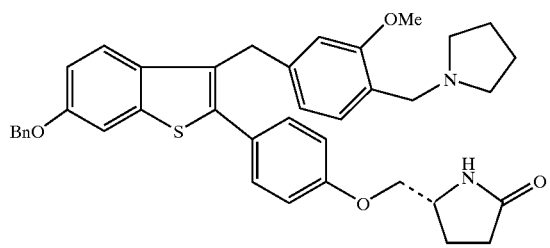

The title compound was prepared in 50% yield from 6-benzyloxy-2-(4-hydroxyphenyl)-3-[3-methoxy-4-(1-pyrrolidinylmethyl)benzyl]benzo[b]thiophene (Example 35, Part C) and (R)-(−)-5-(hydroxymethyl)-2-pyrrolidinone following the general procedure outlined in Example 2, Part A.

FDMS 633 (M+1); Anal. calcd for $C_{39}H_{40}N_2O_4 \cdot 0.8\ H_2O$: C, 72.37; H, 6.48; N, 4.33. Found: C, 72.24; H, 6.21; N, 4.72.

Part B. (R)-6-Hydroxy-3-[3-methoxy-4-(1-pyrrolidinylmethyl)benzyl]-2-[4-(5-oxopyrrolidin-2-ylmethoxy)phenyl]benzo[b]thiophene Oxalate.

The title compound was prepared in 83% yield from (R)-6-benzyloxy-3-[3-methoxy-4-(1-pyrrolidinylmethyl)benzyl]-2-[4-(5-oxopyrrolidin-2-yl)methoxy]phenyl]benzo[b]thiophene following the procedure detailed in Example 8, Part F.

ISMS 541 (M−1), 543 (M+1); IR (KBr) 3400 (br), 3221 (br), 1683, 1609 cm$^{-1}$.

EXAMPLE 64

Preparation of (±)-3-[3-Methoxy-4-(1-pyrrolidinylmethyl)benzyl]-2-[4-(2-oxo-oxazolidin-4-ylmethoxy)phenyl]benzo[b]thiophene Oxalate

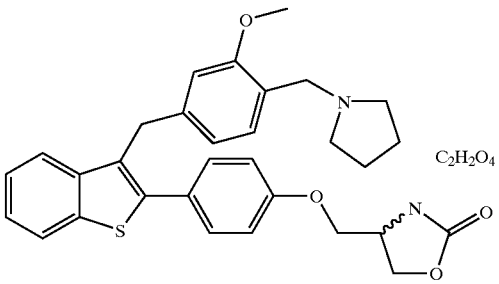

4-[3-[3-Methoxy-4-(1-pyrrolidinylmethyl)benzyl]benzo[b]thiophen-2-yl]phenol 0.22 g; 0.50 mmol), 0.15 g (0.55 mmol) of (±)-4-tosyloxymethyloxazolidin-2-one [J. Chem. Soc. Perkin Trans. I, 1675–1678 (1994)] and $Cs_2CO_3$ (0.35 g; 0.75 mmol) were combined in 2 mL of DMF in a flame-dried, argon-filled flask, and stirred at room temperature overnight. After cooling to room temperature, water (25 mL) was added to the mixture, which was filtered, and washed with fresh water. The product was purified by flash chromatography on silica gel, eluting with EtOAc(10–90%)/Et$_3$N(0–5%)/MeOH(0–5%), to afford the title product as a white, foamy solid (90 mg; 33% yield).

$^1$H NMR CDCl$_3$ δ 7.83 (m, 1H), 7.55 (m, 1H), 7.43 (d, J=8.6 Hz, 2H), 7.30 (m, 2H), 7.20 (d, J=7.6 Hz, 1H), 6.90 (d, J=8.7 Hz, 2H), 6.66 (m, 2H), 5.69 (br s, 1H), 4.56 (t, J=10.3 Hz, 1H), 4.27 (q, J=5.0 Hz, 2H), 4.23 (s, 2H), 4.04 (m, 2H), 3.69 (s, 3H), 3.64 (s, 2H), 2.60 (br s, 4H), 1.79 (br s, 4H). FAB+ Exact Mass calc'd for $C_{31}H_{33}N_2O_4S$: 529.2161; Found: 529.2155.

What is claimed is:

1. A compound of formula I or a pharmaceutically acceptable salt thereof

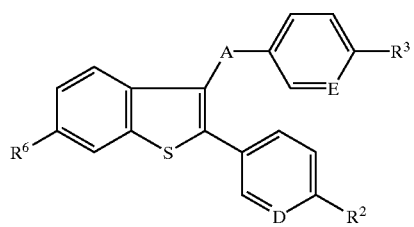

wherein

A is carbonyl or methylene;

D is CH or CR$^d$ in which R$^d$ is methyl or methoxy;

E is CH or CR$^e$ in which R$^e$ is methyl, methoxy or halo;

$R^2$ is —$NR^a$—CO—$(CH_2)_m$—$R^b$ or —O—$CH_2$—$R^b$ in which m is 0 or 1, $R^a$ is hydrogen or methyl, and $R^b$ is a ring of formula XII or formula XIII

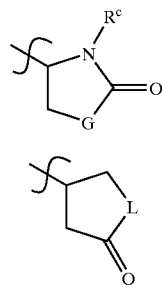

XII

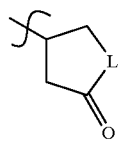

XIII in which G is O, S, NH, $CH_2$ or $CH_2$—$CH_2$ and $R^c$ is hydrogen or methyl, and L is $NR^f$ or $CH_2$ and $R^f$ is hydrogen or methyl; or $R^2$ is —$NHCOR^g$ in which $R^g$ is a five-membered heteroaromatic ring having 2 heteroatoms selected from O, S and N and in which the carbonyl group is bonded to a ring carbon situated between a ring heteroatom and another ring carbon; or $R^g$ is 1,1-dioxo-isothiazolidin-3-yl; or $R^g$ is —$COR^u$ in which $R^u$ is methoxy, amino or phenyl; or $R^2$ is —$(CH_2)_n$—$R^h$, —O—$(CH_2)_n$—$R^h$ or —NH—$(CH_2)_n$—$R^h$ in which n is 1 or 2 and $R^h$ is cyclopentyl, cyano, or —$CONR^iR^j$ in which $R^i$ and $R^j$ are independently hydrogen or methyl or the group $NR^iR^j$ is pyrrolidino, piperidino, or morpholino; or $R^2$ is —$X^2$—$(CH_2)_p$—$R^k$, or —O—$CH_2$—$CH(CH_3)$—$R^k$ in which $X^2$ is a direct bond, methylene or O and p is 1, 2 or 3, provided that when p is 1, then $X^2$ is a direct bond, and $R^k$ is 2-oxopyrrolidin-1-yl or $NHCOR^m$ in which $R^m$ is (1–3C)alkyl, phenyl or pyridyl; or $R^2$ is —NH—CO—$NR^iR^j$ in which $R^i$ and $R^j$ are independently hydrogen or methyl or the group $NR^iR^j$ is pyrrolidino, piperidino, or morpholino; or $R^2$ is —O—CO—$NR^pR^q$ in which $R^p$ and $R^q$ are independently hydrogen, methyl or ethyl or the group $NR^pR^q$ is pyrrolidino, piperidino, or morpholino; or $R^2$ is —NH—$SO_2$—$R^r$ in which $R^r$ is (1–3C)alkyl or phenyl; or $R^2$ is 2-oxo-oxazolidin-5-yl or 1-hydroxy-2-(methylsulfonylamino)ethyl; and $R^3$ is —$X^3$—$(CH_2)_s$—$NR^sR^t$ in which $X^3$ is a direct bond, methylene or O; s is 1 or 2; provided that when s is 1, then $X^3$ is a direct bond; and $R^s$ and $R^t$ are independently hydrogen or (1–3C)alkyl or the group $NR^sR^t$ is pyrrolidino, piperidino, or morpholino; and $R^6$ is hydrogen, hydroxy or methoxy; or A, E, $R^3$ and $R^6$ are defined as above; $R^2$ is hydrogen and D is C—NH—CO—$NR^iR^j$ or C—NH—CO—$COR^u$ in which $R^i$, $R^j$ and $R^u$ are defined as above;

provided the compound of formula I is not a urethane wherein A is carbonyl; D is CH; E is CH; $R^2$ is —O—CO—$NR^pR^q$ in which one of $R^p$ and $R^q$ is hydrogen, and the other of $R^p$ and $R^q$ is methyl or ethyl; $R^3$ is —O—$(CH_2)_2$—$NR^sR^t$ in which $R^s$ and $R^t$ are independently (1–3C)alkyl or the group $NR^sR^t$ is pyrrolidino, piperidino, or morpholino; and $R^6$ is hydroxy or methoxy;

further provided the compound of formula I is not a urethane wherein A is carbonyl; D is CH; E is CH; $R^2$ is —O—CO—$NR^pR^q$ in which one of $R^p$ and $R^q$ is hydrogen and the other of $R^p$ and $R^q$ is methyl or ethyl, or each of $R^p$ and $R^q$ is methyl or ethyl; $R^3$ is —O—$(CH_2)_2$—$NR^sR^t$ in which $R^s$ and $R^t$ are each hydrogen or the group $NR^sR^t$ is pyrrolidino or piperidino; and $R^6$ is hydrogen, hydroxy or methoxy;

and further provided the compound of formula I is not a sulfonamide wherein A is carbonyl; D is CH or $CR^d$ in which $R^d$ is methyl or methoxy; E is CH or $CR^e$ in which $R^e$ is methyl, methoxy or halo; $R^2$ is —NH—$SO_2$—$R^r$ in which $R^r$ is (1–3C)alkyl or phenyl; $R^3$ is —$X^3$—$(CH_2)_s$—$NR^sR^t$ in which $X^3$ is a direct bond, methylene or O; s is 1 or 2; provided that when s is 1, then $X^3$ is a direct bond; and $R^s$ and $R^t$ are independently hydrogen or (1–3C)alkyl or the group $NR^sR^t$ is pyrrolidino, piperidino, or morpholino; and $R^6$ is hydrogen, hydroxy or methoxy.

2. The compound of claim 1 or pharmaceutically acceptable salt thereof wherein

A is carbonyl or methylene;

D is CH or $CR^d$ in which $R^d$ is methyl or methoxy;

E is CH or $CR^e$ in which $R^e$ is methyl, methoxy or halo;

$R^2$ is —$NR^a$—CO—$(CH_2)_m$—$R^b$ or —O—$CH_2$—$R^b$ in which m is 0 or 1, $R^a$ is hydrogen or methyl, and $R^b$ is a ring of formula XII or formula XIII

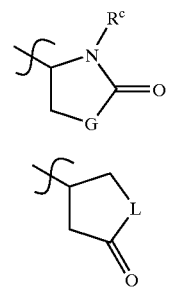

XII

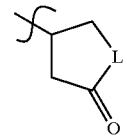

XIII in which G is O, S, NH or $CH_2$ and $R^c$ is hydrogen or methyl, and L is $NR^f$ or $CH_2$ and $R^f$ is hydrogen or methyl; or $R^2$ is —$NHCOR^g$ in which $R^g$ is a five-membered heteroaromatic ring having 2 heteroatoms selected from O, S and N and in which the carbonyl group is bonded to a ring carbon situated between a ring heteroatom and another ring carbon; or $R^2$ is —$(CH_2)_n$—$R^h$, —O—$(CH_2)_n$—$R^h$ or —NH—$(CH_2)_n$—$R^h$ in which n is 1 or 2 and $R^h$ is cyclopentyl, cyano, or —$CONR^iR^j$ in which $R^i$ and $R^j$ are independently hydrogen or methyl or the group $NR^iR^j$ is pyrrolidino, piperidino, or morpholino; or $R^2$ is —$X^2$—$(CH_2)_p$—$R^k$, or —O—$CH_2$—$CH(CH_3)$—$R^k$ in which $X^2$ is a direct bond, methylene or O and p is 1, 2 or 3, provided that when p is 1, then $X^2$ is a direct bond, and $R^k$ is 2-oxopyrrolidin-1-yl or $NHCOR^m$ in which $R^m$ is (1–3C)alkyl, phenyl or pyridyl; or $R^2$ is —NH—CO—$NR^iR^j$ in which $R^i$ and $R^j$ are independently hydrogen or methyl or the group $NR^iR^j$ is pyrrolidino, piperidino, or morpholino; or $R^2$ is —O—CO—$NR^pR^q$ in which $R^p$ and $R^q$ are independently hydrogen, methyl or ethyl or the group $NR^pR^q$ is pyrrolidino, piperidino, or morpholino; or $R^2$ is —NH—$SO_2$—$R^r$ in which $R^r$ is (1–3C)alkyl or phenyl;

$R^3$ is —$X^3$—$(CH_2)_s$—$NR^sR^t$ in which $X^3$ is a direct bond, methylene or O; s is 1 or 2; provided that when s is 1, then $X^3$ is a direct bond; and $R^s$ and $R^t$ are independently hydrogen or (1–3C)alkyl or the group $NR^sR^t$ is pyrrolidino, piperidino, or morpholino; and $R^6$ is hydrogen, hydroxy or methoxy.

3. The compound or salt thereof claim 1 or 2 wherein halo is fluoro, chloro, bromo or iodo; and a (1–3C)alkyl group is methyl, ethyl, propyl or isopropyl.

4. The compound or salt thereof of claim 1 wherein, independently,

D is CH;

E is CH or $CR^e$ in which $R^e$ is methyl or methoxy; and $R^3$ is pyrrolidinomethyl, morpholinomethyl or 2-pyrrolidinoethoxy.

5. The compound of claim 1 wherein $R^2$ is —$NR^a$—CO—$(CH_2)_m$—$R^b$ in which m is 0, $R^a$ is hydrogen, and $R^b$ is a ring of formula XII in which G is $CH_2$ and $R^c$ is methyl.

6. The compound or salt thereof of claim 1 wherein $R^2$ is —O—$CH_2$—$R^b$ in which $R^b$ is a ring of formula XII in which G is O, NH or $CH_2$ and $R^c$ is hydrogen.

7. The compound or salt thereof of claim 1 wherein $R^2$ is —O—$(CH_2)_n$—$R^h$ in which n is 1 and $R^h$ is —$CONR^iR^j$ in which $R^i$ and $R^j$ are independently hydrogen or methyl.

8. The compound or salt thereof of claim 1 wherein $R^6$ is hydroxy.

9. The compound or salt thereof of claim 1 wherein A is methylene.

10. The compound of claim 1 wherein the compound of formula I is selected from (a) (S)-6-hydroxy-3-[3-methyl-4-(1-pyrrolidinylmethyl)benzyl]-2-[4-(5-oxopyrrolidin-2-ylmethoxy)phenyl]benzo[b]thiophene, (b) 6-hydroxy-3-[3-methyl-4-[(1-pyrrolidinyl)methyl]benzyl]-2-[4-(2-oxooxazolidin-4-ylmethoxy)phenyl]benzo[b]thiophene, (c) 6-hydroxy-3-[3-methyl-4-[(1-pyrrolidinyl)methyl]benzyl]-2-[4-(2-oxoimidazolidin-4-ylmethoxy)phenyl]benzo[b]thiophene, (d) (R)-6-hydroxy-3-[4-[3-methyl-(1-pyrrolidinylmethyl)benzyl]-2-[4-[(2-oxopyrrolidin-5-yl)methoxy]phenyl]benzo[b]thiophene, (e) 6-hydroxy-3-[3-methyl-4-(1-pyrrolidinylmethyl)benzyl]-2-[4-(1-methyl-5-oxopyrrolidin-2-ylcarbonylamino)phenyl]benzo[b]thiophene, and (f) 2-[4-(aminooxoacetylamino)phenyl]-2-hydroxy-3-[3-methoxy-4-(1-pyrrolidinylmethyl)benzyl]benzo[b]thiophene;

or a pharmaceutically acceptable salt thereof.

11. An acid addition salt of a compound of formula I as claimed in claim 1 made with an acid which affords a pharmaceutically acceptable anion.

12. The compound or salt thereof of claim 4 wherein, independently,

D is CH;

E is CH or $CR^e$ in which $R^e$ is methyl or methoxy; and $R^3$ is pyrrolidinomethyl, morpholinomethyl or 2-pyrrolidinoethoxy.

13. The compound or salt thereof of claim 3, wherein, independently,

D is CH;

E is CH or $CR^e$ in which $R^e$ is methyl or methoxy; and $R^3$ is pyrrolidinomethyl, morpholinomethyl or 2-pyrrolidinoethoxy.

14. The compound of any one of claims 2 and 4 wherein $R^2$ is —$NR^a$—CO—$(CH_2)_m$—$R^b$ in which m is 0, $R^a$ is hydrogen, and $R^b$ is a ring of formula XII in which G is $CH^2$ and $R^c$ is methyl.

15. The compound of claim 3 wherein $R^2$ is —$NR^a$—CO—$(CH_2)_m$—$R^b$ in which m is 0, $R^a$ is hydrogen, and $R^b$ is a ring of formula XII in which G is $CH_2$ and $R^c$ is methyl.

16. The compound or salt thereof of any one of claims 2 and 4 wherein $R^2$ is —O—$CH_2$—$R^b$ in which $R^b$ is a ring of formula XII in which G is O, NH or $CH_2$ and $R^c$ is hydrogen.

17. The compound of claim 3 wherein $R^2$ is —O—$CH_2$—$R^b$ in which $R^b$ is a ring of formula XII in which G is O, NH or $CH_2$ and $R^c$ is hydrogen.

18. The compound or salt thereof of any one of claims 1 or 4 wherein $R^2$ is —O—$(CH_2)_n$—$R^h$ in which n is 1 and $R^h$ is —$CONR^iR^j$ in which $R^i$ and $R^j$ are independently hydrogen or methyl.

19. The compound or salt thereof of claim 3 wherein $R^2$ is —O—$(CH_2)_n$—$R^h$ in which n is 1 and $R^h$ is —$CONR^iR^j$ in which $R^i$ and $R^i$ are independently hydrogen or methyl.

20. The compound or salt thereof of any one of claims 2, 4, 5, 6 and 7 wherein $R^6$ is hydroxy.

21. The compound or salt thereof of claim 3 wherein $R^6$ is hydroxy.

22. The compound or salt thereof of any one of claims 2, 4, 5, 6, 7 and 8 wherein A is methylene.

23. The compound or salt thereof of claim 3 wherein A is methylene.

24. A pharmaceutical formulation comprising in association with a pharmaceutically acceptable carrier, diluent or excipient, a compound of formula I (or a pharmaceutically acceptable salt thereof) as claimed in claim 1.

25. A method of inhibiting thrombin comprising administering to a mammal in need of treatment an effective amount of a thrombin inhibiting compound of formula I or a pharmaceutically acceptable salt thereof

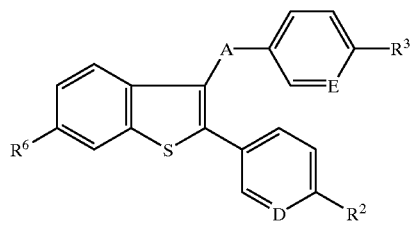

I wherein

A is carbonyl or methylene;

D is CH or $CR^d$ in which $R^d$ is methyl or methoxy;

E is CH or $CR^e$ in which $R^e$ is methyl, methoxy or halo;

$R^2$ is —$NR^a$—CO—$(CH_2)_m$—$R^b$ or —O—$CH_2$—$R^b$ in which m is 0 or 1, $R^a$ is hydrogen or methyl, and $R^b$ is a ring of formula XII or formula XIII

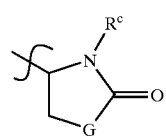

XII

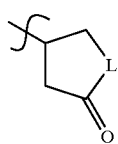

XIII in which G is O, S, NH, CH$_2$ or CH$_2$—CH$_2$ and R$^c$ is hydrogen or methyl, and L is NR$^f$ or CH$_2$ and R$^f$ is hydrogen or methyl; or R$^2$ is —NHCOR$^g$ in which R$^g$ is a five-membered heteroaromatic ring having 2 heteroatoms selected from O, S and N and in which the carbonyl group is bonded to a ring carbon situated between a ring heteroatom and another ring carbon; or R$^g$ is 1,1-dioxo-isothiazolidin-3-yl; or R$^g$ is —COR$^u$ in which R$^u$ is methoxy, amino or phenyl; or R$^2$ is —(CH$_2$)$_n$—R$^h$, —O—(CH$_2$)$_n$—R$^h$ or —NH—(CH$_2$)$_n$—R$^h$ in which n is 1 or 2 and R$^h$ is cyclopentyl, cyano, or —CONR$^i$R$^j$ in which R$^i$ and R$^j$ are independently hydrogen or methyl or the group NR$^i$R$^j$ is pyrrolidino, piperidino, or morpholino; or R$^2$ is —X$^2$—(CH$_2$)$_p$—R$^k$, or —O—CH$_2$—CH(CH$_3$)—R$^k$ in which X$^2$ is a direct bond, methylene or O and p is 1, 2 or 3, provided that when p is 1, then X$^2$ is a direct bond, and R$^k$ is 2-oxopyrrolidin-1-yl or NHCOR$^m$ in which R$^m$ is (1–3C)alkyl, phenyl or pyridyl; or R$^2$ is —NH—CO—NR$^i$R$^j$ in which R$^i$ and R$^j$ are independently hydrogen or methyl or the group NR$^i$R$^j$ is pyrrolidino, piperidino, or morpholino; or R$^2$ is —O—CO—NR$^p$R$^q$ in which R$^p$ and R$^q$ are independently hydrogen, methyl or ethyl or the group NR$^p$R$^q$ is pyrrolidino, piperidino, or morpholino; or R$^2$ is —NH—SO$_2$—R$^r$ in which R$^r$ is (1–3C)alkyl or phenyl; or R$^2$ is 2-oxo-oxazolidin-5-yl or 1-hydroxy-2-(methylsulfonylamino)ethyl; and R$^3$ is —X$^3$—(CH$_2$)$_s$—NR$^s$R$^t$ in which X$^3$ is a direct bond, methylene or O; s is 1 or 2; provided that when s is 1, then X$^3$ is a direct bond; and R$^s$ and R$^t$ are independently hydrogen or (1–3C)alkyl or the group NR$^s$R$^t$ is pyrrolidino, piperidino, or morpholino; and R$^6$ is hydrogen, hydroxy or methoxy; or A, E, R$^3$ and R$^6$ are defined as above; R$^2$ is hydrogen; and D is C—NH—CO—NR$^i$R$^j$ or C—NH—CO—COR$^u$ in which R$^i$, R$^j$ and R$^u$ are defined as above.

26. The method of claim 25 wherein the thrombin inhibiting compound of formula I or pharmaceutically acceptable salt thereof is one wherein A is carbonyl or methylene;

D is CH or CR$^d$ in which R$^d$ is methyl or methoxy;

E is CH or CR$^e$ in which R$^e$ is methyl, methoxy or halo;

R$^2$ is —NR$^a$—CO—(CH$_2$)$_m$—R$^b$ or —O—CH$_2$—R$^b$ in which m is 0 or 1, R$^a$ is hydrogen or methyl, and R$^b$ is a ring of formula XII or formula XIII

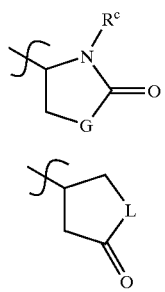

XII

XIII in which G is O, S, NH or CH$_2$ and R$^c$ is hydrogen or methyl, and L is NR$^f$ or CH$_2$ and R$^f$ is hydrogen or methyl; or R$^2$ is —NHCOR$^g$ in which R$^g$ is a five-membered heteroaromatic ring having 2 heteroatoms selected from O, S and N and in which the carbonyl group is bonded to a ring carbon situated between a ring heteroatom and another ring carbon; or R$^2$ is —(CH$_2$)$_n$—R$^h$, —O—(CH$_2$)$_n$—R$^h$ or —NH—(CH$_2$)$_n$—R$^h$ in which n is 1 or 2 and R$^h$ is cyclopentyl, cyano, or —CONR$^i$R$^j$ in which R$^i$ and R$^j$ are independently hydrogen or methyl or the group NR$^i$R$^j$ is pyrrolidino, piperidino, or morpholino; or R$^2$ is —X$^2$—(CH$_2$)$_p$—R$^k$, or —O—CH$_2$—CH(CH$_3$)—R$^k$ in which X$^2$ is a direct bond, methylene or O and p is 1, 2 or 3, provided that when p is 1, then X$^2$ is a direct bond, and R$^k$ is 2-oxopyrrolidin-1-yl or NHCOR$^m$ in which R$^m$ is (1–3C)alkyl, phenyl or pyridyl; or R$^2$ is —NH—CO—NR$^i$R$^j$ in which R$^i$ and R$^j$ are independently hydrogen or methyl or the group NR$^i$R$^j$ is pyrrolidino, piperidino, or morpholino; or R$^2$ is —O—CO—NR$^p$R$^q$ in which R$^p$ and R$^q$ are independently hydrogen, methyl or ethyl or the group NR$^p$R$^q$ is pyrrolidino, piperidino, or morpholino; or R$^2$ is —NH—SO$_2$—R$^r$ in which R$^r$ is (1–3C)alkyl or phenyl;

R$^3$ is —X$^3$—(CH$_2$)$_s$—NR$^s$R$^t$ in which X$^3$ is a direct bond, methylene or O; s is 1 or 2; provided that when s is 1, then X$^3$ is a direct bond; and R$^s$ and R$^t$ are independently hydrogen or (1–3C)alkyl or the group NR$^s$R$^t$ is pyrrolidino, piperidino, or morpholino; and R$^6$ is hydrogen, hydroxy or methoxy.

27. The method of claim 25 or 26 wherein halo is fluoro, chloro, bromo or iodo; and a (1–3C)alkyl group is methyl, ethyl, propyl or isopropyl.

28. The method of claim 25 wherein, independently,

D is CH;

E is CH or CR$^e$ in which R$^e$ is methyl or methoxy; and

R$^3$ is pyrrolidinomethyl, morpholinomethyl or 2-pyrrolidinoethoxy.

29. The method of claim 25 wherein R$^2$ is —NR$^a$—CO—(CH$_2$)$_m$—R$^b$ in which m is 0, R$^a$ is hydrogen, and R$^b$ is a ring of formula XII in which G is CH$_2$ and R$^c$ is methyl.

30. The method of claim 25 wherein R$^2$ is —O—CH$_2$—R$^b$ in which R$^b$ is a ring of formula XII in which G is O, NH or CH$_2$ and R$^c$ is hydrogen.

31. The method of claim 25 wherein $R^2$ is —O—$(CH_2)_n$—$R^h$ in which n is 1 and $R^h$ is —$CONR^iR^j$ in which $R^i$ and $R^j$ are independently hydrogen or methyl.

32. The method of claim 25 wherein $R^6$ is hydroxy.

33. The method of claim 25 wherein A is methylene.

34. The method of claim 25 wherein the compound of formula I is selected from
   (a) (S)-6-hydroxy-3-[3-methyl-4-(1-pyrrolidinylmethyl)benzyl]-2-[4-(5-oxopyrrolidin-2-ylmethoxy)phenyl]benzo[b]thiophene,
   (b) 6-hydroxy-3-[3-methyl-4-[(1-pyrrolidinyl)methyl]benzyl]-2-[4-(2-oxooxazolidin-4-ylmethoxy)phenyl]benzo[b]thiophene,
   (c) 6-hydroxy-3-[3-methyl-4-[(1-pyrrolidinyl)methyl]benzyl]-2-[4-(2-oxoimidazolidin-4-ylmethoxy)phenyl]benzo[b]thiophene,
   (d) (R)-6-hydroxy-3-[4-[3-methyl-(1-pyrrolidinylmethyl)benzyl]-2-[4-[(2-oxopyrrolidin-5-yl)methoxy]phenyl]benzo[b]thiophene,
   (e) 6-hydroxy-3-[3-methyl-4-(1-pyrrolidinylmethyl)benzyl]-2-[4-(1-methyl-5-oxopyrrolidin-2-ylcarbonylamino)phenyl]benzo[b]thiophene, and
   (f) 2-[4-(aminooxoacetylamino)phenyl]-2-hydroxy-3-[3-methoxy-4-(1-pyrrolidinylmethyl)benzyl]benzo[b]thiophene;
or a pharmaceutically acceptable salt thereof.

35. The method of claim 26 wherein, independently,
D is CH;
E is CH or $CR^e$ in which $R^e$ is methyl or methoxy; and
$R^3$ is pyrrolidinomethyl, morpholinomethyl or 2-pyrrolidinoethoxy.

36. The method of claim 27 wherein, independently,
D is CH
E is CH or $CR^e$ in which $R^e$ is methyl or methoxy; and
$R^3$ is pyrrolidinomethyl, morpholinomethyl or 2-pyrrolidinoethoxy.

37. The method of any one of claims 26 and 28 wherein $R^2$ is —$NR^a$—CO—$(CH_2)_m$—$R^b$ in which m is 0, $R^a$ is hydrogen, and $R^b$ is a ring of formula XII in which G is $CH_2$ and $R^c$ is methyl.

38. The method of claim 27 wherein $R^2$ is —$NR^a$—CO—$(CH_2)_m$—$R^b$ in which m is 0, $R^a$ is hydrogen, and $R^b$ is a ring of formula XII in which G is $CH_2$ and $R^c$ is methyl.

39. The method of any one of claims 26 and 28 wherein $R^2$ is —O—$CH_2$—$R^b$ in which $R^b$ is a ring of formula XII in which G is O, NH or $CH_2$ and $R^c$ is hydrogen.

40. The method of claim 27 wherein $R^2$ is —O—$CH_2$—$R^b$ in which $R^b$ is a ring of formula XII in which G is O, NH or $CH_2$ and $R^c$ is hydrogen.

41. The method of any one of claims 26 and 28 wherein $R^2$ is —O—$(CH_2)_n$—$R^h$ in which n is 1 and $R^h$ is —$CONR^iR^j$ in which $R^i$ and $R^j$ are independently hydrogen or methyl.

42. The method of claim 27 wherein $R^2$ is —O—$(CH_2)_n$—$R^h$ in which n is 1 and $R^h$ is —$CONR^iR^j$ in which $R^i$ and $R^j$ are independently hydrogen or methyl.

43. The method of any one of claims 26, 28, 29, 30 and 31 wherein $R^6$ is hydroxy.

44. The method of claim 27 wherein $R^6$ is hydroxy.

45. The method of any one of claims 26 28, 29, 30, 31 and 32 wherein A is methylene.

46. The method of claim 27 wherein A is methylene.

47. A process for preparing a compound of formula I or a pharmaceutically acceptable salt thereof as claimed in claim 1 which is selected from:
   (a) for a compound of formula I in which A is methylene, reductive removal of the hydroxy group of a corresponding alcohol of formula II; and

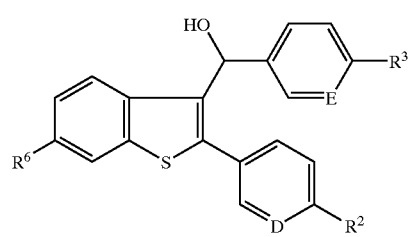

(b) for a compound of formula I in which $R^2$ is —O—$CH_2$—$R^b$ or —O—$(CH_2)_n$—$R^h$, alkylating the hydroxy group of a corresponding phenol of formula III;

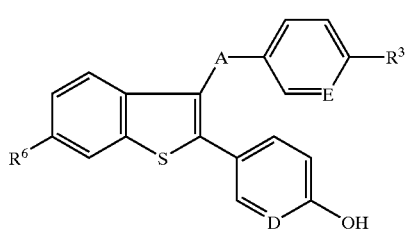

with a group of formula X—$CH_2$—$R^b$ or X—$(CH_2)_n$—$R^h$, respectively, or a protected derivative thereof, wherein X is a conventional leaving group;

whereafter, for any of the above procedures, when a functional group is protected using a protecting group, removing the protecting group;

whereafter, for any of the above procedures, when a pharmaceutically acceptable salt of a compound of formula I is required, it may be obtained by reacting the basic form of such a compound of formula I with an acid affording a physiologically acceptable counterion or by any other conventional procedure;

and wherein, unless more specifically described, the values of A, D, E, $R^2$, $R^3$ and $R^6$ are as defined in claim 26.

* * * * *